United States Patent
Imagawa et al.

(10) Patent No.: US 9,585,881 B2
(45) Date of Patent: *Mar. 7, 2017

(54) SUBSTITUTED PYRROLIDINES AS FACTOR XIA INHIBITORS FOR THE TREATMENT THROMBOEMBOLIC DISEASES

(71) Applicant: ONO PHARMACEUTICAL CO., LTD., Osaka (JP)

(72) Inventors: Akira Imagawa, Osaka (JP); Takashi Kondo, Osaka (JP); Taihei Nishiyama, Osaka (JP); Steve Courtney, Abingdon (GB); Chris Yarnold, Abingdon (GB); Osamu Ichihara, Tokyo (JP); Stuart Flanagan, Abingdon (GB)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/180,382

(22) Filed: Jun. 13, 2016

(65) Prior Publication Data

US 2016/0287582 A1  Oct. 6, 2016

Related U.S. Application Data

(63) Continuation of application No. 14/403,037, filed as application No. PCT/EP2013/060650 on May 23, 2013, now Pat. No. 9,394,250.

(30) Foreign Application Priority Data

May 24, 2012 (GB) .................................. 1209138.5

(51) Int. Cl.

| | |
|---|---|
| A61K 31/496 | (2006.01) |
| C07D 401/14 | (2006.01) |
| C07D 413/14 | (2006.01) |
| C07D 401/04 | (2006.01) |
| C07D 403/04 | (2006.01) |
| C07D 403/14 | (2006.01) |
| C07D 413/04 | (2006.01) |
| C07D 207/50 | (2006.01) |
| C07D 401/06 | (2006.01) |
| C07D 403/10 | (2006.01) |

(52) U.S. Cl.
CPC .......... *A61K 31/496* (2013.01); *C07D 207/50* (2013.01); *C07D 401/04* (2013.01); *C07D 401/06* (2013.01); *C07D 401/14* (2013.01); *C07D 403/04* (2013.01); *C07D 403/10* (2013.01); *C07D 403/14* (2013.01); *C07D 413/04* (2013.01); *C07D 413/14* (2013.01)

(58) Field of Classification Search
CPC .................................................... A61K 31/496
See application file for complete search history.

(56) References Cited

FOREIGN PATENT DOCUMENTS

| | | |
|---|---|---|
| EP | 2336105 | 6/2011 |
| WO | 9523608 | 9/1995 |
| WO | 0237937 | 5/2002 |
| WO | 2007070826 | 6/2007 |
| WO | 2007131982 | 11/2007 |
| WO | 2008064218 | 5/2008 |
| WO | 2008076805 | 6/2008 |
| WO | 2009152824 | 12/2009 |
| WO | 2010045580 | 4/2010 |

OTHER PUBLICATIONS

International Search Report for PCT/EP2013/060650 dated Jul. 17, 2013.
De Candia et al; "Novel factor Xa inhibitors: a patent review"; Expert Opinion on Therapeutic Patents; 19(11):1535-1580 (2009).
Search Report for Great Britain Application No. GB 1209138.5 dated Oct. 24, 2012.
Komoriya et al., "Design, synthesis and biological activity of amidinobicyclic compounds (derivatives of DX-9065a) as factor Xa inhibitors: SAR study of SI and aryl binding sites", Bioorg. Med. Chem., 12:2099-2114 (2004).
Kubinyi, "3D QSAR in Drug Design: Ligand-Protein Interactions and Molecular Similarity", Chapter, 2, pp. 243-244 (1998).
Wermuth, "Electronic Screening: Lead Finding from Database Mining", The Practice of Medicinal Chemistry, 2nd ed., Chapters 9-10, pp. 131-157 (2003).

*Primary Examiner* — Robert Havlin
(74) *Attorney, Agent, or Firm* — Sughrue Mion, PLLC

(57) ABSTRACT

The present invention provides compounds of the general formula (I), their salts and N-oxides, and solvates and prodrugs thereof (wherein the substituents are as defined in the description). The compounds of the general formula (I) are inhibitors of factor XIa, and are useful in the prevention of and/or therapy for thromboembolic diseases.

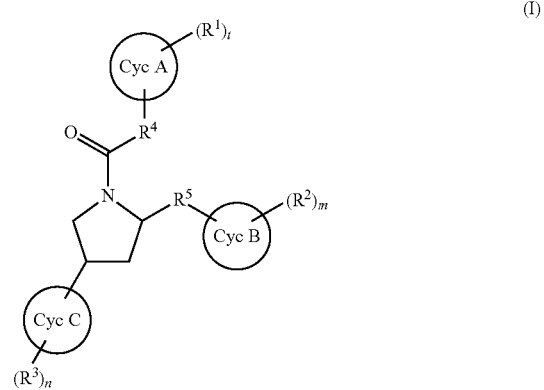

4 Claims, No Drawings

SUBSTITUTED PYRROLIDINES AS FACTOR XIA INHIBITORS FOR THE TREATMENT THROMBOEMBOLIC DISEASES

CROSS-REFERENCE TO RELATED APPLICATIONS

This application is Continuation of U.S. application Ser. No. 14/403,037, filed Nov. 21, 2014 (now allowed); which is a National Stage of International Application No. PCT/EP2013/060650, filed May 23, 2013, which claims priority based on Great Britain Application No. 1209138.5, filed May 24, 2012; the contents of all of which are incorporated herein by reference in their entirety.

TECHNICAL FIELD

The present invention relates to a series of pyrrolidine derivatives which are useful as inhibitors of factor XIa.

Thus, the present invention relates to a compound of formula (I):

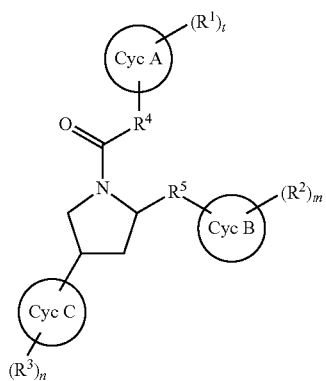

(I)

(wherein all symbols have the same meanings as described hereinafter) or a pharmaceutically acceptable salt thereof, an N-oxide thereof, a solvate thereof, or a prodrug thereof, use of such compounds in treatment and/or prevention of a thromboembolic disease and processes for the preparation of said compounds.

BACKGROUND OF THE INVENTION

Thromboembolism is an important cause of morbidity and mortality. It occurs when a blood clot breaks free and is carried by the blood stream to obstruct a blood vessel at another site. Thromboembolic disease includes venous thromboembolism, for example deep vein thrombosis or pulmonary embolism, arterial thrombosis, stroke and myocardial infarction.

Thromboembolic diseases may be treated using anticoagulants. One approach has been to target the inhibition of factor XIa (FXIa). Factor XIa is a plasma serine protease involved in the regulation of blood coagulation. Factor XIa is an activated form of factor XI, which is activated by factor XIIa, thrombin, and it is also autocatalytic. FXIa is a component of the "contact pathway" and activates factor IX by selectively cleaving arg-ala and arg-val peptide bonds. Factor IXa, in turn, activates factor X. The safety of this target is supported by the observations that FXI deficiency in humans (hemophilia C) results in a mild bleeding disorder. In addition to this, the efficacy and side effects of this target have been shown using experimental thrombosis and bleeding models in mice lacking FXI, and in baboons and rabbits treated with anti-FXI neutralizing antibodies. These results suggest that FXIa inhibitors will show a potent anti-thrombotic effect without bleeding. Therefore, factor XIa is an attractive target for anti-thrombotic therapy without the side effect of bleeding.

It has been described in Patent literature 1 that compound of formula (A):

(A)

wherein $A^A$ represents a 5- to 12-membered heterocycle, etc.; $L_{1A}$ represents —CH=CH—, etc.; $R^{11A}$ represents benzyl, etc.; $M^A$ represents imidazolyl, etc; are useful as selective inhibitors of factor XIa or dual inhibitors of FXIa and plasma kallikrein.

Furthermore, it has been described in Patent literature 2 that a compound of formula (B-I):

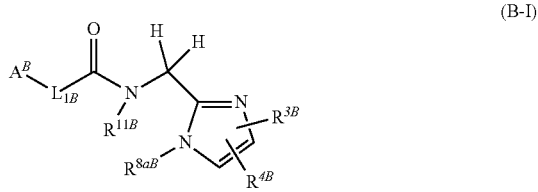

(B-I)

wherein $A^B$ represents a 5- to 12-membered heterocycle, etc.; $L_{1B}$ represents —CH=CH—, etc.; $R^{11B}$ represents benzyl, etc.; $R^{3B}$ represents phenyl, etc.; $R^{4B}$ represents chlorine, etc.; $R^{8aB}$ represents hydrogen, etc; or formula (B-II):

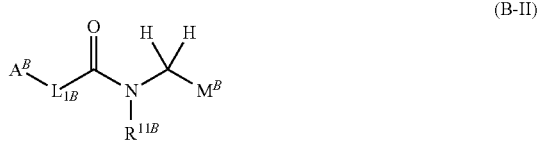

(B-II)

wherein $M^B$ represents pyridyl, etc.; and the other symbols have the same meanings as described above; inhibit factor XIa and/or plasma kallikrein.

Furthermore, it has been described in Patent literature 3 that a compound of formula (C):

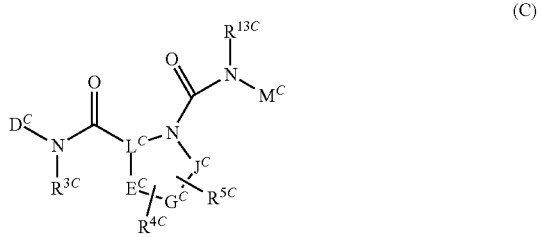

(C)

wherein $D^C$ represents C10 cycloalkyl or 10-membered heterocycloalkyl, etc.; $-L^C-E^C-G^C-J^C-$ represents —C—C—C—C, etc.; $R^{3C}$ represents hydrogen, etc.; $R^{4C}$ represents mono- or bicyclic heteroaryl, etc.; $R^{5C}$ represents hydrogen, etc.; $R^{13c}$ represents hydrogen, etc.; $M^C$ represents phenyl, etc.; are useful as inhibitors of factor Xa.

Furthermore, it has been described in Patent literature 4 that a compound of formula (D):

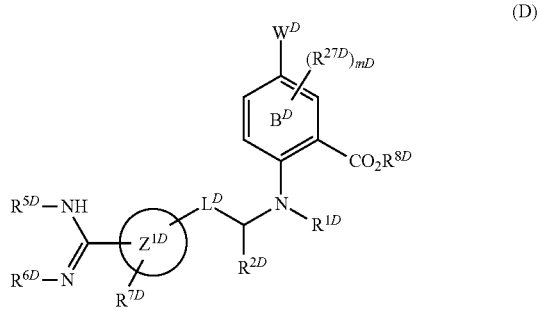

(D)

wherein ring $B^D$ represents phenyl, etc.; $W^D$ represents —$NH_2$, etc.; $Z^{1D}$ represents 5 to 7-membered monocyclic, etc.; $L^D$ represents —NH—CO—, etc.; $R^{1D}$ and $R^{2D}$ independently represents (i) hydrogen or (ii) are taken together to form a five-to-seven membered fully saturated heterocycle, etc.; $R^{5D}$ and $R^{6D}$ independently represents hydrogen, etc.; $R^{7D}$ represents —COOH, etc.; $R^{8D}$ represents hydrogen, etc.; $(R^{27D})_{mD}$ represents —COOH, etc.; are useful as inhibitors of factor VIIa, factor IXa, factor FXIa, tryptase, and urokinase.

Furthermore, it has been described in Patent literature 5 that a compound of formula (E):

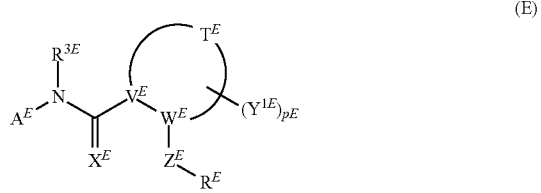

(E)

wherein $A^E$ represents aryl substituted by carboxyl, etc.; $R^{3E}$ represents hydrogen, etc.; $X^E$ represents oxygen, etc.; $V^E$ represents nitrogen, etc.; $W^E$ represents carbon, etc.; $Z^D$ represents —CO—, etc.; $R^E$ represents aryl substituted by —C(=NH)$NH_2$, etc.; $T^E$ represents $C_{2-6}$ alkylene, etc.; $(Y^{1E})_{pE}$ represents heterocyclo substituted by —$SO_2$-Me, etc.; are useful as anti-viral agent, however, it is not reported that the compound represented by formula (E) has factor XIa inhibitory activity.

Furthermore, it has been described in Patent literature 6 that a compound of formula (F):

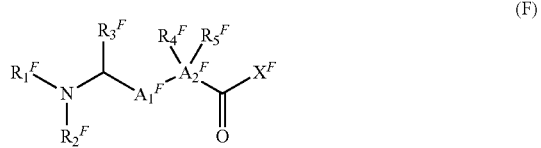

(F)

wherein ring $X^F$ represents N-containing ring, etc.; $A_1^F$ represents a bond, etc.; $A_2^F$ represents Aryl, etc.; $R_1^F$, $R_2^F$, $R_3^F$, $R_4^F$ and $R_5^F$ independently represents hydrogen, etc.; are useful as inhibitors of Apoptosis Proteins.

[Patent literature 1] WO2007070826
[Patent literature 2] WO2008076805
[Patent literature 3] WO2007131982
[Patent literature 4] WO2002037937
[Patent literature 5] WO2008064218
[Patent literature 6] WO2009152824

DISCLOSURE OF THE INVENTION

It is desirable to find new compounds which may be more effective in treating thromboembolic diseases. Advantageous compounds desirably have good inhibitory and selectivity for factor XIa.

The present inventors have made extensive studies to find a compound that can become a therapeutic agent for thromboembolic diseases. As a result, we have found that the object is achieved by a compound represented by formula (I), a salt thereof, an N-oxide thereof, a solvate thereof, or a prodrug thereof (hereinafter, which may be abbreviated to compounds of the present invention) have good inhibitory and selectivity for factor XIa and then we have completed the present invention.

Namely, the present invention relates to the following aspects:

(1) A compound represented by formula (I):

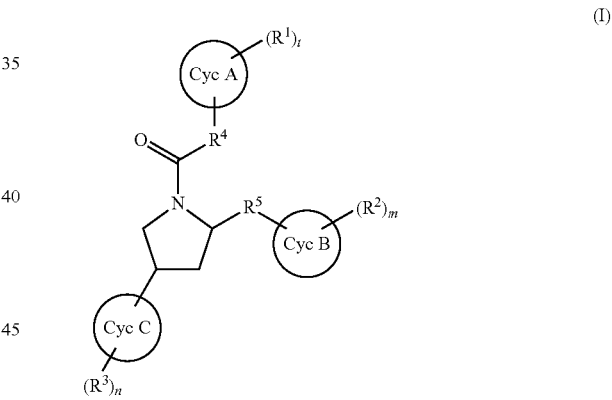

(I)

wherein Cyc A represents C3-C8 cycloalkyl, 5- to 10-membered heterocycloalkyl, C6-C10 aryl or 5- to 10-membered heteroaryl;

Cyc B represents C3-C8 cycloalkyl, 5- to 10-membered heterocycloalkyl, C6-C10 aryl or 5- to 10-membered heteroaryl;

Cyc C represents C3-C8 cycloalkyl, 5- to 10-membered heterocycloalkyl, C6-C10 aryl or 5- to 10-membered heteroaryl;

each $R^1$ may be the same or different and represents (1) C6-C10 aryl, (2) 5- to 10-membered heteroaryl, (3) C6-C10 aryl or 5- to 10-membered heteroaryl substituted with 1 to 5 groups selected from halogen, C1-4 alkyl, C1-4 alkoxy, —C1-4 alkylene-C1-4 alkoxy, CN, —COOH, —COO—C1-4 alkyl, —CO—$NH_2$, —OCON$H_2$, —OCCONH—C1-4 alkyl, —CONH—C1-4 alkyl, —NHCOO—C1-4 alkyl and —NHCO—C1-4 alkyl, (4) —C(=NH)$NH_2$, (5) —NH—C(=NH)$NH_2$, (6) C1-4 alkyl, (7) C2-4 alkenyl, (8) C2-4 alkynyl, (9) —C1-4 alkylene-NH$_2$, (10) C1-4 alkoxy, (11) CN, (12) —CO—C1-4 alkyl, (13) halogen or (14) —R$^{10}$—C(=NR$^{11}$)NR$^{12}$R$^{13}$;

wherein R$^{10}$ represents (1) a bond or (2) NH;

R$^{11}$, R$^{12}$ and R$^{13}$ each independently represents (1) hydrogen, (2) OH, (3) C1-4 alkyl, (4) C2-4 alkenyl, (5) C2-4 alkynyl, (6) C1-4 alkoxy, (7) —C1-4 alkylene-C1-4 alkoxy, (8) —CO—C1-4 alkyl, (9) —COO—C1-4 alkyl, (10) —OCO—C1-4 alkyl, (11) —CO—R$^{14}$, (12) —COO—R$^{15}$ or (13) —OCO—R$^{16}$, with the proviso that R$^{11}$, R$^{12}$ and R$^{13}$ do not all simultaneously represent hydrogen;

wherein R$^{14}$, R$^{15}$ and R$^{16}$ each independently represents C1-4 alkyl, C2-4 alkenyl or C2-4 alkynyl, which are substituted with 1 to 5 groups selected from C1-4 alkyl, C2-4 alkenyl, C2-4 alkynyl, halogen, trifluoromethyl, OH, —COO—C1-4 alkyl, COOH, oxo, C1-4 alkoxy, C6-C10 aryl, 5- to 10-membered heteroaryl and NR$^{17}$R$^{18}$;

wherein R$^{17}$ and R$^{18}$ each independently represents (1) hydrogen, (2) C1-4 alkyl, (3) C2-4 alkenyl or (4) C2-4 alkynyl;

t represents an integer of 0 to 6;

each R$^2$ may be the same or different and represents (1) —COOH, (2) —COO—C1-4 alkyl, (3) —COO—C1-4 alkylene-C1-4 alkoxy, (4) —NH$_2$, (5) —NH—C1-4 alkyl, (6) —NH—C1-4 alkylene-C1-4 alkoxy, (7) —NHCO—C1-4 alkyl, (8) —NHCO—C1-4 alkylene-C1-4 alkoxy, (9) —NHCOO—C1-4 alkyl, (10) —NHCOO—C1-4 alkylene-C1-4 alkoxy, (11) —CONH$_2$, (12) —CONH—C1-4 alkyl, (13) —CONH—C2-4 alkylene-C1-4 alkoxy, (14) halogen, (15) —SO$_2$—C1-4 alkyl, (16) oxo, (17) C1-4 alkoxy, (18) —CO—C1-4 alkyl, (19) —CO—C1-4 alkylene-C1-4 alkoxy or (20) —COO—C1-4 alkyl substituted with 1 to 5 groups selected from C1-4 alkyl, C2-4 alkenyl, C2-4 alkynyl, halogen, trifluoromethyl, OH, —COO—C1-4 alkyl, COOH, oxo, C1-4 alkoxy, C6-C10 aryl, 5- to 10-membered heteroaryl and NR$^{19}$R$^{20}$;

wherein R$^{19}$ and R$^{20}$ each independently represents (1) hydrogen, (2) C1-4 alkyl, (3) C2-4 alkenyl or (4) C2-4 alkynyl;

m represents an integer of 0 to 6;

each R$^3$ may be the same or different and represents (1) —COO—C1-4 alkyl, (2) oxo, (3) —CO—C1-4 alkyl, (4) —CO—NH$_2$, (5) —SO$_2$—NH$_2$ or (6) —SO$_2$—R$^6$-R$^7$;

n represents an integer of 0 to 6;

R$^6$ represents (1) a bond or (2) NH;

R$^7$ represents (1) C1-4 alkyl, (2) Cyc D or (3) C1-4 alkyl or Cyc D substituted with 1 to 5 R$^8$;

wherein Cyc D represents C3-C8 cycloalkyl, 5- to 10-membered heterocycloalkyl, C6-C10 aryl or 5- to 10-membered heteroaryl;

each R$^8$ may be the same or different and represents (1) —COOH, (2) —COO—C1-4 alkyl, (3) —COO—C1-4 alkylene-C1-4 alkoxy, (4) —NH$_2$, (5) —NH—C1-4 alkyl, (6) —NHCO—C1-4 alkyl, (7) —CONH$_2$, (8) —CONH—C1-4 alkyl (9) OH or (10) halogen;

R$^4$ represents (1) a bond, (2) C1-4 alkylene, (3) C2-4 alkenylene or (4) C2-4 alkynylene;

R$^5$ represents (1) —CONH—, (2) Cyc E or (3) Cyc E substituted with 1 to 5 R$^9$;

wherein Cyc E represents C3-C8 cycloalkyl, 5- to 10-membered heterocycloalkyl, C6-C10 aryl or 5- to 10-membered heteroaryl and each R$^9$ may be the same or different and represents C1-4 alkyl or halogen;

a salt thereof, an N-oxide thereof, a solvate thereof, or a prodrug thereof.

(2) The compound according to (1), wherein the compound represented by formula (I) represents a compound represented by formula (I-A):

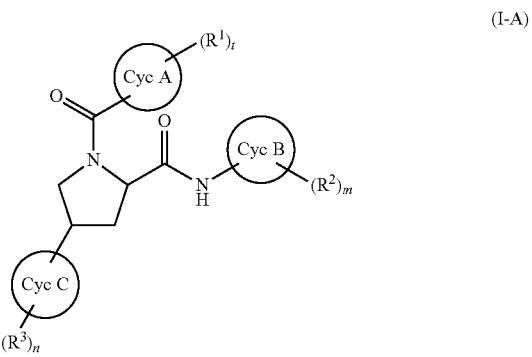

(I-A)

wherein all symbols have the same meanings as described above.

(3) The compound according to (2), wherein the compound represented by formula (I-A) represents a compound represented by formula (I-A-1):

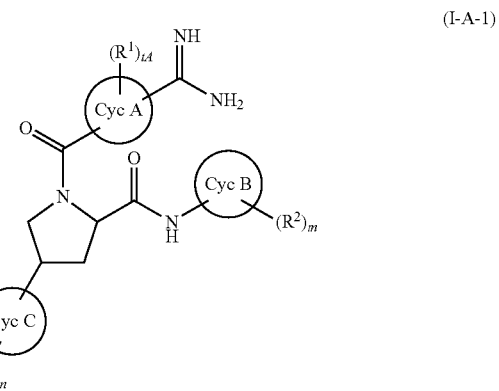

(I-A-1)

wherein to represents an integer of 0 to 5; and the other symbols have the same meanings as described above.

(4) The compound according to (2), wherein the compound represented by formula (I-A) represents a compound represented by formula (I-A-A-1):

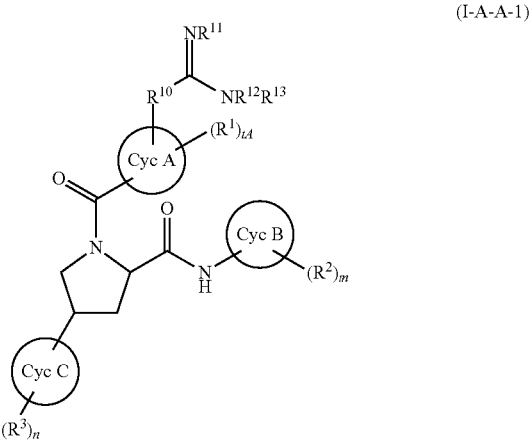

(I-A-A-1)

(5) The compound according to (1), wherein the compound represented by formula (I) represents a compound represented by formula (I-B):

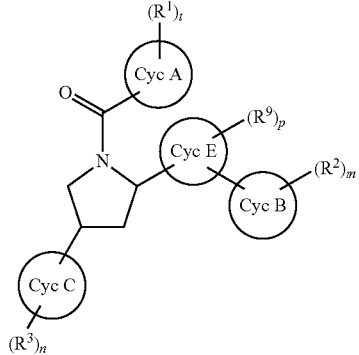

(I-B)

wherein p represents an integer of 0 to 5; and
the other symbols have the same meanings as described above.

(6) The compound according to (5), wherein the compound represented by formula (I-B) represents a compound represented by formula (I-B-1):

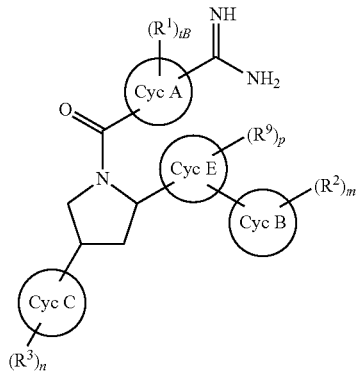

(I-B-1)

wherein tB represents an integer of 0 to 5; and
the other symbols have the same meanings as described above.

(7) The compound according to (5), wherein the compound represented by formula (I-B) represents a compound represented by formula (I-B-B-1):

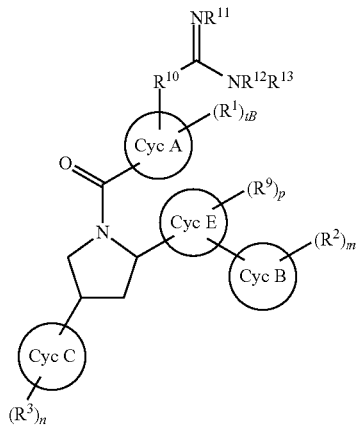

(I-B-B-1)

wherein all symbols have the same meanings as described above.

(8) The compound according to any one of (5) to (7), wherein Cyc E represents imidazolyl.

(9) The compound according to (1), wherein the compound represented by formula (I) represents a compound represented by formula (I-C):

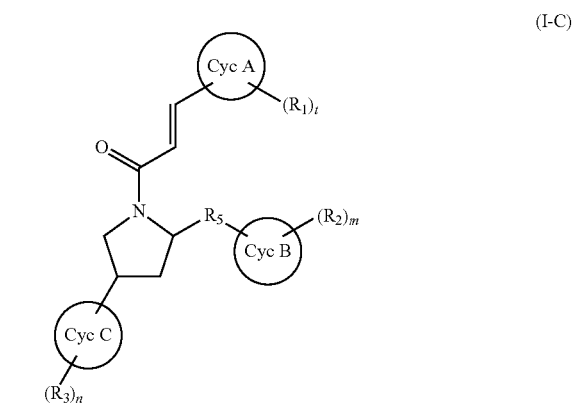

(I-C)

wherein all symbols have the same meanings as described above.

(10) The compound according to (9), wherein the compound represented by formula (I-C) represents a compound represented by formula (I-C-1):

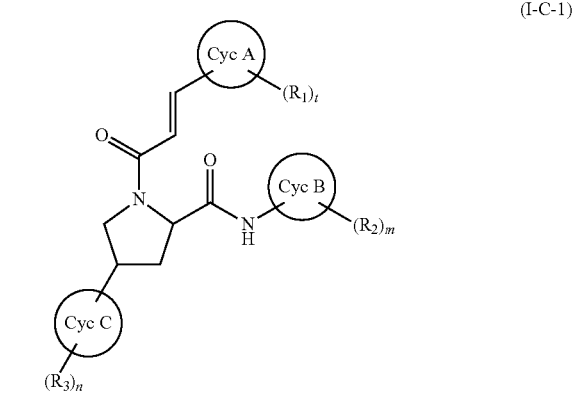

(I-C-1)

wherein all symbols have the same meanings as described above.

(11) The compound according to (9), wherein the compound represented by formula (I-C) represents a compound represented by formula (I-C-C-1):

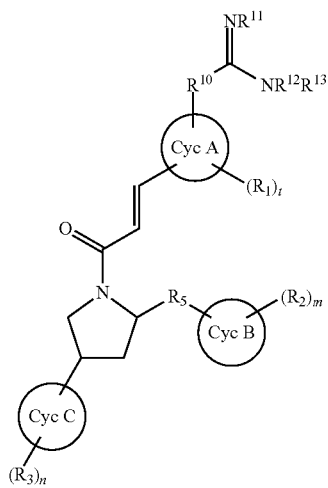

(I-C-C-1)

wherein all symbols have the same meanings as described above.

(12) The compound according to any one of (1) to (11), wherein Cyc A represents C3-C6 cycloalkyl, C6-C10 aryl or 5- to 6-membered heterocycloalkyl.

(13) The compound according to any one of (1) to (12), wherein Cyc A represents cyclohexyl, phenyl, piperidinyl or piperazinyl.

(14) The compound according to any one of (1) to (13), wherein Cyc B represents C6-C10 aryl or 5- to 6-membered heteroaryl.

(15) The compound according to any one of (1) to (14), wherein Cyc B represents phenyl or pyridyl.

(16) The compound according to any one of (1) to (15), wherein Cyc C represents pyrrolidinyl, piperidinyl, piperazinyl or morpholinyl.

(17) The compound according to any one of (1) to (16), wherein -Cyc C—$(R^3)_n$ represents

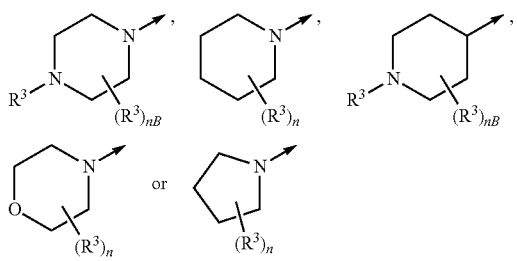

wherein nB represents an integer of 0 to 5;
the arrow represents a binding position; and
the other symbols have the same meanings as described above.

(18) The compound according to (17), wherein -Cyc C—$(R^3)_n$ represents

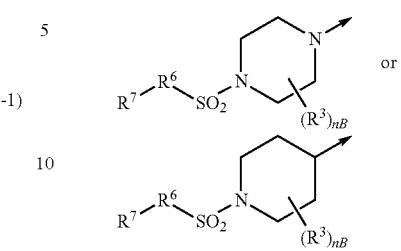

wherein the arrow represents a binding position; and
the other symbols have the same meanings as described above.

(19) The compound according to any one of (1), (2), (3), (5), (6) or (9), wherein the compound is selected from the group consisting of
(1) 4-[({(2S,4S)-1-[(1-carbamimidoyl-4-piperidinyl)carbonyl]-4-[4-(methylsulfonyl)-1-piperazinyl]-2-pyrrolidinyl}carbonyl)amino]benzoic acid,
(2) 4-[({(2S,4S)-1-(4-carbamimidoylbenzoyl)-4-[4-(methylsulfonyl)-1-piperazinyl]-2-pyrrolidinyl}carbonyl) amino]benzoic acid,
(3) 4-({[[(2S,4S)-1-{(2E)-3-[5-chloro-2-(1H-tetrazol-1-yl) phenyl]-2-propenoyl}-4-(4-morpholinyl)-2-pyrrolidinyl] carbonyl}amino)benzoic acid,
(4) (2S,4S)-1-{(2E)-3-[5-chloro-2-(1H-tetrazol-1-yl)phenyl]-2-propenoyl}-N-phenyl-4-[4-(phenylsulfonyl)-1-piperazinyl]-2-pyrrolidinecarboxamide,
(5) (2S,4S)—N-(1H-benzotriazol-6-yl)-1-{(2E)-3-[5-chloro-2-(1H-tetrazol-1-yl)phenyl]-2-propenoyl}-4-(4-morpholinyl)-2-pyrrolidinecarboxamide,
(6) 4-[({(2S,4S)-1-{[trans-4-(aminomethyl)cyclohexyl]carbonyl}-4-[4-(cyclopropylsulfonyl)-1-piperazinyl]-2-pyrrolidinyl}carbonyl)amino]benzoic acid,
(7) (2S,4S)-1-{(2E)-3-[5-chloro-2-(1H-tetrazol-1-yl)phenyl]-2-propenoyl}-4-[(3S)-3-methyl-4-sulfamoyl-1-piperazinyl]-N-phenyl-2-pyrrolidinecarboxamide,
(8) methyl [4-(2-{(2S,4R)-1-[(1-carbamimidoyl-4-piperidinyl)carbonyl]-4-[1-(methylsulfonyl)-4-piperidinyl]-2-pyrrolidinyl}-1H-imidazol-5-yl)phenyl]carbamate,
(9) methyl [4-(2-{(2S,4R)-1-(4-carbamimidoylbenzoyl)-4-[1-(methylsulfonyl)-4-piperidinyl]-2-pyrrolidinyl}-1H-imidazol-5-yl)phenyl]carbamate,
(10) methyl [4-(2-{(2S,4R)-1-(4-carbamimidamidobenzoyl)-4-[1-(methylsulfonyl)-4-piperidinyl]-2-pyrrolidinyl}-4-chloro-1H-imidazol-5-yl)phenyl]carbamate,
(11) methyl [4-(2-{(2S,4R)-1-({trans-4-[(1S)-1-aminoethyl] cyclohexyl}carbonyl)-4-[1-(methylsulfonyl)-4-piperidinyl]-2-pyrrolidinyl}-4-chloro-1H-imidazol-5-yl)phenyl] carbamate,
(12) methyl [4-(2-{(2S,4R)-1-[(4-carbamimidoyl-1-piperazinyl)carbonyl]-4-[1-(methylsulfonyl)-4-piperidinyl]-2-pyrrolidinyl}-4-chloro-1H-imidazol-5-yl)phenyl]carbamate,
(13) 4-[({(2S,4R)-1-[(3-chloro-4-fluoro-1-methyl-1H-indol-5-yl)carbonyl]-4-[1-(methylsulfonyl)-4-piperidinyl]-2-pyrrolidinyl}carbonyl)amino]benzoic acid,
(14) methyl [4-(4-chloro-2-{(2S,4R)-1-{(2E)-3-[5-chloro-2-(1H-tetrazol-1-yl)phenyl]-2-propenoyl}-4-[1-(methylsulfonyl)-4-piperidinyl]-2-pyrrolidinyl}-1H-imidazol-5-yl) phenyl]carbamate,
(15) methyl [4-(2-{(2S,4R)-1-{[4-(aminomethyl)cyclohexyl]carbonyl}-4-[1-(methylsulfonyl)-4-piperidinyl]-2-pyrrolidinyl}-4-chloro-1H-imidazol-5-yl)phenyl]carbamate,

(16) methyl [4-(2-{(2S,4S)-1-[(1-carbamimidoyl-4-piperidinyl)carbonyl]-4-[4-(methylsulfonyl)-1-piperazinyl]-2-pyrrolidinyl}-1H-imidazol-5-yl)phenyl]carbamate,
(17) methyl [4-(2-{(2S,4R)-1-[(1-carbamimidoyl-4-piperidinyl)carbonyl]-4-[1-(methylsulfonyl)-4-piperidinyl]-2-pyrrolidinyl}-4-chloro-1H-imidazol-5-yl)phenyl]carbamate,
(18) methyl [4-(2-{(2S,4R)-1-(4-carbamimidoylbenzoyl)-4-[1-(methylsulfonyl)-4-piperidinyl]-2-pyrrolidinyl}-4-chloro-1H-imidazol-5-yl)phenyl]carbamate,
(19) methyl [4-(2-{(2S,4S)-1-(4-carbamimidoylbenzoyl)-4-[4-(methylsulfonyl)-1-piperazinyl]-2-pyrrolidinyl}-1H-imidazol-5-yl)phenyl]carbamate,
(20) methyl [4-(2-{(2S,4S)-1-[(1-carbamimidoyl-4-piperidinyl)carbonyl]-4-[4-(methylsulfonyl)-1-piperazinyl]-2-pyrrolidinyl}-4-chloro-1H-imidazol-5-yl)phenyl]carbamate and
(21) 4-[({(2S,4R)-1-(4-carbamimidoylbenzoyl)-4-[1-(methylsulfonyl)-4-piperidinyl]-2-pyrrolidinyl}carbonyl)amino]benzoic acid.
(20) A pharmaceutical composition which comprises the compound according to any one of (1) to (19), a salt thereof, an N-oxide thereof, a solvate thereof, or a prodrug thereof.
(21) The pharmaceutical composition according to (20), which is a factor XIa inhibitor.
(22) The pharmaceutical composition according to (21), which is an agent for the treatment or prevention of a thromboembolic disease.
(23) The compound according to any one of (1) to (19) for use in treating or preventing a thromboembolic disease.
(24) The compound for use according to (23), wherein the thromboembolic disease is selected from the group consisting of arterial cardiovascular thromboembolic disorders, venous cardiovascular thromboembolic disorders, arterial cerebrovascular thromboembolic disorders, venous cerebrovascular thromboembolic disorders and thromboembolic disorders in the chambers of the heart or in the peripheral circulation.
(25) The compound for use according to (24), wherein the thromboembolic disease is selected from disseminated intravascular coagulopathy (DIC), sepsis, angina, unstable angina, an acute coronary syndrome, coronary artery disease, myocardial infarction, atrial fibrillation, ischemic sudden death, transient ischemic attack, stroke, acute stroke, atherothrombosis, atherosclerosis, peripheral occlusive arterial disease, venous thrombosis, deep vein thrombosis, thrombophlebitis, arterial embolism, coronary arterial thrombosis, cerebral thrombosis, cerebral arterial thrombosis, cerebral embolism, cardiogenic embolism, kidney embolism, portal vein thrombosis, pulmonary embolism, pulmonary infarction, liver embolism, mesenteric artery and/or vein embolism, occlusion of retinal vein and/or artery, systemic embolism, antiphospholipid antibody syndrome, thrombosis resulting from coronary artery bypass graft surgery and thrombosis resulting from medical implants, devices, or procedures in which blood is exposed to an artificial surface that promotes thrombosis.
(26) A method for treating a patient suffering from or susceptible to a thromboembolic disease, which method comprises administering to said patient a therapeutically effective amount of a compound according to any one of (1) to (19).
(27) Use of a compound according to any one of (1) to (19), in the manufacture of a medicament for use in treating or preventing a thromboembolic disease.
(28) The method or use according to (26) or (27), wherein the thromboembolic disease is selected from the group consisting of arterial cardiovascular thromboembolic disorders, venous cardiovascular thromboembolic disorders, arterial cerebrovascular thromboembolic disorders, venous cerebrovascular thromboembolic disorders and thromboembolic disorders in the chambers of the heart or in the peripheral circulation.
(29) The method or use according to (28), wherein the thromboembolic disease is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

DEFINITIONS

As used herein, a C1-4 alkyl group or moiety is a linear or branched alkyl group or moiety containing from 1 to 4 carbon atoms. Examples of C1-4 alkyl groups and moieties include methyl, ethyl, n-propyl, i-propyl, n-butyl, i-butyl, sec-butyl and t-butyl. For the avoidance of doubt, where two alkyl moieties are present in a group, the alkyl moieties may be the same or different.

In the present specification, a C1-4 alkoxy group or moiety is a linear or branched alkoxy group or moiety containing from 1 to 4 carbon atoms. Examples of C1-4 alkoxy groups and moieties include methoxy, ethoxy, n-propoxy, i-propoxy, n-butoxy, i-butoxy, sec-butoxy and t-butoxy. For the avoidance of doubt, where two alkoxy moieties are present in a group, the alkoxy moieties may be the same or different.

In the present specification, the C2-4 alkenyl includes, for example, ethenyl, propenyl, butenyl and isomers thereof.

In the present specification, the C2-4 alkynyl includes, for example, ethynyl, propynyl, butynyl and isomers thereof.

In the present specification, the C1-4 alkylene includes linear or branched alkylene such as methylene, ethylene, propylene, isopropylene, butylenes, and isobutylene.

In the present specification, the C2-4 alkenylene includes linear or branched alkenylene such as vinylene, propenylene, 1- or 2-butenylene, and butadienylene.

In the present specification, the C2-4 alkynylene includes linear or branched alkynylene such as ethynylene, 1- or 2-propynylene and 1- or 2-butynylene.

In the present specification, the halogen atom includes, for example, fluorine, chlorine, bromine and iodine, and is preferably fluorine, chlorine or bromine.

Cyc A, Cyc B, Cyc C, Cyc D and Cyc E each independently represent C3-C8 cycloalkyl, 5- to 10-membered heterocycloalkyl, C6-C10 aryl or 5- to 10-membered heteroaryl.

"C3-C8 cycloalkyl" refers to a C3-C8 cyclic hydrocarbon. Examples of C3-C8 cycloalkyl include cyclopropane, cyclobutane, cyclopentane, cyclohexane, cycloheptane, cyclooctane, cyclobutene, cyclopentene, cyclohexene, cycloheptene, cyclooctene, cyclobutadiene, cyclopentadiene, cyclohexadiene, cycloheptadiene, cyclooctadiene rings and the like. Moreover, the term "C3-C8 cycloalkyl" also includes "C3-C6 cycloalkyl". The term "C3-C6 cycloalkyl" refers to a C3-C6 cyclic hydrocarbon. Examples of C3-C6 cycloalkyl include cyclopropane, cyclobutane, cyclopentane, cyclohexane, cyclobutene, cyclopentene, cyclohexene, cyclobutadiene, cyclopentadiene, cyclohexadiene rings and the like.

"5- to 10-membered heterocycloalkyl" refers to a "5- to 10-membered mono- or bi-non-aromatic heterocyclic ring having 1 to 4 nitrogen atom(s), 1 or 2 oxygen atom(s) and/or 1 or 2 sulfur atom(s) as a hetero atom(s)". Examples of 5- to 10-membered heterocycloalkyl include pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydroxepine, tetrahydroxepine, perhydroxepine, dihydrothiophene, tetrahydrothiophene, dihydrothiopyran, tetrahydrothiopyran, dihydrothiepin, tetrahydrothiepin, perhydrothiepin, dihydroxazole, tetrahydroxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydroxadiazole, tetrahydroxadiazole (oxadiazolidine), dihydroxazine, tetrahydroxazine, dihydroxadiazine, tetrahydroxadiazine, dihydroxazepine, tetrahydroxazepine, perhydroxazepine, dihydroxadiazepine, tetrahydroxadiazepine, perhydroxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, 1,4-dioxane, dithiolane, dithiane, dioxaindane, benzodioxane, chroman, benzodithiolane, benzodithiane, 6,7-dihydro-5H-cyclopenta[b]pyrazine, 5H-cyclopenta[b]pyrazine, 2,4-dihydro-1H-benzo[d][1,3]oxazine rings and the like. Moreover, the term "5- to 10-membered heterocycloalkyl" also includes "5- to 6-membered heterocycloalkyl". The term "5- to 6-membered heterocycloalkyl" refers to a "5- to 6-membered mono-non-aromatic heterocyclic ring having 1 to 3 nitrogen atom(s), 1 or 2 oxygen atom(s) and/or 1 or 2 sulfur atom(s) as a hetero atom(s)". Examples of 5- to 6-membered heterocycloalkyl include pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydroxazole, tetrahydroxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydroxadiazole, tetrahydroxadiazole (oxadiazolidine), dihydroxazine, tetrahydroxazine, dihydroxadiazine, tetrahydroxadiazine, dihydrothiadiazole, tetrahydrothiadiazole (thiadiazolidine), dihydrothiadiazine, tetrahydrothiadiazine, morpholine, thiomorpholine, oxathiane, dioxolane, 1,4-dioxane, dithiolane, dithiane rings and the like.

"C6-C10 aryl" refers to a "C6-10 mono- or bi-aromatic carbocyclic ring". Examples of C6-C10 aryl include benzene, azulene, naphthalene rings and the like. Thus the C6-C10 aryl may be, for example, a phenyl ring and the like.

"5- to 10-membered heteroaryl" refers to a "5- to 10-membered mono- or bi-aromatic heterocyclic ring having 1 to 4 nitrogen atom(s), 1 or 2 oxygen atom(s) and/or 1 or 2 sulfur atom(s) as a hetero atom(s)". Examples of 5- to 10-membered heteroaryl include pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole, isoxazolo[4,5-d]pyridazine rings and the like. Moreover, the term "5- to 10-membered heteroaryl" also includes "5- to 6-membered heteroaryl". The term "5- to 6-membered heteroaryl" refers to a "5- to 6-membered mono-aromatic heterocyclic ring having 1 to 3 nitrogen atom(s), 1 or 2 oxygen atom(s) and/or 1 or 2 sulfur atom(s) as a hetero atom(s)". Examples of 5- to 6-membered heteroaryl include pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole rings and the like.

Cyc D represents C3-C8 cycloalkyl, 5- to 10-membered heterocycloalkyl, C5-C10 aryl or 5- to 10-membered heteroaryl, any of which may be optionally substituted with 1 to 5 $R^8$.

Cyc E represents C3-C8 cycloalkyl, 5- to 10-membered heterocycloalkyl, C5-C10 aryl or 5- to 10-membered heteroaryl, any of which may be optionally substituted with 1 to 5 $R^9$.

The optionally substituted "C3-C8 cycloalkyl" represented by Cyc D or Cyc E may be selected from any of the examples provided above for "C3-C8 cycloalkyl".

The optionally substituted "5- to 10-membered heterocycloalkyl" represented by Cyc D or Cyc E may be selected from any of the examples provided above for "5- to 10-membered heterocycloalkyl".

The optionally substituted "C6-C10 aryl" represented by Cyc D or Cyc E may be selected from any of the examples provided above for "C6-C10 aryl".

The optionally substituted "5- to 10-membered heteroaryl" represented by Cyc D or Cyc E may be selected from any of the examples provided above for "5- to 10-membered heteroaryl".

$R^1$ represents C6-C10 aryl or 5- to 10-membered heteroaryl, any of which may be optionally substituted with 1 to 5 groups selected from halogen, C1-4 alkyl, C1-4 alkoxy, —C1-4 alkylene-C1-4 alkoxy, CN, —COOH, —COO—C1-4 alkyl, —CO—NH$_2$, —OCONH$_2$, —OCONH—C1-4 alkyl, —CONH—C1-4 alkyl, —NHCOO—C1-4 alkyl and —NHCO—C1-4 alkyl.

The optionally substituted "C6-C10 aryl" represented by $R^1$ may be selected from any of the examples provided above for "C6-C10 aryl".

The optionally substituted "5- to 10-membered heteroaryl" represented by $R^1$ may be selected from any of the examples provided above for "5- to 10-membered heteroaryl".

Preferably, Cyc A represents cyclohexyl, phenyl, piperidinyl, piperazinyl or indolyl, more preferably phenyl, cyclohexyl piperidinyl or piperazinyl, and further more preferably phenyl, cyclohexyl or piperidinyl.

Preferably, Cyc B represents C6-C10 aryl or 5- to 10-membered heteroaryl, more preferably phenyl or pyridyl.

Preferably, Cyc C represents 5- to 10-membered heterocycloalkyl, more preferably pyrrolidinyl, piperidinyl piperazinyl or morpholinyl, further more preferably piperidinyl or piperazinyl.

Preferably, Cyc D represents C3-C8 cycloalkyl or C6-C10 aryl, more preferably cyclopropyl or phenyl, any of which may be optionally substituted as set out above.

Preferably, Cyc E represents 5- to 10-membered heteroaryl, more preferably imidazolyl which may be optionally substituted as set out above.

Preferably, each $R^1$ independently represents 5- to 10-membered heteroaryl which may be optionally substituted as set out above, —C(=NH)NH$_2$, —NH—C(=NH)NH$_2$, C1-4 alkyl, —C1-4 alkylene-NH$_2$ or halogen, more preferably tetrazolyl, —C(=NH)NH$_2$, —NH—C(=NH)NH$_2$, —CH$_2$NH$_2$, methyl, chlorine or fluorine.

Preferably, t represents an integer of 0 to 2, more preferably 1 or 2.

Preferably, to represents an integer of 0 or 1, more preferably 0.

Preferably, tB represents an integer of 0 or 1, more preferably 0.

Preferably, each $R^2$ independently represents (1) —COOH, (2) —COO—C1-4 alkyl, (3) —NH$_2$, (4) —NHCOO—C1-4 alkyl, (5) halogen, (6) —SO$_2$—C1-4 alkyl or (7) C1-4 alkoxy, more preferably —COOH, —COOMe, —NH$_2$, —NHCOOMe, chlorine, fluorine, —SO$_2$-Me or methoxy.

Preferably, m represents an integer of 0, 1 or 2, more preferably 1 or 2.

Preferably, each $R^3$ independently represents (1) —COOMe, (2) oxo, (3) —CO-Me, (4) —CO—NH$_2$, (5) —SO$_2$—NH$_2$ or (6) —SO$_2$—R$^6$-R$^7$, more preferably —SO$_2$—R$^6$-R$^7$, wherein $R^6$ is a bond or NH and $R^7$ is preferably C1-4 alkyl or Cyc D, wherein Cyc D is preferably as set out above.

Preferably, n represents an integer of 0 or 1, more preferably 1.

Preferably, nB represents an integer of 0 or 1, more preferably 0.

Preferably, $R^4$ represents a bond or vinylene, more preferably a bond.

Preferably, $R^5$ represents (1) —CONH—, (2) Cyc E or (3) Cyc E substituted by with halogen (preferably chlorine), wherein Cyc E is preferably as set out above.

Preferably, p represents an integer of 0 or 5, more preferably 0 or 1.

In a preferred embodiment, Cyc A represents cyclohexyl, phenyl, piperidinyl, piperazinyl or indolyl, more preferably phenyl, cyclohexyl or piperidinyl, t is 1 and $R^1$ represents —C(=NH)NH$_2$, —NH—C(=NH)NH$_2$ or —C1-4 alkylene-NH$_2$, or t is 2 and one $R^1$ represents tetrazolyl which may be optionally substituted as set out above and the other $R^1$ represents halogen.

In a preferred embodiment, Cyc A represents cyclohexyl, phenyl, piperidinyl, piperazinyl or indolyl, more preferably phenyl, cyclohexyl or piperidinyl, $R^4$ represent a bond and t is 1 and $R^1$ represents —C(=NH)NH$_2$, —NH—C(=NH)NH$_2$ or —C1-4 alkylene-NH$_2$, or $R^4$ represent vinylene and t is 2 and one $R^1$ represents tetrazolyl which may be optionally substituted as set out above and the other $R^1$ represents halogen.

In a preferred embodiment, Cyc B represents C6-C10 aryl or 5- to 10-membered heteroaryl, more preferably phenyl or pyridyl, m is 1 and $R^2$ represents (1) —COOH, (2) —COO—C1-4 alkyl, (3) —NH$_2$, (4) —NHCOO—C1-4 alkyl, (5) halogen, (6) —SO$_2$—C1-4 alkyl or (7) C1-4 alkoxy, more preferably —COOH, —COOMe, —NH$_2$, —NHCOOMe, chlorine, fluorine, —SO$_2$-Me or methoxy.

In a preferred embodiment, Cyc B represents C6-C10 aryl or 5- to 10-membered heteroaryl, more preferably phenyl or pyridyl, $R^5$ represents —CONH— and m is 1 and $R^2$ represents (1) —COOH, (2) —COO—C1-4 alkyl, (3) —NH$_2$, (4) —NHCOO—C1-4 alkyl, (5) halogen, (6) —SO$_2$—C1-4 alkyl or (7) C1-4 alkoxy, more preferably —COOH, —COOMe, —NH$_2$, —NHCOOMe, chlorine, fluorine, —SO$_2$-Me or methoxy, or $R^5$ represents Cyc E or Cyc E substituted with halogen and m is 1 and $R^2$ represents (1) —COOH, (2) —COO—C1-4 alkyl, (3) —NHCOO—C1-4 alkyl, (4) halogen, (5) —SO$_2$—C1-4 alkyl or (6) C1-4 alkoxy, more preferably —COOH, —COOMe, —NHCOOMe, chlorine, fluorine, —SO$_2$-Me or methoxy.

In a preferred embodiment, —Cyc C—$(R^3)_n$ represents

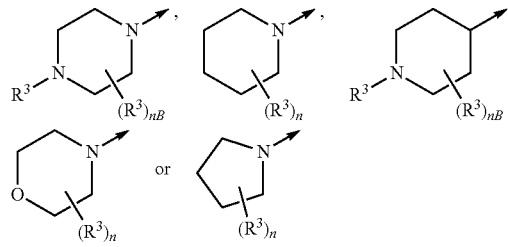

wherein the arrow represents a binding position; and
the other symbols have the same meanings as described above, preferably wherein n is 0, or nB is 0 and $R^3$ represents —SO$_2$—NH$_2$, —SO$_2$—R$^7$ or —SO$_2$—NH—R$^7$.

In a preferred embodiment, —Cyc C—$(R^3)_n$ represents

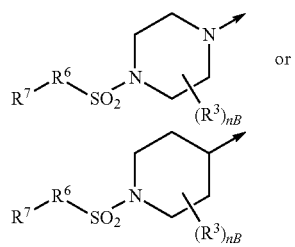

wherein the arrow represents a binding position and
the other symbols have the same meanings as described above, preferably wherein nB is 0 and —SO$_2$—R$^6$—R$^7$ represents —SO$_2$—R$^7$ or —SO$_2$—NH—R$^7$, more preferably nB is 0 and —SO$_2$—R$^6$—R$^7$ represents —SO$_2$—C1-4 alkyl or —SO$_2$-cyclopropyl.

The above preferred embodiments of Cyc A, Cyc B and Cyc C—(R³)ₙ may be included in preferred compound of the invention in any combination.

In one embodiment, preferred compounds of the present invention are pyrrolidine derivatives represented by formula (I-1):

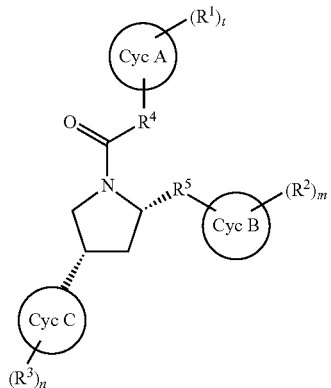

(I-1)

wherein the other symbols have the same meanings as described above.

Preferably Cyc A, Cyc B, Cyc C, R¹, t, R², m, R³ and n in the formula (I-1) are the preferred options as described above.

In one embodiment, preferred compounds of the present invention are pyrrolidine derivatives represented by formula (I-A):

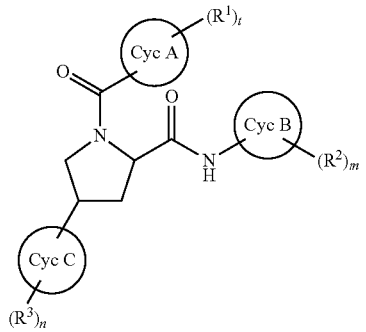

(I-A)

wherein the other symbols have the same meanings as described above. Preferably Cyc A, Cyc B, Cyc C, R¹, t, R², m, R³ and n in the formula (I-A) are the preferred options as described above.

Preferred compounds of formula (I-A) are those in which:
Cyc A represents C3-C8 cycloalkyl or C6-C10 aryl;
Cyc B represents C6-C10 aryl or 5- to 10-membered heteroaryl;
Cyc C represents 5- to 10-membered heterocycloalkyl;
each R¹ independently represents 5- to 10-membered heteroaryl which may be optionally substituted as set out above, —C(=NH)NH₂, —NH—C(=NH)NH₂, C1-4 alkyl, —C1-4 alkylene-NH₂ or halogen;
t represents an integer of 0, 1 or 2;
R² represents (1) —COOH, (2) —COO—C1-4 alkyl, (3) —NH₂, (4) —NHCOO—C1-4 alkyl, (5) halogen, (6) —SO₂—C1-4 alkyl or (7) C1-4 alkoxy;
m represents an integer of 0, 1 or 2;
each R³ independently represents (1) —COO-Me, (2) oxo, (3) —CO-Me, (4) —CO—NH₂, (5) —SO₂—NH₂ or (6) —SO₂—R⁶-R⁷, wherein R⁶ is a bond or NH and R⁷ is preferably C1-4 alkyl or Cyc D, wherein Cyc D is preferably as set out above;
n represents an integer of 0 or 1.

Preferred compounds of formula (I-A) include those in which:
Cyc A represents cyclohexyl, phenyl, piperidinyl or piperazinyl;
Cyc B represents phenyl or pyridyl;
Cyc C represents pyrrolidinyl, piperidinyl, piperazinyl or morpholinyl;
each R¹ independently represents tetrazolyl, —C(=NH)NH₂, —NH—C(=NH)NH₂, —CH₂NH₂, methyl, chlorine or fluorine;
t represents an integer of 1 or 2;
R² represents —COOH, —COOMe, —NH₂, —NHCOOMe, chlorine, fluorine, —SO₂-Me or methoxy;
m represents an integer of 1 or 2;
each R³ independently represents —SO₂—R⁶-R⁷, wherein R⁶ is a bond or NH and R⁷ is preferably C1-4 alkyl, cyclopropyl or phenyl;
n represents an integer of 1.

Further preferred compounds of formula (I-A) include those in which Cyc A represents cyclohexyl, phenyl, piperidinyl, piperazinyl or indolyl, more preferably phenyl, cyclohexyl or piperidinyl and t is 1 and R¹ represents —C(=NH)NH₂, —NH—C(=NH)NH₂ or —CH₂NH₂.

Further preferred compounds of formula (I-A) include those in which Cyc B represents C6-C10 aryl or 5- to 10-membered heteroaryl, more preferably phenyl or pyridyl, and m is 1 and R² represents (1) —COOH, (2) —COO—C1-4 alkyl, (3) —NHCOO—C1-4 alkyl, (4) halogen, (5) —SO₂—C1-4 alkyl or (6) C1-4 alkoxy, more preferably —COOH, —COOMe, —NHCOOMe, chlorine, fluorine, —SO₂-Me.

Further preferred compounds of formula (I-A) include those in which -Cyc C—(R³)ₙ represents

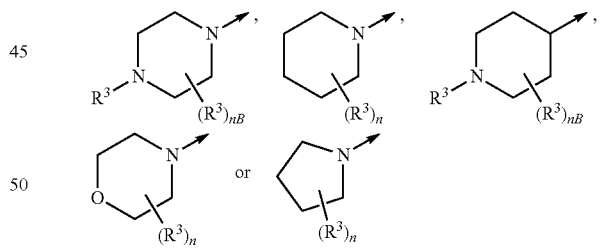

wherein the arrow represents a binding position; and the other symbols have the same meanings as described above, preferably wherein n is 0, or nB is 0 and R³ represents —SO₂—NH₂, —SO₂—R⁷ or —SO₂—NH—R⁷.

Further preferred compounds of formula (I-A) include those in which -Cyc C—(R³)ₙ represents

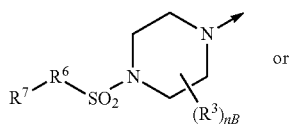

or

-continued

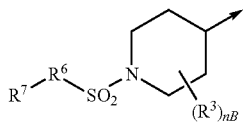

wherein the arrow represents a binding position; and
the other symbols have the same meanings as described above, preferably wherein nB is 0 and —SO₂—R⁶—R⁷ represents —SO₂—R⁷ or —SO₂—NH—R⁷, more preferably nB is 0 and —SO₂—R⁶—R⁷ represents —SO₂—C1-4 alkyl or —SO₂-cyclopropyl.

Further preferred compounds of formula (I-A) include a compound of (I-A-1):

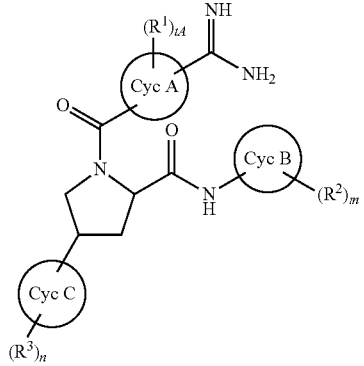
(I-A-1)

wherein to represents an integer of 0 or 1, more preferably 0, and the other symbols have the same meanings as described above and the same preferred definitions as set out above (alone or in any combination), a compound of (I-A-2):

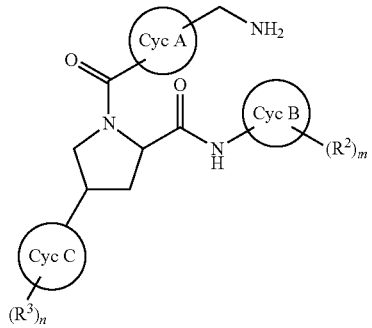
(I-A-2)

wherein all symbols have the same meanings as described above and the same preferred definitions as set out above (alone or in any combination), a compound of (I-A-3):

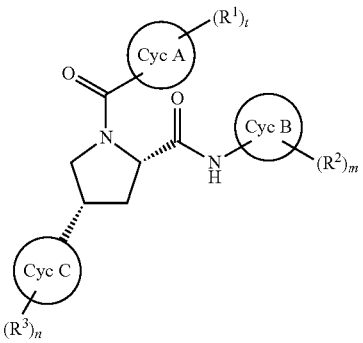
(I-A-3)

wherein all symbols have the same meanings as described above and the same preferred definitions as set out above (alone or in any combination), a compound of (I-A-4):

(I-A-4)

wherein all symbols have the same meanings as described above and the same preferred definitions as set out above (alone or in any combination), a compound of (I-A-5):

(I-A-5)

wherein all symbols have the same meanings as described above and the same preferred definitions as set out above (alone or in any combination), a compound of (I-A-6):

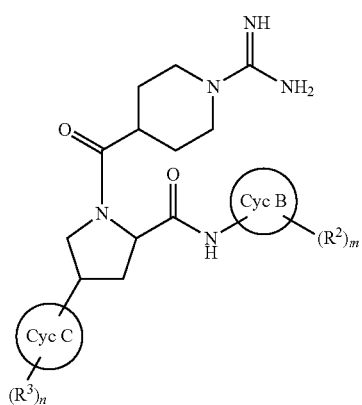
(I-A-6)

wherein all symbols have the same meanings as described above and the same preferred definitions as set out above (alone or in any combination), a compound of (I-A-7):

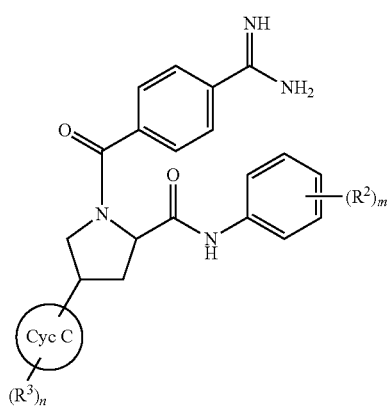
(I-A-7)

wherein all symbols have the same meanings as described above and the same preferred definitions as set out above (alone or in any combination), a compound of (I-A-8):

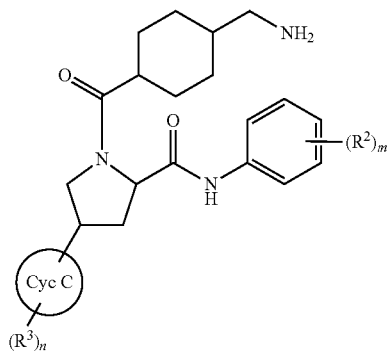
(I-A-8)

wherein all symbols have the same meanings as described above and the same preferred definitions as set out above (alone or in any combination), a compound of (I-A-9):

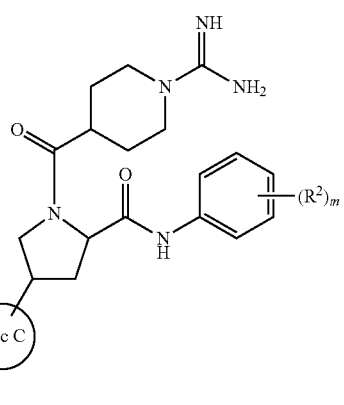
(I-A-9)

wherein all symbols have the same meanings as described above and the same preferred definitions as set out above (alone or in any combination), a compound of (I-A-10):

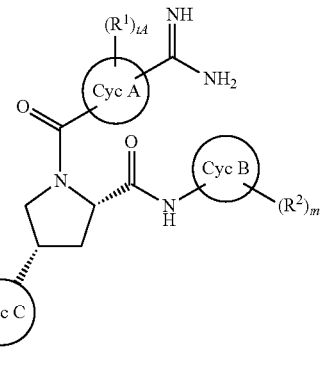
(I-A-10)

wherein all symbols have the same meanings as described above and the same preferred definitions as set out above (alone or in any combination), a compound of (I-A-11):

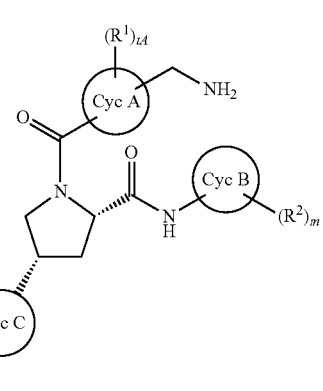
(I-A-11)

wherein all symbols have the same meanings as described above and the same preferred definitions as set out above (alone or in any combination), and the like.

In another embodiment, preferred compounds of the present invention are pyridinone derivatives represented by formula (I-B):

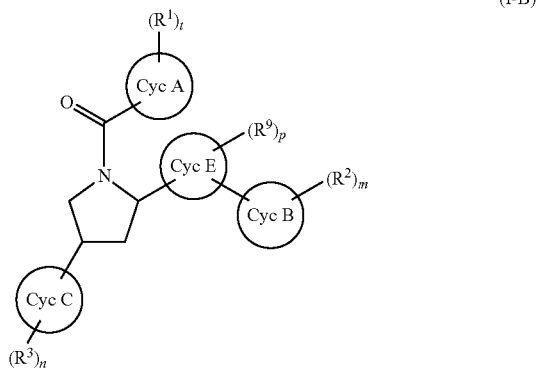

(I-B)

wherein the other symbols have the same meanings as described above. Preferably, Cyc A, Cyc B, Cyc C, Cyc E, $R^1$, t, $R^2$, m, $R^3$, n, $R^9$ and p in the formula (I-B) are the preferred options as described above.

Preferred compounds of formula (I-B) are those in which:

Cyc A represents C3-C8 cycloalkyl or C6-C10 aryl;

Cyc B represents C6-C10 aryl or 5- to 10-membered heteroaryl;

Cyc C represents 5- to 10-membered heterocycloalkyl;

Cyc E represents 5- to 10-membered heteroaryl;

each $R^1$ independently represents 5- to 10-membered heteroaryl which may be optionally substituted as set out above, —C(=NH)NH$_2$, —NH—C(=NH)NH$_2$, C1-4 alkyl, —C1-4 alkylene-NH$_2$ or halogen;

t represents an integer of 0, 1 or 2;

each $R^2$ represents (1) —COOH, (2) —COO—C1-4 alkyl, (3) —NH$_2$, (4) —NHCOO—C1-4 alkyl, (5) halogen, (6) —SO$_2$—C1-4 alkyl or (7) C1-4 alkoxy;

m represents an integer of 0, 1 or 2;

each $R^3$ independently represents (1) —COO-Me, (2) oxo, (3) —CO-Me, (4) —CO—NH$_2$, (5) —SO$_2$—NH$_2$ or (6) —SO$_2$—$R^6$-$R^7$, wherein $R^6$ is a bond or NH and $R^7$ is preferably C1-4 alkyl or Cyc D, wherein Cyc D is preferably as set out above;

n represents an integer of 0 or 1;

each $R^9$ represents halogen;

p represents an integer of 0 or 1.

Preferred compounds of formula (I-B) include those in which:

Cyc A represents cyclohexyl, phenyl, piperidinyl or piperazinyl;

Cyc B represents phenyl or pyridyl;

Cyc C represents pyrrolidinyl, piperidinyl, piperazinyl or morpholinyl;

Cyc E represents imidazolyl;

each $R^1$ independently represents tetrazolyl, —C(=NH)NH$_2$, —NH—C(=NH)NH$_2$, —CH$_2$NH$_2$, methyl, chlorine or fluorine;

t represents an integer of 1 or 2;

$R^2$ represents —COOH, —COOMe, —NH$_2$, —NHCOOMe, chlorine, fluorine, —SO$_2$-Me or methoxy;

m represents an integer of 1 or 2;

each $R^3$ independently represents —SO$_2$—$R^6$-$R^7$, wherein $R^6$ is a bond or NH and $R^7$ is preferably C1-4 alkyl, cyclopropyl or phenyl;

n represents an integer of 1;

each $R^9$ represents chlorine;

p represents an integer of 0 or 1.

Further preferred compounds of formula (I-B) include those in which Cyc A represents cyclohexyl, phenyl, piperidinyl, piperazinyl or indolyl, more preferably phenyl, cyclohexyl or piperidinyl and t is 1 and $R^1$ represents —C(=NH)NH$_2$, —NH—C(=NH)NH$_2$, or —CH$_2$NH$_2$.

Further preferred compounds of formula (I-B) include those in which Cyc B represents C6-C10 aryl or 5- to 10-membered heteroaryl, more preferably phenyl or pyridyl, and m is 1 and $R^2$ represents (1) —COOH, (2) —COO—C1-4 alkyl, (3) —NH$_2$, (4) —NHCOO—C1-4 alkyl, (5) halogen, (6) —SO$_2$—C1-4 alkyl or (7) C1-4 alkoxy, more preferably —COOH, —COOMe, —NH$_2$, —NHCOOMe, chlorine, fluorine, —SO$_2$-Me.

Further preferred compounds of formula (I-B) include those in which -Cyc C—$(R^3)_n$ represents

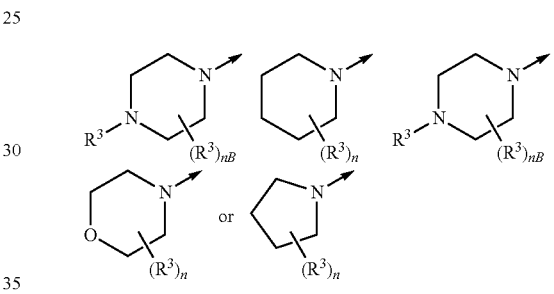

wherein the arrow represents a binding position; and the other symbols have the same meanings as described above, preferably wherein n is 0, or nB is 0 and $R^3$ represents —SO$_2$—NH$_2$, —SO$_2$—$R^7$ or —SO$_2$—NH—$R^7$.

Further preferred compounds of formula (I-B) include those in which -Cyc C—$(R^3)_n$ represents

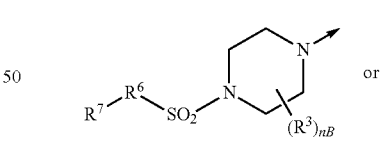

or

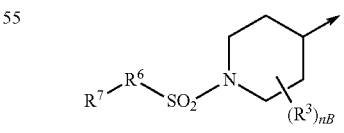

wherein the arrow represents a binding position; and the other symbols have the same meanings as described above, preferably wherein nB is 0 and —SO$_2$—$R^6$—$R^7$ represents —SO$_2$—$R^7$ or —SO$_2$—NH—$R^7$, more preferably nB is 0 and —SO$_2$—$R^6$—$R^7$ represents —SO$_2$—C1-4 alkyl or —SO$_2$-cyclopropyl Further preferred compounds of formula (I-B) include a compound of (I-B-1):

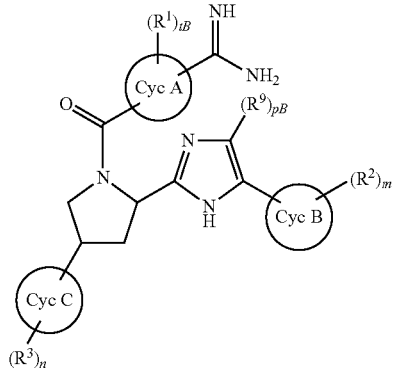

(I-B-1)

wherein tB represents an integer of 0 or 1, more preferably 0, pB represents an integer of 0 or 1, more preferably 0, and the other symbols have the same meanings as described above and the same preferred definitions as set out above (alone or in any combination), a compound of (I-B-2):

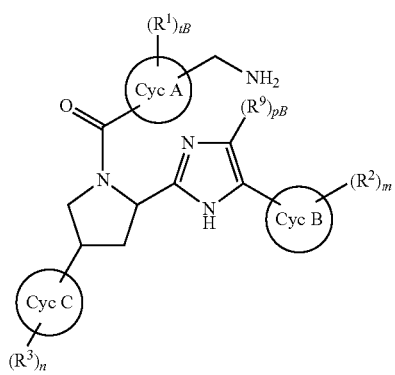

(I-B-2)

wherein all symbols have the same meanings as described above and the same preferred definitions as set out above (alone or in any combination), a compound of (I-B-3):

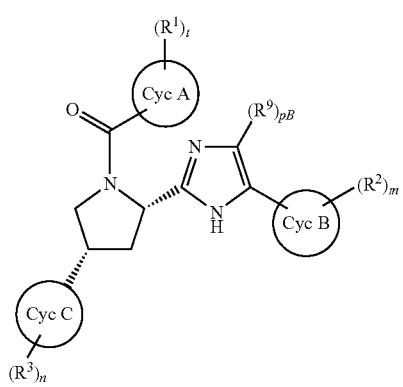

(I-B-3)

wherein all symbols have the same meanings as described above and the same preferred definitions as set out above (alone or in any combination), a compound of (I-B-4):

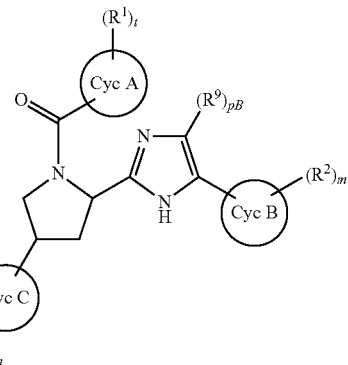

(I-B-4)

wherein all symbols have the same meanings as described above and the same preferred definitions as set out above (alone or in any combination), a compound of (I-B-5):

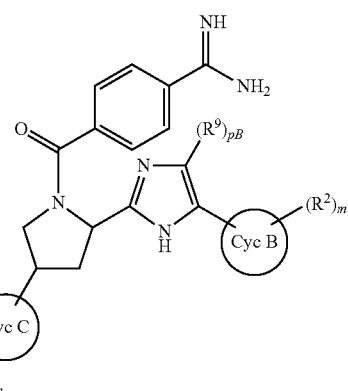

(I-B-5)

wherein all symbols have the same meanings as described above and the same preferred definitions as set out above (alone or in any combination), a compound of (I-B-6):

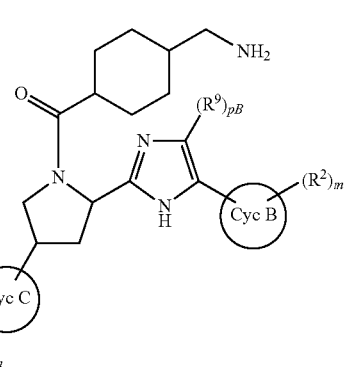

(I-B-6)

wherein all symbols have the same meanings as described above and the same preferred definitions as set out above (alone or in any combination), a compound of (I-B-7):

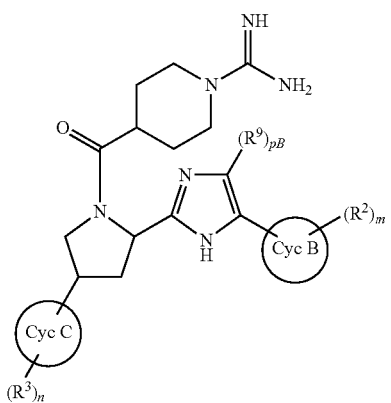
(I-B-7)

wherein all symbols have the same meanings as described above and the same preferred definitions as set out above (alone or in any combination), a compound of (I-B-8):

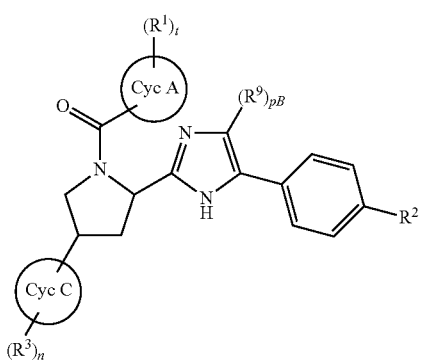
(I-B-8)

wherein all symbols have the same meanings as described above and the same preferred definitions as set out above (alone or in any combination), a compound of (I-B-9):

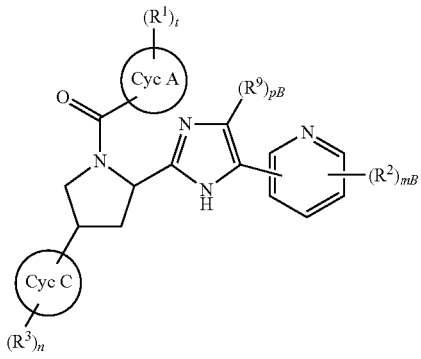
(I-B-9)

wherein mB represents an integer of 0 to 4, more preferably 0 or 1, and the other symbols have the same meanings as described above and the same preferred definitions as set out above (alone or in any combination), a compound of (I-B-10):

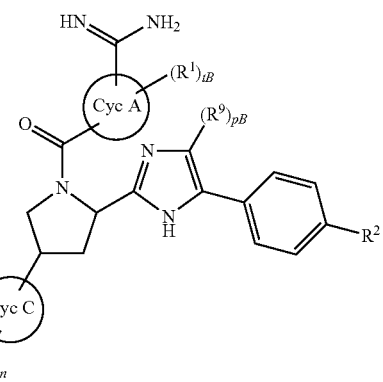
(I-B-10)

wherein all symbols have the same meanings as described above and the same preferred definitions as set out above (alone or in any combination), a compound of (I-B-11):

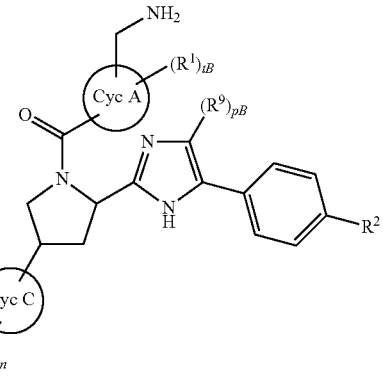
(I-B-11)

wherein all symbols have the same meanings as described above and the same preferred definitions as set out above (alone or in any combination), a compound of (I-B-12):

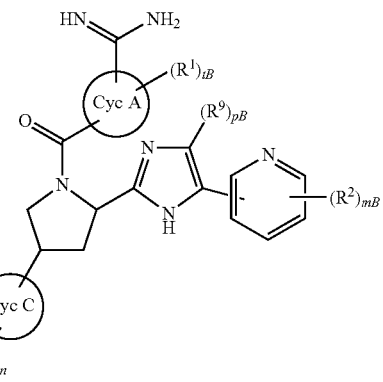
(I-B-12)

wherein all symbols have the same meanings as described above and the same preferred definitions as set out above (alone or in any combination), a compound of (I-B-13):

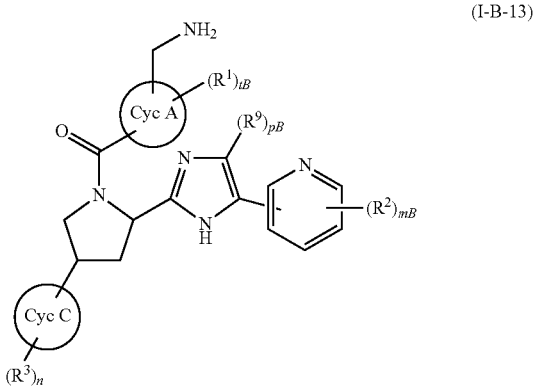

(I-B-13)

wherein all symbols have the same meanings as described above and the same preferred definitions as set out above (alone or in any combination), and the like.

In another embodiment, preferred compounds of the present invention are pyridinone derivatives represented by formula (I-C):

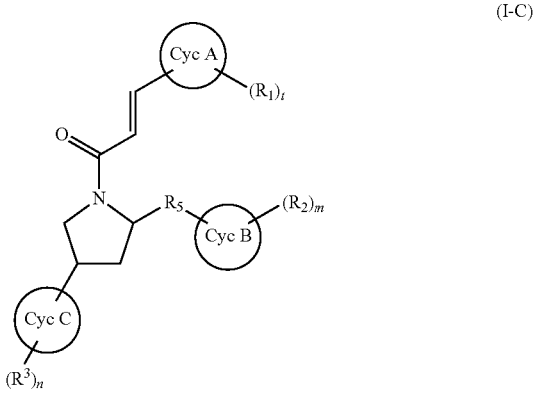

(I-C)

wherein the other symbols have the same meanings as described above. Preferably, Cyc A, Cyc B, Cyc C, $R^1$, t, $R^2$, m, $R^3$, n and $R^5$ in the formula (I-C) are the preferred options as described above.

Preferred compounds of formula (I-C) are those in which:

Cyc A represents C3-C8 cycloalkyl or C6-C10 aryl;

Cyc B represents C6-C10 aryl or 5- to 10-membered heteroaryl;

Cyc C represents 5- to 10-membered heterocycloalkyl;

each $R^1$ independently represents 5- to 10-membered heteroaryl which may be optionally substituted as set out above, —C(=NH)NH$_2$, —NH—C(=NH)NH$_2$, C1-4 alkyl, —C1-4 alkylene-NH$_2$ or halogen;

t represents an integer of 0, 1 or 2;

each $R^2$ represents (1) —COOH, (2) —COO—C1-4 alkyl, (3) —NH$_2$, (4) —NHCOO—C1-4 alkyl, (5) halogen, (6) —SO$_2$—C1-4 alkyl or (7) C1-4 alkoxy;

m represents an integer of 0, 1 or 2;

each $R^3$ independently represents (1) —COO-Me, (2) oxo, (3) —CO-Me, (4) —CO—NH$_2$, (5) —SO$_2$—NH$_2$ or (6) —SO$_2$—$R^6$-$R^7$, wherein $R^6$ is a bond or NH and $R^7$ is preferably C1-4 alkyl or Cyc D, wherein Cyc D is preferably as set out above;

n represents an integer of 0 or 1;

$R^5$ represents (1) —CONH—, (2) Cyc E or (3) Cyc E substituted by with halogen.

Preferred compounds of formula (I-C) include those in which:

Cyc A represents cyclohexyl, phenyl, piperidinyl or piperazinyl;

Cyc B represents phenyl or pyridyl;

Cyc C represents pyrrolidinyl, piperidinyl, piperazinyl or morpholinyl;

each $R^1$ independently represents tetrazolyl, —C(=NH)NH$_2$, —NH—C(=NH)NH$_2$, —CH$_2$NH$_2$, methyl, chlorine or fluorine;

t represents an integer of 1 or 2;

$R^2$ represents —COOH, —COOMe, —NH$_2$, —NHCOOMe, chlorine, fluorine, —SO$_2$-Me or methoxy;

m represents an integer of 1 or 2;

each $R^3$ independently represents —SO$_2$—$R^6$-$R^7$, wherein $R^6$ is a bond or NH and $R^7$ is preferably C1-4 alkyl, cyclopropyl or phenyl;

n represents an integer of 1;

$R^5$ represents (1) —CONH—, (2) imidazolyl or (3) imidazolyl substituted by with chlorine.

Further preferred compounds of formula (I-C) include those in which Cyc A represents cyclohexyl, phenyl, piperidinyl, piperazinyl or indolyl, more preferably phenyl, t is 2 and one $R^1$ represents tetrazolyl which may be optionally substituted as set out above and the other $R^1$ represents halogen.

Further preferred compounds of formula (I-C) include those in which Cyc B represents C6-C10 aryl or 5- to 10-membered heteroaryl, more preferably phenyl, and m is 1 and $R^2$ represents (1) —COOH, (2) —COO—C1-4 alkyl, (3) —NH$_2$, (4) —NHCOO—C1-4 alkyl, (5) halogen, (6) —SO$_2$—C1-4 alkyl or (7) C1-4 alkoxy, more preferably —COOH, —COOMe, —NHCOOMe, chlorine, fluorine, —SO$_2$-Me or methoxy.

Further preferred compounds of formula (I-C) include those in which -Cyc C—($R^3$)$_n$ represents

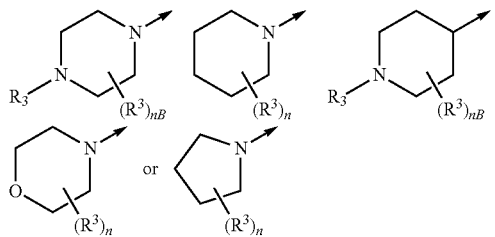

wherein the arrow represents a binding position and the other symbols have the same meanings as described above, preferably wherein n is 0 or nB is 0 and $R^3$ represents —SO$_2$—NH$_2$, —SO$_2$—$R^7$ or —SO$_2$—NH—$R^7$.

Further preferred compounds of formula (I-C) include those in which -Cyc C—($R^3$)$_n$ represents

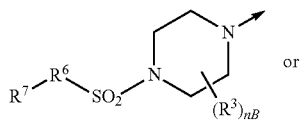

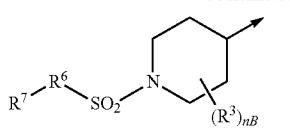

wherein the arrow represents a binding position; and the other symbols have the same meanings as described above, preferably wherein nB is 0 and —SO$_2$—R$^6$—R$^7$ represents —SO$_2$—R$^7$ or —SO$_2$—NH—R$^7$, more preferably nB is 0 and —SO$_2$—R$^6$—R$^7$ represents —SO$_2$—C1-4 alkyl or —SO$_2$-cyclopropyl.

Further preferred compounds of formula (I-C) include a compound of (I-C-1):

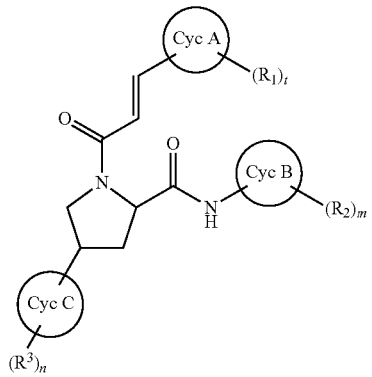

(I-C-1)

wherein all symbols have the same meanings as described above and the same preferred definitions as set out above (alone or in any combination), a compound of (I-C-2):

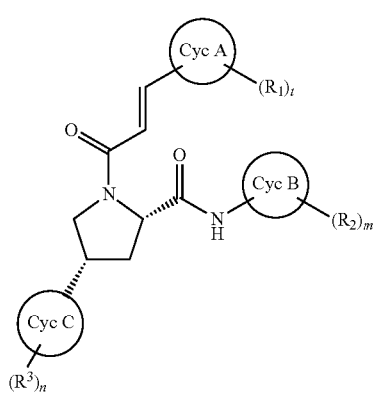

(I-C-2)

wherein all symbols have the same meanings as described above and the same preferred definitions as set out above (alone or in any combination), a compound of (I-C-3):

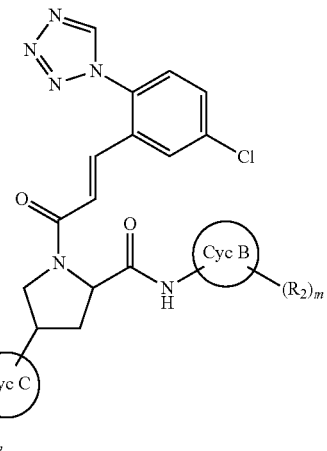

(I-C-3)

wherein all symbols have the same meanings as described above and the same preferred definitions as set out above (alone or in any combination), a compound of (I-C-4):

(I-C-4)

wherein all symbols have the same meanings as described above and the same preferred definitions as set out above (alone or in any combination), and the like.

As used herein, general references to "compounds of formula (I)" include compounds of formula (I-A), (I-B) and (I-C).

Particularly preferred compounds of formula (I-A) include:

4-[({(2S,4S)-1-[(1-carbamimidoyl-4-piperidinyl)carbonyl]-4-[4-(methylsulfonyl)-1-piperazinyl]-2-pyrrolidinyl}carbonyl)amino]benzoic acid, 4-[({(2S,4S)-1-(4-carbamimidamidobenzoyl)-4-[4-(methylsulfonyl)-1-piperazinyl]-2-pyrrolidinyl}carbonyl)amino]benzoic acid, 4-[({(2S,4S)-1-(4-carbamimidoylbenzoyl)-4-[4-(methylsulfonyl)-1-piperazinyl]-2-pyrrolidinyl}carbonyl)amino]benzoic acid, 4-[({(2S,4S)-1-{[cis-4-(aminomethyl)cyclohexyl]carbonyl}-4-[4-(methylsulfonyl)-1-piperazinyl]-2-pyrrolidinyl}carbonyl)amino]benzoic acid, 4-[({(2S,4S)-1-({trans-4-[(1S)-1-aminoethyl]cyclohexyl}carbonyl)-4-[4-(methylsulfonyl)-1-piperazinyl]-2-pyrrolidinyl}carbonyl)amino]benzoic acid, 4-[({(2S,4S)-1-[(trans-4-carbamimidoylcyclohexyl)carbonyl]-4-[4-(methylsulfonyl)-1-piperazinyl]-2-pyrrolidinyl}carbonyl)amino]benzoic acid,
4-[({(2S,4R)-1-[(3-chloro-4-fluoro-1-methyl-1H-indol-5-yl)carbonyl]-4-[1-(methylsulfonyl)-4-piperidinyl]-2-pyrrolidinyl}carbonyl)amino]benzoic acid,
4-({[(2S,4S)-1-{[trans-4-(aminomethyl)cyclohexyl]carbonyl}-4-(4-morpholinyl)-2-pyrrolidinyl]carbonyl}amino)benzoic acid,
4-({[(3'S,5'S)-1'-{[trans-4-(aminomethyl)cyclohexyl]carbonyl}-1,3'-bipyrrolidin-5'-yl]carbonyl}amino)benzoic acid,
4-({[(2S,4S)-1-{[trans-4-(aminomethyl)cyclohexyl]carbonyl}-4-(1-piperidinyl)-2-pyrrolidinyl]carbonyl}amino)benzoic acid,
4-[({(2S,4S)-1-{[trans-4-(aminomethyl)cyclohexyl]carbonyl}-4-[4-(methylsulfonyl)-1-piperazinyl]-2-pyrrolidinyl}carbonyl)amino]benzoic acid,
4-[({(2S,4S)-1-{[trans-4-(aminomethyl)cyclohexyl]carbonyl}-4-[4-(methoxycarbonyl)-1-piperazinyl]-2-pyrrolidinyl}carbonyl)amino]benzoic acid,
4-({[(2S,4S)-4-(4-acetyl-1-piperazinyl)-1-{[trans-4-(aminomethyl)cyclohexyl]carbonyl}-2-pyrrolidinyl]carbonyl}amino)benzoic acid,
4-({[(2S,4S)-1-{[trans-4-(aminomethyl)cyclohexyl]carbonyl}-4-(4-carbamoyl-1-piperazinyl)-2-pyrrolidinyl]carbonyl}amino)benzoic acid,
4-({[(2S,4S)-1-{[trans-4-(aminomethyl)cyclohexyl]carbonyl}-4-(3-oxo-1-piperazinyl)-2-pyrrolidinyl]carbonyl}amino)benzoic acid,
(2S,4S)-1-[(3-chloro-1H-indol-5-yl)carbonyl]-4-[4-(cyclopropylsulfonyl)-1-piperazinyl]-N-phenyl-2-pyrrolidinecarboxamide,
4-[({(2S,4S)-1-{[trans-4-(aminomethyl)cyclohexyl]carbonyl}-4-[4-(cyclopropylsulfonyl)-1-piperazinyl]-2-pyrrolidinyl}carbonyl)amino]benzoic acid,
4-[({(2S,4S)-1-{[4-(aminomethyl)-1-piperidinyl]carbonyl}-4-[4-(methylsulfonyl)-1-piperazinyl]-2-pyrrolidinyl}carbonyl)amino]benzoic acid,
4-[({(2S,4S)-1-[(4-carbamimidoyl-1-piperazinyl)carbonyl]-4-[4-(methylsulfonyl)-1-piperazinyl]-2-pyrrolidinyl}carbonyl)amino]benzoic acid,
4-[({(2S,4S)-1-{[trans-4-(aminomethyl)cyclohexyl]carbonyl}-4-[4-(ethylsulfonyl)-1-piperazinyl]-2-pyrrolidinyl}carbonyl)amino]benzoic acid,
4-[({(2S,4R)-1-[(1-carbamimidoyl-4-piperidinyl)carbonyl]-4-[1-(methylsulfonyl)-4-piperidinyl]-2-pyrrolidinyl}carbonyl)amino]benzoic acid,
4-[({(2S,4R)-1-(4-carbamimidoylbenzoyl)-4-[1-(methylsulfonyl)-4-piperidinyl]-2-pyrrolidinyl}carbonyl)amino]benzoic acid,
benzyl 4-[({(2S,4S)-1-(4-{N'-[(benzyloxy)carbonyl]carbamimidoyl}benzoyl)-4-[4-(methylsulfonyl)-1-piperazinyl]-2-pyrrolidinyl}carbonyl)amino]benzoate,
ethyl 4-[({(2S,4S)-1-(4-carbamimidoylbenzoyl)-4-[4-(methylsulfonyl)-1-piperazinyl]-2-pyrrolidinyl}carbonyl)amino]benzoate,
benzyl 4-[({(2S,4S)-1-(4-cyanobenzoyl)-4-[4-(methylsulfonyl)-1-piperazinyl]-2-pyrrolidinyl}carbonyl)amino]benzoate and
benzyl 4-[({(2S,4S)-1-[4-(N'-hydroxycarbamimidoyl)benzoyl]-4-[4-(methylsulfonyl)-1-piperazinyl]-2-pyrrolidinyl}carbonyl)amino]benzoate
salts thereof, N-oxides thereof, solvates thereof, and prodrugs thereof.

Particularly preferred compounds of formula (I-B) include:
methyl [4-(2-{(2S,4R)-1-[(1-carbamimidoyl-4-piperidinyl)carbonyl]-4-[1-(methylsulfonyl)-4-piperidinyl]-2-pyrrolidinyl}-4-chloro-1H-imidazol-5-yl)phenyl]carbamate,
methyl [4-(2-{(2S,4R)-1-(4-carbamimidoylbenzoyl)-4-[1-(methylsulfonyl)-4-piperidinyl]-2-pyrrolidinyl}-4-chloro-1H-imidazol-5-yl)phenyl]carbamate,
methyl [4-(2-{(2S,4R)-1-[(1-carbamimidoyl-4-piperidinyl)carbonyl]-4-[1-(methylsulfonyl)-4-piperidinyl]-2-pyrrolidinyl}-1H-imidazol-5-yl)phenyl]carbamate,
methyl [4-(2-{(2S,4R)-1-(4-carbamimidoylbenzoyl)-4-[1-(methylsulfonyl)-4-piperidinyl]-2-pyrrolidinyl}-1H-imidazol-5-yl)phenyl]carbamate,
methyl [4-(2-{(2S,4R)-1-{[cis-4-(aminomethyl)cyclohexyl]carbonyl}-4-[1-(methylsulfonyl)-4-piperidinyl]-2-pyrrolidinyl}-4-chloro-1H-imidazol-5-yl)phenyl]carbamate,
methyl [4-(2-{(2S,4R)-1-[(4-carbamimidoyl-1-piperazinyl)carbonyl]-4-[1-(methylsulfonyl)-4-piperidinyl]-2-pyrrolidinyl}-4-chloro-1H-imidazol-5-yl)phenyl]carbamate,
methyl [4-(2-{(2S,4R)-1-(4-carbamimidamidobenzoyl)-4-[1-(methylsulfonyl)-4-piperidinyl]-2-pyrrolidinyl}-1H-imidazol-5-yl)phenyl]carbamate,
methyl [4-(2-{(2S,4R)-1-(4-carbamimidamidobenzoyl)-4-[1-(methylsulfonyl)-4-piperidinyl]-2-pyrrolidinyl}-4-chloro-1H-imidazol-5-yl)phenyl]carbamate,
methyl [4-(2-{(2S,4R)-1-({trans-4-[(1S)-1-aminoethyl]cyclohexyl}carbonyl)-4-[1-(methylsulfonyl)-4-piperidinyl]-2-pyrrolidinyl}-1H-imidazol-5-yl)phenyl]carbamate,
methyl [4-(4-chloro-2-{(2S,4R)-1-({4-[(methylamino)methyl]cyclohexyl}carbonyl)-4-[1-(methylsulfonyl)-4-piperidinyl]-2-pyrrolidinyl}-1H-imidazol-5-yl)phenyl]carbamate,
methyl [4-(2-{(2S,4R)-1-({trans-4-[(1S)-1-aminoethyl]cyclohexyl}carbonyl)-4-[1-(methylsulfonyl)-4-piperidinyl]-2-pyrrolidinyl}-4-chloro-1H-imidazol-5-yl)phenyl]carbamate,
methyl [4-(2-{(2S,4S)-1-(4-carbamimidoylbenzoyl)-4-[4-(methylsulfonyl)-1-piperazinyl]-2-pyrrolidinyl}-1H-imidazol-5-yl)phenyl]carbamate,
methyl [4-(2-{(2S,4S)-1-[(1-carbamimidoyl-4-piperidinyl)carbonyl]-4-[4-(methylsulfonyl)-1-piperazinyl]-2-pyrrolidinyl}-1H-imidazol-5-yl)phenyl]carbamate,
methyl [4-(2-{(2S,4S)-1-[(1-carbamimidoyl-4-piperidinyl)carbonyl]-4-[4-(methylsulfonyl)-1-piperazinyl]-2-pyrrolidinyl}-4-chloro-1H-imidazol-5-yl)phenyl]carbamate,
(3-chloro-4-fluoro-1-methyl-1H-indol-5-yl)[(2S,4S)-2-(4-chloro-5-phenyl-1H-imidazol-2-yl)-4-(4-morpholinyl)-1-pyrrolidinyl]methanone,
methyl [4-(4-chloro-2-{(2S,4R)-1-[(3-chloro-4-fluoro-1-methyl-1H-indol-5-yl)carbonyl]-4-[1-(methylsulfonyl)-4-piperidinyl]-2-pyrrolidinyl}-1H-imidazol-5-yl)phenyl]carbamate,
methyl [4-(2-{(2S,4R)-1-{[4-(aminomethyl)cyclohexyl]carbonyl}-4-[1-(methylsulfonyl)-4-piperidinyl]-2-pyrrolidinyl}-4-chloro-1H-imidazol-5-yl)phenyl]carbamate,
(2E)-3-[5-chloro-2-(1H-tetrazol-1-yl)phenyl]-1-[(2S,4S)-4-(4-morpholinyl)-2-(5-phenyl-1H-imidazol-2-yl)-1-pyrrolidinyl]-2-propen-1-one,
methyl [4-(2-{(2S,4R)-1-{[4-(aminomethyl)-1-piperidinyl]carbonyl}-4-[1-(methylsulfonyl)-4-piperidinyl]-2-pyrrolidinyl}-4-chloro-1H-imidazol-5-yl)phenyl]carbamate,
(2E)-1-[(2S,4S)-2-(4-chloro-5-phenyl-1H-imidazol-2-yl)-4-(4-morpholinyl)-1-pyrrolidinyl]-3-[5-chloro-2-(1H-tetrazol-1-yl)phenyl]-2-propen-1-one and 4-[(2S,4R)-2-[5-(6-amino-3-pyridyl)-1H-imidazol-2-yl]-4-(1-methylsulfonyl-4-piperidyl)pyrrolidine-1-carbonyl]piperidine-1-carboxamidine, salts thereof, N-oxides thereof, solvates thereof, and prodrugs thereof.

Particularly preferred compounds of formula (I-C) include:

4-[({(2S,4R)-1-{(2E)-3-[5-chloro-2-(1H-tetrazol-1-yl)phenyl]-2-propenoyl}-4-[1-(methylsulfonyl)-4-piperidinyl]-2-pyrrolidinyl}carbonyl)amino]benzoic acid, methyl [4-(4-chloro-2-{(2S,4R)-1-{(2E)-3-[5-chloro-2-(1H-tetrazol-1-yl)phenyl]-2-propenoyl}-4-[1-(methylsulfonyl)-4-piperidinyl]-2-pyrrolidinyl}-1H-imidazol-5-yl)phenyl]carbamate, methyl 4-({[(2S,4S)-1-{(2E)-3-[5-chloro-2-(1H-tetrazol-1-yl)phenyl]-2-propenoyl}-4-(4-morpholinyl)-2-pyrrolidinyl]carbonyl}amino)benzoate, 4-({[(2S,4S)-1-{(2E)-3-[5-chloro-2-(1H-tetrazol-1-yl)phenyl]-2-propenoyl}-4-(4-morpholinyl)-2-pyrrolidinyl]carbonyl}amino)benzoic acid, (2S,4S)-1-{(2E)-3-[5-chloro-2-(1H-tetrazol-1-yl)phenyl]-2-propenoyl}-N-phenyl-4-(4-sulfamoyl-1-piperazinyl)-2-pyrrolidinecarboxamide, (2S,4S)-1-{(2E)-3-[5-chloro-2-(1H-tetrazol-1-yl)phenyl]-2-propenoyl}-N-phenyl-4-[4-(phenylsulfonyl)-1-piperazinyl]-2-pyrrolidinecarboxamide, (2S,4S)-1-{(2E)-3-[5-chloro-2-(1H-tetrazol-1-yl)phenyl]-2-propenoyl}-N-[4-(methylsulfonyl)phenyl]-4-(4-morpholinyl)-2-pyrrolidinecarboxamide, (2S,4S)-1-{(2E)-3-[5-chloro-2-(1H-tetrazol-1-yl)phenyl]-2-propenoyl}-4-(4-morpholinyl)-N-(3-pyridinyl)-2-pyrrolidinecarboxamide, (2S,4S)-1-{(2E)-3-[5-chloro-2-(1H-tetrazol-1-yl)phenyl]-2-propenoyl}-4-[(3S)-3-methyl-4-sulfamoyl-1-piperazinyl]-N-phenyl-2-pyrrolidinecarboxamide, (2S,4S)-1-{(2E)-3-[5-chloro-2-(1H-tetrazol-1-yl)phenyl]-2-propenoyl}-N-(4-methoxyphenyl)-4-(4-morpholinyl)-2-pyrrolidinecarboxamide, (3R,3'S,5'S)-1'-{(2E)-3-[5-chloro-2-(1H-tetrazol-1-yl)phenyl]-2-propenoyl}-N-phenyl-3-(sulfamoylamino)-1,3'-bipyrrolidine-5'-carboxamide, (2S,4S)—N-(1H-benzotriazol-6-yl)-1-{(2E)-3-[5-chloro-2-(1H-tetrazol-1-yl)phenyl]-2-propenoyl}-4-(4-morpholinyl)-2-pyrrolidinecarboxamide, (2S,4S)—N-(3-chlorophenyl)-1-{(2E)-3-[5-chloro-2-(1H-tetrazol-1-yl)phenyl]-2-propenoyl}-4-(4-morpholinyl)-2-pyrrolidinecarboxamide, (2E)-3-[5-chloro-2-(1H-tetrazol-1-yl)phenyl]-1-[(2S,4S)-4-(4-morpholinyl)-2-(5-phenyl-1H-imidazol-2-yl)-1-pyrrolidinyl]-2-propen-1-one, (2E)-1-[(2S,4S)-2-(4-chloro-5-phenyl-1H-imidazol-2-yl)-4-(4-morpholinyl)-1-pyrrolidinyl]-3-[5-chloro-2-(1H-tetrazol-1-yl)phenyl]-2-propen-1-one, (2S,4S)—N-(3-chloro-4-fluorophenyl)-1-{(2E)-3-[5-chloro-2-(1H-tetrazol-1-yl)phenyl]-2-propenoyl}-4-(4-morpholinyl)-2-pyrrolidinecarboxamide, and (2S,4S)-1-{(2E)-3-[5-chloro-2-(1H-tetrazol-1-yl)phenyl]-2-propenoyl}-4-(4-morpholinyl)-N-(2-oxo-2,3-dihydro-1H-benzimidazol-5-yl)-2-pyrrolidinecarboxamide, salts thereof, N-oxides thereof, solvates thereof, and prodrugs thereof.

Compounds of the present invention containing one or more chiral centres may be used in enantiomerically or diastereoisomerically pure form, or in the form of a mixture of isomers. For the avoidance of doubt, the compounds of the invention may be used in any tautomeric form.

Unless otherwise specifically mentioned, all isomers are included in the present invention. For example, alkyl, alkenyl, alkynyl, alkoxy and alkylthio may be straight chain or branched. Moreover, all isomers due to double bond, ring and fused ring (E-, Z-, cis- and trans-forms), isomers due to the presence of asymmetric carbon(s) etc. (R-, S-, α- and β-configuration, enantiomer and diastereomer), optically active substances having optical rotation (D-, L-, d- and l-forms), polar compounds by chromatographic separation (more polar compounds and less polar compounds), equilibrium compounds, rotational isomers, a mixture thereof in any proportion and a racemic mixture are included in the present invention.

According to the present invention, symbol "⋯" represents α-configuration, symbol ⬩ represents β-configuration and symbol ⬩ represents α-configuration, β-configuration or a mixture of them. There is no particular limitation for the ratio of α-configuration and β-configuration in the mixture.

Salts:

The salt of the compound of formula (I) includes all nontoxic salts or pharmaceutically acceptable salts. With regard to the pharmaceutically acceptable salts, those which are low-toxicity and soluble in water are preferred. Examples of appropriate salts of the compound of formula (I) are salt with alkaline metal (such as potassium, sodium and lithium), salt with alkaline earth metal (such as calcium and magnesium), ammonium salt (such as ammonium salt, tetramethylammonium salt and tetrabutylammonium salt), salt with organic amine (such as triethylamine, methylamine, dimethylamine, cyclopentylamine, benzylamine, phenethylamine, piperidine, monoethanolamine, diethanolamine, tris(hydroxymethyl) methylamine, lysine, arginine and N-methyl-D-glucamine) and acid addition salt (such as inorganic acid salt (e.g. hydrochloride, hydrobromide, hydroiodide, sulfate, phosphate and nitrate) and organic acid salt (e.g. formate, acetate, trifluoroacetate, lactate, tartrate, oxalate, fumarate, maleate, benzoate, citrate, methanesulfonate, ethanesulfonate, benzenesulfonate, toluenesulfonate, isothionate, glucuronate and gluconate), etc.). The salt of the compound of the present invention also includes solvates and also solvates with the above-mentioned alkaline (earth) metal salt, ammonium salt, organic amine salt and acid addition salt. The solvate is preferably low-toxic and water-soluble. Examples of an appropriate solvate are solvates with water and with alcoholic solvent (such as ethanol). The compounds of the present invention are converted to low-toxicity salts or pharmaceutically acceptable salts by known methods.

Moreover, the salt includes a quaternary ammonium salt. The quaternary ammonium salt of the compound represented by formula (I) is the compound where nitrogen of the compounds represented by formula (I) is quarternalized by $R^O$ ($R^O$ is C1-8 alkyl or C1-8 alkyl substituted by phenyl).

The salt also includes an N-oxide. The compound of the present invention can be converted into an N-oxide by known methods. The N-oxide is the compound where nitrogen of the compound represented by formula (I) is oxidized.

Prodrugs:

A prodrug of the compound of formula (I) means a compound which is converted to the compound of formula (I) by reaction with an enzyme, gastric acid or the like in the living body. For example, with regard to a prodrug of the compound of formula (I), when the compound of formula (I) has an amino group, compounds in which the amino group is, for example, acylated, alkylated or phosphorylated (e.g. compounds in which the amino group of the compound of formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, etc.); when the compound of formula (I) has a hydroxyl group, compounds where the hydroxyl group is, for example, acylated, alkylated, phosphorylated or borated (e.g. compounds in which the hydroxyl group of the compound of formula (I) is acetylated, palmitoylated, propanoylated, pivaloylated, succinylated, fumarylated, alanylated or dimethylaminomethylcarbonylated); when the compound of formula (I) has an amidino group, compounds in which the amidino group is, for example, hydroxylated, etherified or carbamated (e.g. compounds in which the amidino group of the compound of formula (I) is N,N'-dihydroxylated, N-methoxycarbonylated, N-2,2,2-trichloroethoxycarbonylated, N-ethylthiocarbonylated, N-benzyloxycarbonylated, N-(5-methyl-2-oxo-1,3-dioxol-4-en-1-yl)-methoxycarbonylated, N-phenoxycarbonylated, N-(4-fluorophenoxy)carbonylated, N-(4-methoxyphenoxy)carbonylated, 1-acetoxyethoxycarbonylated, N-ethoxycarbonyloxylated, etc.); and when the compound of formula (I) has a carboxyl group, compounds in which the carboxyl group is, for example, esterified or amidated (e.g. compounds in which the carboxyl group of the compound of formula (I) is converted into ethyl ester, phenyl ester, phenylethyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide). Those compounds may be produced by a known method per se. The prodrug of the compound of formula (I) may be either a hydrate or a non-hydrate. A prodrug of the compound of formula (I) may also be a compound which is converted to the compound of formula (I) under physiological conditions as described in "Iyakuhin no kaihatsu, Vol. 7 (Bunshi-sekkei), pp. 163-198 (Hirokawa-Shoten), 1990". Further, the compound of formula (I) may also be labeled by a radio isotope (such as $^2H$, $^3H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, $^{125}I$, etc.).

Processes for the Preparation of the Compound of the Present Invention

The compounds of the invention can, for example, be prepared according to the following reaction schemes.

The compound of the present invention represented by the formula (I) may be prepared by known methods, for example, a method combining the following methods, the method according to these methods, the methods described in the examples and/or methods described in Comprehensive Organic Transformations: A Guide to Functional Group Preparations, 2nd Edition (Richard C. Larock, John Wiley & Sons Inc, 1999), etc., which are appropriately modified in each following method for the preparation. Salts of the starting materials may be used.

It will also be recognized that another major consideration in the planning of any synthetic route in this field is the judicious choice of the protecting group used for protection of the reactive functional groups present in the compounds described in this invention. Protection reactions may be carried out by the methods, for example, described in T. W. Greene, Protective Groups in Organic Synthesis, Wiley, New York, 1999.

The compound of formula (I) can be prepared from a compound represented by formula (II):

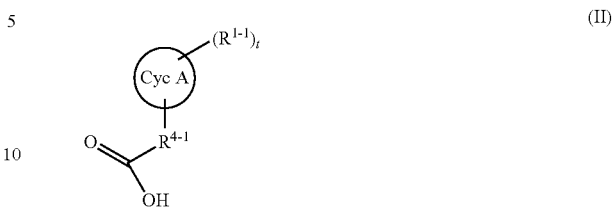

wherein $R^{1-1}$ and $R^{4-1}$ have the same meanings as $R^1$ and $R^4$ respectively. When additional carboxyl or amino groups are present they are protected, if the protection is necessary, during the amidation process with a compound represented by the formula (III):

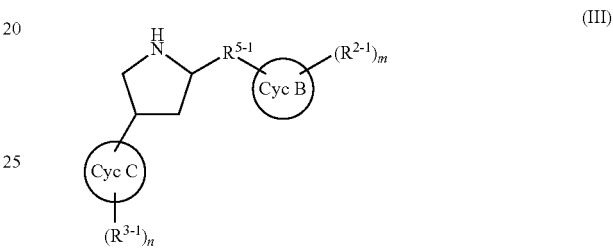

wherein $R^{2-1}$, $R^{3-1}$ and $R^{5-1}$ have the same meanings as $R^2$, $R^3$ and $R^5$ respectively. When additional carboxyl, hydroxy or amino groups are present they are protected if protection is necessary.

The amidation reaction is well known. For example, the reaction of the compound represented by formula (II) with the compound represented by formula (III) wherein all symbols have the same meaning described above is exemplified by:

(1) A reaction procedure with use of an acid halide,
(2) A reaction procedure with use of a mixed acid anhydride, and
(3) A reaction procedure with use of a condensing agent.

Referring specifically to these reaction procedures, (1) The reaction procedure employing an acid halide is conducted in practice, for example, by reacting a carboxylic acid with an acid halogenating agent (e.g. oxalyl chloride, thionyl chloride, etc.) in an organic solvent (e.g. chloroform, dichloromethane, diethyl ether, tetrahydrofuran, dimethoxyethane, etc.) at a temperature from about −20° C. to the refluxing temperature, followed by reaction of the resultant acid halide with an amine in an organic solvent (e.g. chloroform, dichloromethane, diethyl ether, tetrahydrofuran, acetonitrile, ethyl acetate, etc.) or solvent-free in the presence of a base (e.g. pyridine, triethylamine, dimethylaniline, 4-dimethylaminopyridine, diisopropylethylamine, etc.) at a temperature of approximately 0 to 40° C. Alternatively, the procedure can be carried out by reacting the resultant acid halide with an amine in an organic solvent (e.g. 1,4-dioxane, tetrahydrofuran, dichloromethane, etc.) in the presence or absence of a phase-transfer catalyst (e.g. tetrabutylammonium chloride, triethylbenzylammonium chloride, tri-n-octylmethylammonium chloride, trimethyldecylammonium chloride, tetramethylammonium chloride, trimethyldecylammonium chloride, tetramethylammonium chloride, etc.) at a temperature of about 0 to 40° C., whilst using an aqueous alkali solution (e.g. an aqueous sodium bicarbonate or sodium hydroxide solution, etc.).

(2) The reaction procedure employing a mixed acid anhydride is conducted in practice, for example, by reacting a carboxylic acid with an acid halide (e.g. pivaloyl chloride, tosyl chloride, mesyl chloride, etc.) or an acid derivative (e.g. ethyl chloroformate, isobutyl chloroformate, etc.) in an organic solvent (e.g. chloroform, dichloromethane, diethyl ether, tetrahydrofuran, etc.) or solvent free in the presence of base (e.g. pyridine, triethylamine, dimethylaniline, 4-dimethylaminopyridine, diisopropylethylamine, etc.) at a temperature of about 0 to 40° C., followed by reaction of the resultant mixed acid anhydride with an amine in an organic solvent (e.g. chloroform, dichloroethane, diethyl ether, tetrahydrofuran, etc.) at a temperature of about 0 to 40° C.

(3) The reaction procedure with use of a condensing agent is carried out, for example, by reacting a carboxylic acid with an amine in an organic solvent (e.g. chloroform, dichloromethane, N,N-dimethylformamide, diethyl ether, tetrahydrofuran, etc.) or solvent-free in the presence or absence of a base (e.g. pyridine, triethylamine, diisopropylethylamine, dimethylaniline, 4-dimethylaminopyridine, etc.), with use of a condensing agent (e.g. 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide, 1,1'-propylphosphonic acid anhydride (1-propanephosphonic acid cyclic anhydride, PPA), 2-(7-aza-1H-benzotriazole-1-yl)-1,1,3,3-tetramethyluronium hexafluorophosphate (HATU), etc.) and with or without use of 1-hydroxybenztriazole (HOBt), at a temperature of about 0 to 40° C.

In the course of the synthesis of the compound of the present invention represented by the formula (I), the deprotection reaction can be carried out at an appropriate synthetic stage when protective groups of carboxyl, hydroxy or amino groups are present.

The deprotection reactions for protective groups of carboxyl, hydroxy or amino groups are well-known and include, for example, (1) a deprotection reaction by alkali hydrolysis,
(2) a deprotection under acidic conditions,
(3) a deprotection reaction by hydrogenolysis,
(4) a deprotection reaction of a silyl group,
(5) a deprotection reaction using a metal,
(6) a deprotection reaction using a metal complex, etc.

To explain these methods in detail:

(1) The deprotection reaction by alkali hydrolysis is carried out, for example, in an organic solvent (methanol, tetrahydrofuran, 1,4-dioxane, etc.) using a hydroxide of alkali metals (sodium hydroxide, potassium hydroxide, lithium hydroxide, etc.), hydroxide of alkaline earth metals (barium hydroxide, calcium hydroxide, etc.), carbonate (sodium carbonate, potassium carbonate, etc.) or a solution thereof or a mixture thereof at a temperature of 0 to 40° C.

(2) The deprotection reaction under acidic conditions is carried out, for example, in an organic solvent (dichloromethane, chloroform, 1,4-dioxane, ethyl acetate, anisole, etc.), using an organic acid (acetic acid, trifluoroacetic acid, methanesulfonic acid, p-toluenesulfonic acid, etc.) or an inorganic acid (hydrochloric acid, sulfuric acid, etc.) or a mixture thereof (hydrobromic acid/acetic acid, etc.) in the presence or absence of 2,2,2-trifluoroethanol at a temperature of 0 to 100° C.

(3) The deprotection reaction by hydrogenolysis is, for example, carried out in a solvent (e.g. ethers such as tetrahydrofuran, 1,4-dioxane, dimethoxyethane, diethyl ether, etc.; alcohols such as methanol, ethanol, etc.; benzenes such as benzene, toluene, etc.; ketones such as acetone, methyl ethyl ketone, etc.; nitriles such as acetonitrile etc.; amides such as N,N-dimethylformamide, N,N-dimethylacetamide etc.; water, ethyl acetate, acetic acid or a mixture of two or more thereof, etc.) in the presence of a catalyst (palladium-carbon, palladium black, palladium hydroxide, platinum oxide, Raney nickel, etc.) under an atmosphere of hydrogen at normal or increased pressure, or in the presence of ammonium formate at a temperature of 0 to 200° C.

(4) The deprotection reaction of a silyl group is, for example, carried out in a water-miscible organic solvent (tetrahydrofuran, acetonitrile, etc.) using tetrabutylammonium fluoride at a temperature of 0 to 40° C.

(5) The deprotection reaction using a metal is carried out, for example, in an acidic solvent (acetic acid, a buffer of pH 4.2 to 7.2 or a mixture of the solution thereof and an organic solvent such as tetrahydrofuran etc.) in the presence of zinc powder at a temperature of 0 to 40° C. optionally under sonication.

(6) The deprotection reaction using a metal complex is carried out, for example, in an organic solvent (dichloromethane, N,N-dimethylformamide, tetrahydrofuran, ethyl acetate, acetonitrile, 1,4-dioxane, ethanol, etc.), water or a mixture thereof, in the presence of a trapping reagent (tributyltin hydride, triethylsilane, dimedone, morpholine, diethylamine, pyrrolidine, 1,3-dimethylbarbituric acid, etc.), an organic acid (acetic acid, formic acid, 2-ethylhexanecarboxylic acid, etc.) and/or a salt of an organic acid (sodium 2-ethylhexanoate, potassium 2-ethylhexanoate, etc.) in the presence or absence of a phosphine reagent (triphenylphosphine etc.) using a metal complex (tetrakis(triphenylphosphine)palladium (0), palladium(II) bis(triphenylphosphine) dichloride, palladium(II) acetate, rhodium(I) tris(triphenylphosphine) chloride, etc.) at a temperature of 0 to 40° C.

In addition to the above, deprotection reactions may be carried out by the methods, for example, described in T. W. Greene, Protective Groups in Organic Synthesis, Wiley, New York, 1999.

A protective group for carboxyl includes, for example, methyl, ethyl, allyl, tert-butyl, trichloroethyl, benzyl (Bn), phenacyl, p-methoxybenzyl, trityl, 2-chlorotrityl or a solid carrier containing these structures, etc.

A protective group for hydroxy includes, for example, methyl (Me), trityl (Tr), methoxymethyl (MOM), 1-ethoxyethyl (EE), methoxyethoxymethyl (MEM), 2-tetrahydropyranyl (THP), trimethylsilyl (TMS), triethylsilyl (TES), tert-butyldimethylsilyl (TBDMS), tert-butyldiphenylsilyl (TBDPS), acetyl (Ac), pivaloyl (Pv), benzoyl (Bz), benzyl (Bn), p-methoxybenzyl (PMB), allyloxycarbonyl (Alloc) or 2,2,2-trichloroethoxycarbonyl (Troc), etc.

A protective group for amino includes, for example, benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl (FMoc), benzyl (Bn), p-methoxybenzyl, benzyloxymethyl (BOM), 2-(trimethylsilyl)ethoxymethyl (SEM), etc.

Protective groups for carboxyl, hydroxy or amino group are not limited to those described above, but include groups which are easily and selectively deprotected. For example, those groups described in T. W. Greene, Protective Groups in Organic Synthesis, Wiley, New York, 1999.

As is easily understood by those skilled in the art, the target compound of the present invention may be prepared easily by selecting these deprotection reactions.

1) The compound of formula (III) wherein $R^{5-1}$ represents a carboxyamide which is attached to Cyc B at nitrogen atom, that is, a compound represented by formula (III-1):

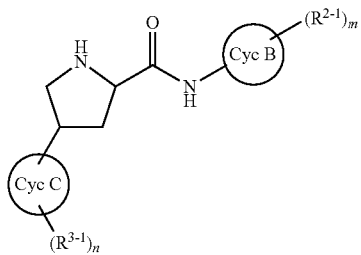

(III-1)

wherein all symbols have the same meaning described above, can be prepared as outlined in Reaction Scheme 1:

Reaction Scheme 1

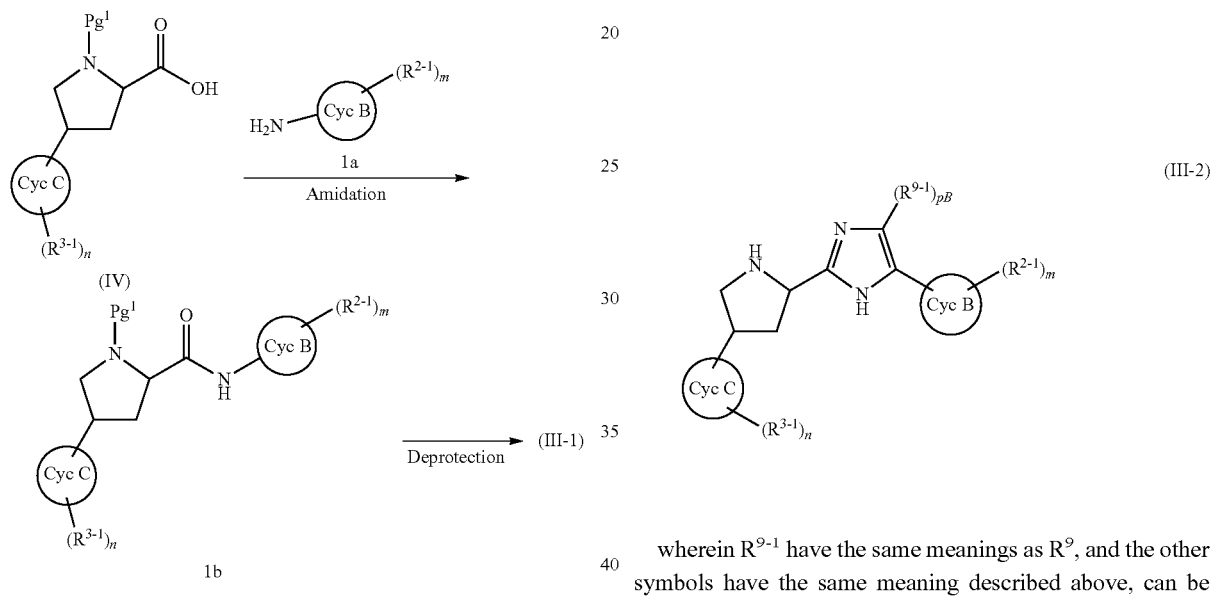

wherein $Pg^1$ represents a protective group for amino described above and the other symbols have the same meaning described above.

In Reaction Scheme 1, the compound represented by formula (IV) and the amine compound represented by formula 1a can be condensed to produce the compound represented by formula 1b by an amidation reaction as described above. The compound represented by formula 1b can be converted to the amine compound represented by the formula (III-1) by a deprotection reaction as described above.

2) The compound of formula (III) wherein $R^{5-1}$ represents an imidazole which is attached to Cyc B at the 4-position, that is, a compound represented by formula (III-2):

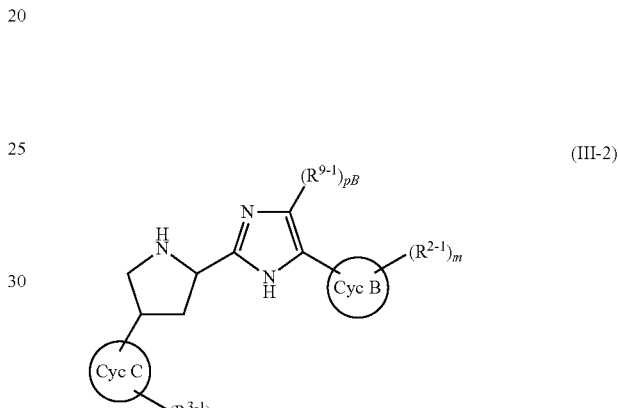

(III-2)

wherein $R^{9-1}$ have the same meanings as $R^9$, and the other symbols have the same meaning described above, can be prepared as outlined in Reaction Scheme 2:

Reaction Scheme 2

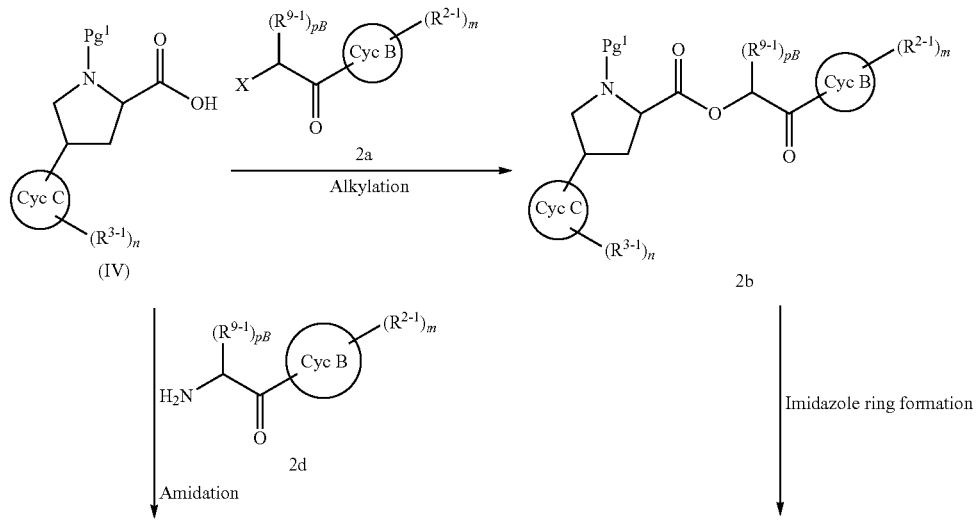

-continued

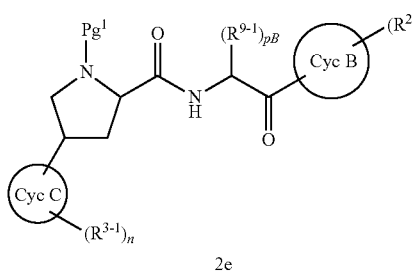

2e

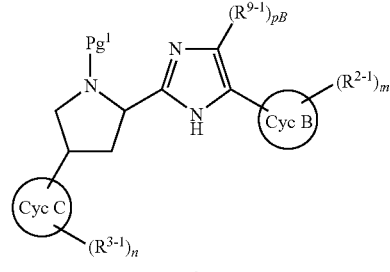

2c

Imidazole ring formation

Deprotection (III-2)

wherein X represents fluorine, chlorine, bromine or iodine, and the other symbols have the same meaning described above.

In Reaction Scheme 2, the reaction from the compound represented by formula (IV) to the compound represented by formula 2b is an alkylation reaction.

The alkylation reaction is well known. For example, the alkylation reaction of the compound represented by formula (IV) with the compound represented by formula 2a can be conducted in a solvent such as N,N-dimethylformamide, tetrahydrofuran, dichloromethane, acetone or acetonitrile in the presence of a base such as sodium carbonate, potassium carbonate, cesium carbonate, sodium bicarbonate, potassium bicarbonate, N,N-diisopropylethylamine or triethylamine at −20° C. to reflux temperature to form a compound represented by formula 2b wherein all symbols have the same meaning described above.

The reaction from the compound represented by formula 2b to the compound represented by formula 2c is an imidazole formation reaction.

The imidazole formation reaction is well known. For example, the compound represented by formula 2b can be converted to compounds of formula 2c by heating and/or microwave irradiation in the presence of ammonium acetate or ammonium trifluoroacetate in a suitable solvent such as xylene, toluene or acetic acid.

Alternatively, the compound represented by formula 2c can be prepared from the compound represented by formula 2e. The reaction from the compound represented by formula (IV) to the compound represented by formula 2e is an amidation reaction.

The amidation reaction of the compound represented by formula (IV) with the compound represented by formula 2d can be conducted by the method as described above.

The reaction from the compound represented by formula 2e to the compound represented by formula 2c is an imidazole formation reaction. The imidazole formation reaction can be carried out by the same method as described above.

The compound represented by formula 2c can be converted to the amine compound represented by the formula (III-2) by a deprotection reaction as described above.

3) The compound of formula (III) wherein $R^5$ represents an imidazole ring which is attached to Cyc B at the 4-position and possesses $R^{9\text{-}hal}$, that is, a compound represented by formula (III-3):

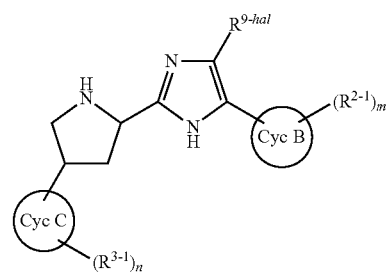

(III-3)

wherein $R^{9\text{-}hal}$ represents fluorine, chlorine, bromine or iodine, and the other symbols have the same meaning described above, can be prepared as outlined in Reaction Scheme 3.

Reaction Scheme 3

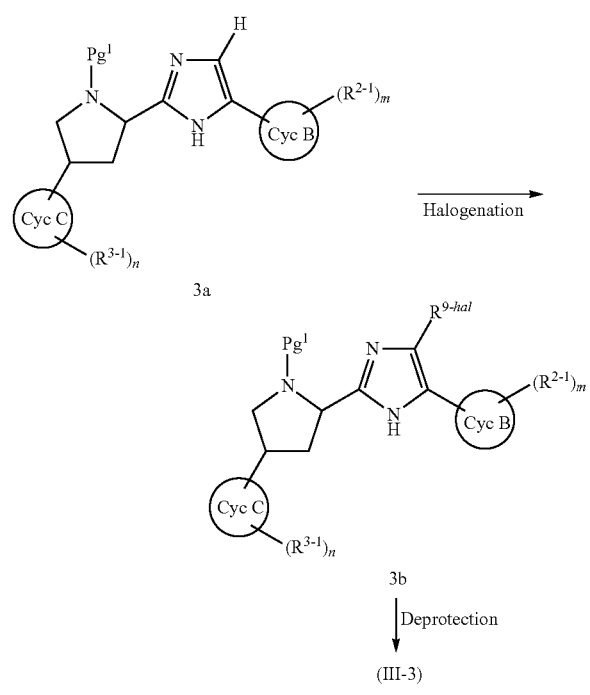

3a

Halogenation

3b

Deprotection (III-3)

wherein all symbols have the same meanings as described above.

In Reaction Scheme 3, the reaction from the compound represented by formula 3a to the compound represented by formula 3b is a halogenation reaction.

The halogenation reaction is well known. For example, the reaction of the compound represented by formula 3a with brominating or chlorinating agent, such as N-bromosuccinimide, N-chlorosuccinimide or 1,3-dichloro-5,5-dimethylhydantoin in a suitable solvent such as acetonitrile, chloroform or tetrahydrofuran from −20° C. to the refluxing temperature provides the compound represented by formula 3b.

The compound represented by formula 3b can be converted to the amine compound represented by the formula (III-3) by a deprotection reaction as described above.

4) The compound of formula (IV) wherein Cyc C is attached to pyrrolidine ring via nitrogen atom, that is, a compound represented by formula (IV-1):

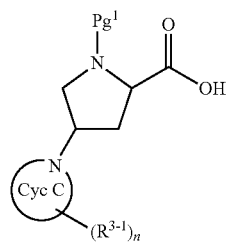

(IV-1)

wherein all symbols have the same meanings as described above, can be prepared as outlined in Reaction Scheme 4:

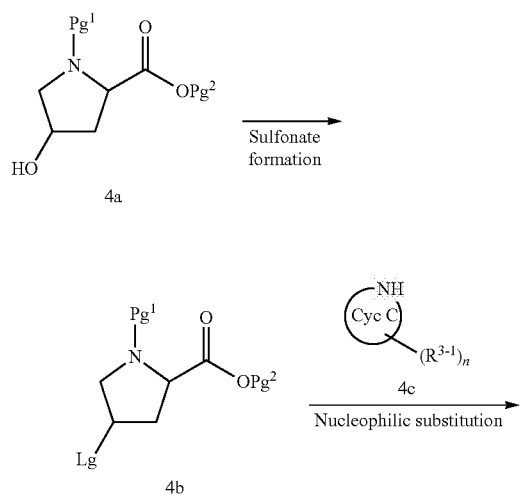

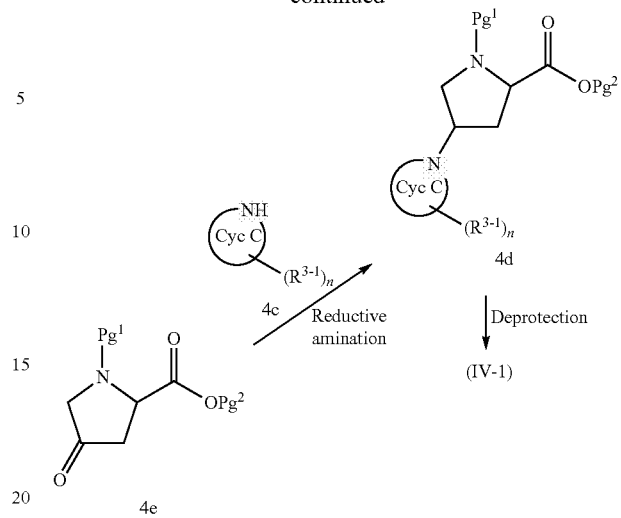

wherein $Pg^2$ represents a protective group for carboxyl described above and Lg represents triflate, tosylate or mesylate and the other symbols have the same meaning described above.

In Reaction Scheme 4, the reaction from the compound represented by formula 4a to the compound represented by formula 4b is a sulfonate formation reaction.

The sulfonate formation reaction is well known. For example, the treatment of the compound represented by formula 4a with a sulfonating reagent such as trifluoromethanesulfonic anhydride, p-toluenesulfonyl chloride or methanesulfonyl chloride in a solvent such as tetrahydrofuran or dichloromethane in the presence of a base such as N,N-diisopropylethylamine or triethylamine at −20° C. to reflux temperature provides a compound represented by formula 4b.

The reaction from the compound represented by formula 4b to the compound represented by formula 4d is a nucleophilic substitution reaction.

The nucleophilic substitution reaction is well known. For example, the nucleophilic substitution reaction of compound 4b with compounds of formula 4c can be conducted in a solvent such as tert-butanol or N,N-dimethylformamide in the presence of a base such as N,N-diisopropylethylamine or triethylamine at 20° C. to reflux temperature to provide the compound represented by formula 4d.

Alternatively, the compound represented by formula 4d can be prepared from the compound represented by formula 4e. The reaction from the compound represented by formula 4e to the compound represented by formula 4d is a reductive amination reaction.

The reductive amination reaction of the compound represented by formula 4e with the compound represented by formula 4c can be conducted in a solvent such as methanol, tetrahydrofuran, dichloromethane, 1,2-dichloroethane or acetic acid in the presence of a reductant such as sodium cyanoborohydride or sodium triacetoxyborohydride at −20° C. to reflux temperature to provide the compound represented by formula 4d.

The compound represented by formula 4d can be converted to the amine compound represented by the formula (IV-1) by a deprotection reaction as described above.

5) The compound of formula (IV) wherein Cyc C is appropriately substituted piperidine which is attached to pyrrolidine ring at 4-position of piperidine ring, that is, a compound represented by formula (IV-2):

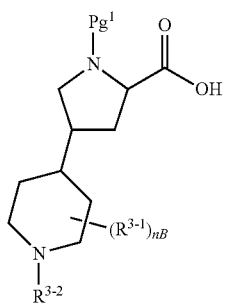

wherein $R^{3-1}$ and $R^{3-2}$ has the same meanings as $R^3$, with the proviso that a carboxyl, hydroxyl or amino group in $R^{3-1}$ and $R^{3-2}$ may be protected if necessary, can be prepared as outlined in Reaction Scheme 5:

Suzuki coupling reaction between a compound represented by formula 5b with an appropriately functionalized 4-pyridineboronic acid or ester in the presence of a base such as anhydrous cesium carbonate, cesium fluoride, sodium carbonate or potassium phosphate in a solvent such as 1,4-dioxane, N,N-dimethylformamide or dimethylsulfoxide using a catalyst such as tetrakis(triphenylphosphine)palladium(0), 1,1'-bis(diphenylphosphino)ferrocene palladium (II) chloride, palladium(II) acetate or bis(dibenzylidenacetone)palladium(0), with or without a phosphine ligand such as triphenylphosphine, tri-tert-butylphosphine or 1,1'-bis(diphenylphosphino)ferrocene at a temperature from about 70° C. to the refluxing temperature provides the compounds represented by formula 5c.

In cases where suitably substituted boronic acids or esters are not commercially available, the 4,4,5,5-tetramethyl-[1,3,2]dioxaborolane intermediate can be prepared from the corresponding aryl halide or aryl triflate by a palladium mediated coupling with a diboron species such as bis(pinacolato)diboron using the method of Ishiyama, T. et al. (*J. Org. Chem.*, 1995, 60(23), 7508). Alternatively, the

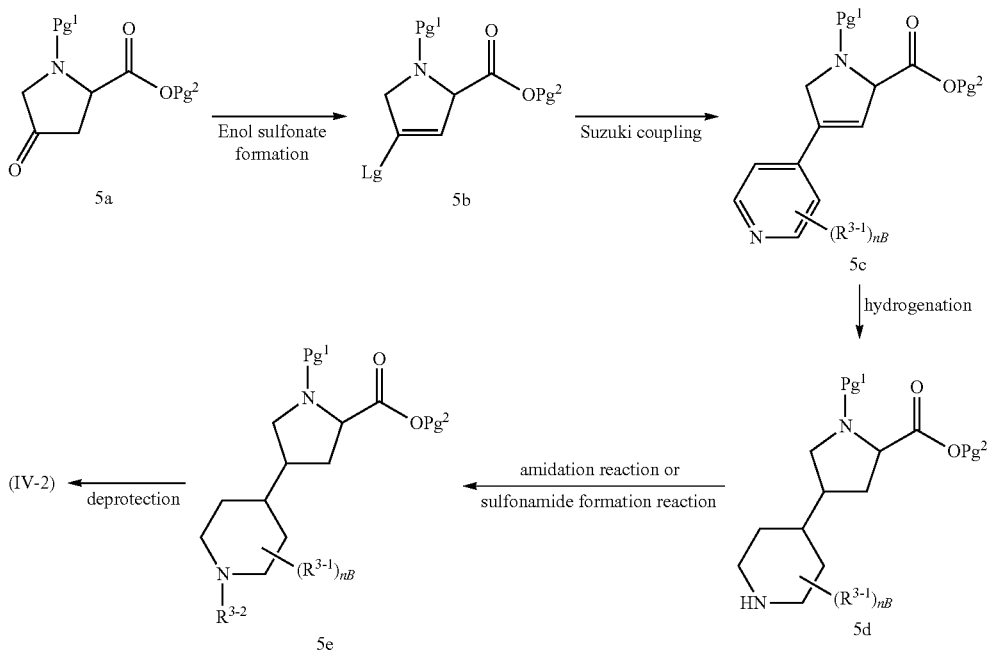

Reaction Scheme 5 wherein all symbols have the same meaning described above.

In Reaction Scheme 5, the reaction from the compound represented by formula 5a to the compound represented by formula 5b is an enol sulfonate formation reaction.

The enol sulfonate formation reaction is well known. For example, the treatment of the compound represented by formula 5a with a sulfonating reagent such as trifluoromethanesulfonic anhydride, N-phenyltrifluoromethanesulfonimide, 2-[N,N-bis(trifluoromethanesulfonyl)amino]pyridine, p-toluenesulfonyl chloride, trifluoromethanesulfonic anhydride, p-toluenesulfonyl chloride and methanesulfonyl chloride in a solvent such as tetrahydrofuran or dichloromethane in the presence of a base such as lithium diisopropylamide or sodium bis(trimethylsilyl)amide at −78° C. to 0° C. provides a compound represented by formula 5b.

corresponding boronic acid can be prepared by metal-halogen exchange of the aryl/heteroaryl halide, quenching with a trialkoxyborate reagent and aqueous workup to provide the boronic acids (Miyaura, N.; Suzuki, A. *Chem. Review*, 1995, 95, 2457).

The hydrogenation reaction of 5c can be conducted in a solvent such as methanol, ethanol or acetic acid in the presence of a catalyst such as palladium-carbon, palladium black, palladium hydroxide, platinum-carbon or platinum oxide under an atmospheric or increased pressure of hydrogen to give a compound represented by formula 5d.

The compound represented by formula 5d can be converted to the N-substituted compounds represented by formula 5e by an amidation reaction or sulfonamide formation reaction.

The compound of formula 5e wherein $R^{3-2}$ represents acyl group can be prepared by an introduction of $R^{3-2}$ group using an amidation reaction as described above.

The compound of formula 5e wherein $R^{3-2}$ represents sulfonyl group can be prepared by an introduction of $R^{3-2}$ group using a sulfonamide formation reaction.

The sulfonamide formation reaction is well known. For example, the treatment of the compound represented by formula 5d with appropriately substituted sulfonating reagent such as an alkylsulfonic anhydride, alkylsulfonyl chloride or aryl sulfonyl chloride in a solvent such as tetrahydrofuran or dichloromethane in the presence of a base such as N,N-diisopropylethylamine or triethylamine at −20° C. to reflux temperature to provide the compound represented by formula 5e.

The compound represented by formula 5e can be converted to the amine compound represented by the formula (IV-2) by a deprotection reaction as described above.

The compounds of the present invention can be prepared by the reactions or modified variants of the reactions described above.

Other starting compounds or compounds used as reagents are known compounds which can be prepared easily by a combination of known methods, for example, the methods described in Comprehensive Organic Transformations: A Guide to Functional Group Preparations, 2nd Edition (Richard C. Larock, John Willey & Sons Inc, 1999) or Elmer J. Rauckman et al., *J. Org. Chem.*, 1976, 41(3), 564 etc.

In each reaction of the specification the reactions with heating, as will be apparent to those skilled in the art, may be carried out using a water bath, an oil bath, a sand bath, a heating block or by microwave.

In each reaction of the specification, a solid phase reagent may be used which is supported by a polymer (for example polystyrene, polyacrylamide, polypropylene or polyethyleneglycol etc.).

In each reaction of the specification, the products obtained may be purified by conventional techniques. For example, the purification may be carried out by distillation at atmospheric or reduced pressure, by high performance liquid chromatography with silica gel or magnesium silicate, by thin layer chromatography, by ion-exchange resin, by scavenger resin, by column chromatography, by washing, trituration or recrystallization. The purification may be carried out after each reaction stage or after several reaction stages.

In a reaction of the specification where polystyrene resin is used, the obtained products may be purified by conventional techniques. For example, the purification may be carried out by multiple washing with a solvent (for example, N,N-dimethylformamide, dichloromethane, methanol, tetrahydrofuran, toluene, acetic acid/toluene, etc.).

Toxicity:

The compound represented by formula (I), the salt thereof, the N-oxide thereof, the solvate thereof or the prodrug thereof show low toxicity (e.g. acute toxicity, chronic toxicity, genotoxicity, developmental toxicity, cardiac toxicity, drug interaction, carcinogenicity) and lack side effects such as bleeding. It may therefore be considered safe for pharmaceutical use.

Application to Pharmaceuticals:

The compounds of the present invention are therapeutically useful. The present invention therefore provides a compound of formula (I), as defined above, or a pharmaceutically acceptable salt thereof, an N-oxide thereof, a solvate thereof or a prodrug thereof, for use in the treatment of the human or animal body by therapy.

Also provided is a pharmaceutical composition comprising a compound of formula (I), as defined above, or a pharmaceutically acceptable salt thereof, an N-oxide thereof, a solvate thereof or a prodrug thereof, and a pharmaceutically acceptable carrier or diluent.

Said pharmaceutical composition typically contains up to 85 wt % of a compound of the invention. More typically, it contains up to 50 wt % of a compound of the invention. Preferred pharmaceutical compositions are sterile and pyrogen free. Further, the pharmaceutical compositions provided by the invention typically contain a compound of the invention which is a substantially pure optical isomer.

The compounds of the present invention may normally be administered systemically or locally, usually by oral, parenteral or continuous administration.

A therapeutically effective amount of a compound of the invention is administered to a patient. The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds or pharmaceutical compositions of the present invention may be administered, for example, in the form of a solid for oral administration, liquid forms for oral administration, injections, liniments or suppositories for parenteral administration. Solid forms for oral administration include compressed tablets, pills, capsules, dispersible powders, and granules. Capsules include hard capsules and soft capsules.

In such solid forms, one or more of the active compound(s) may be admixed with vehicles (such as lactose, mannitol, glucose, microcrystalline cellulose or starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, solution adjuvants (such as glutamic acid or aspartic acid, disaggregating agents, e.g. starch, alginic acid, alginates or sodium starch glycolate; effervescing mixtures, dyestuffs, sweeteners, wetting agents, such as lecithin, polysorbates, laurylsulphates; and, in general, non-toxic and pharmacologically inactive substances used in pharmaceutical formulations and prepared according to methods well known in normal pharmaceutical practice, for example, by means of mixing, granulating, tableting, sugar coating, or film coating processes. The solid forms may, if desired, be coated with coating agents (such as sugar, gelatin, hydroxypropyl cellulose or hydroxypropylmethyl cellulose phthalate) or be coated with two or more films. Furthermore, coating may include containment within capsules of absorbable materials such as gelatin.

Liquid forms for oral administration include pharmaceutically acceptable solutions, suspensions, emulsions, syrups and elixirs. In such forms, one or more of the active compound(s) may be dissolved, suspended or emulsified into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent. The syrups may contain as carriers, for example, saccharose or saccharose with glycerine and/or mannitol and/or sorbitol.

Suspensions and emulsions may contain a carrier, for example a natural gum, agar, sodium alginate, pectin, methylcellulose, carboxymethylcellulose or polyvinyl alcohol. The suspension or solutions for intramuscular injections may contain, together with the active compound, a pharmaceutically acceptable carrier e.g. sterile water, olive oil, ethyl oleate, glycols (e.g. propylene glycol) and, if desired, a suitable amount of lidocaine hydrochloride.

Solutions for injection or infusion may contain as carrier, for example, sterile water or preferably they may be in the form of sterile, aqueous, isotonic saline solutions.

Injections for parenteral administration include sterile aqueous suspensions, emulsions and solid forms which are dissolved or suspended into solvent(s) for injection immediately before use. In injections, one or more of the active compound(s) may be dissolved, suspended or emulsified into solvent(s). The solvents may include distilled water for injection, saline, vegetable oil, propylene glycol, polyethylene glycol, alcohol such as ethanol, or a mixture thereof. Injections may comprise some additives, such as stabilizing agents, solution adjuvants (such as glutamic acid, aspartic acid or POLYSORBATE80 (registered trade mark)), suspending agents, emulsifying agents, soothing agents, buffering agents or preservatives. They may be sterilized at a final step, or may be prepared according to sterile methods. They may also be manufactured in the form of sterile solid forms such as freeze-dried products, which may be dissolved in sterile water or some other sterile diluent(s) for injection immediately before use.

Other forms for parenteral administration include liquids for external use, ointments and endermic liniments, inhalations, sprays, suppositories and vaginal suppositories which comprise one or more of the active compound(s) and may be prepared by methods known per se.

Sprays may comprise additional substances other than diluents used commonly, stabilizers such as sodium hydrogensulfite and buffers capable of imparting isotonicity, for example, isotonic buffers such as sodium chloride, sodium citrate or citric acid.

Effect of the Invention:

The compounds of the present invention represented by formula (I) act as potent and selective inhibitors of factor XIa, and also show superior properties as a pharmaceutical product such as stability, water solubility and the like. Thus the compounds of the present invention are useful in preventing and/or treating thromboembolic diseases. One advantage of the compounds of the present invention is that they can provide high inhibitory activity against FXIa and high safety without side effects such as bleeding.

The present invention therefore provides a compound of formula (I), as defined above, or a pharmaceutically acceptable salt thereof, an N-oxide thereof, a solvate thereof or a prodrug thereof, for use in treating or preventing a thromboembolic disease. Also provided is a method for treating a patient suffering from or susceptible to a thromboembolic disease, which method comprises administering to said patient an effective amount of a compound of formula (I), as defined above, or a pharmaceutically acceptable salt thereof, an N-oxide thereof, a solvate thereof or a prodrug thereof. Further provided is the use of a compound of formula (I), as defined above, or a pharmaceutically acceptable salt thereof, an N-oxide thereof, a solvate thereof or a prodrug thereof, in the manufacture of a medicament for use in treating or preventing a thromboembolic disease.

The thromboembolic disease may be, for example, selected from the group consisting of arterial cardiovascular thromboembolic disorders, venous cardiovascular thromboembolic disorders, arterial cerebrovascular thromboembolic disorders, venous cerebrovascular thromboembolic disorders and thromboembolic disorders in the chambers of the heart or in the peripheral circulation.

More specifically, arterial cardiovascular thromboembolic disorders may be exemplified by coronary artery disease, ischemic cardiomyopathy, acute coronary syndrome, coronary arterial thrombosis, ischemic complications of unstable angina and non-Q-wave myocardial infarction, acute non ST-segment elevation and/or ST-segment elevation myocardial infarction managed medically or with subsequent percutaneous coronary intervention, angina pectoris such as stable effort angina pectoris, variant angina pectoris, unstable angina pectoris, myocardial infarction (e.g. first myocardial infarction or recurrent myocardial infarction), acute myocardial infarction, reocclusion and restenosis after coronary artery bypass surgery, reocclusion and restenosis after percutaneous transluminal cardiac angioplasty/transluminal coronary artery stent placement surgery or after thrombolytic therapy for coronary artery, ischemic sudden death. Venous cardiovascular thromboembolic disorders may be exemplified by deep vein thrombosis (DVT) and/or pulmonary embolism (PE) in major general surgery, abdominal surgery, hip replacement surgery, knee replacement surgery, hip fracture surgery, multiple fracture, multiple injury, trauma, spinal cord injury, burns, critical care unit, DVT and/or PE in medical patients with severely restricted mobility during acute illness, DVT and/or PE in patients with cancer chemotherapy, DVT and/or PE in patients with stroke, symptomatic or asymptomatic DVT with or without PE (pulmonary embolism). Arterial cerebrovascular thromboembolic disorders may be exemplified by stroke, ischemic stroke, acute stroke, stroke in patients with non-valuvelar or valuvelar atrial fibrillation, cerebral arterial thrombosis, cerebral infarction, transient ischemic attack (TIA), lacuna infraction, atherosclerotic thrombotic cerebral infarction, cerebral artery embolism, cerebral thrombosis, cerebrovascular disorder and asymptomatic cerebral infarction. Venous cerebrovascular thromboembolic disorders may be exemplified by intracranial venous thrombosis, cerebral embolism, cerevral thrombosis, sinus thrombosis, intracranial venous sinus thrombosis and cavernous sinus thrombosis. Thromboembolic disorders in the chambers of the heart or in the peripheral circulation may be exemplified by venous thrombosis, systemic venous thromboembolism, thrombophlebitis, non-valuvelar or valuvelar atrial fibrillation, cardiogenic embolism, disseminated intravascular coagulopathy (DIC), sepsis, acute respiratory distress syndrome (ARDS), acute lung injury (ALI), antiphospholipid antibody syndrome, kidney embolism, atherosclerosis, atherothrombosis, peripheral artery occlusive disease (PAOD), peripheral arterial disease, arterial embolism, and thrombosis resulting from medical implants, devices, or procedures in which blood is exposed to an artificial surface (such as catheters, stents, artificial heart valves or hemodialyzer) that promotes thrombosis.

Preferably, the thromboembolic disorder is selected from unstable angina, an acute coronary syndrome, atrial fibrillation, myocardial infarction (e.g. first myocardial infarction or recurrent myocardial infarction), ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, portal vein thrombosis, pulmonary embolism, pulmonary infarction, liver embolism, mesenteric artery and/or vein embolism, occlusion of retinal vein and/or artery, systemic embolism, disseminated intravascular coagulopathy (DIC), acute respiratory distress syndrome (ARDS), acute lung injury (ALI), antiphospholipid antibody syndrome, thrombosis resulting from coronary artery bypass graft surgery and thrombosis resulting from medical implants, devices, or procedures in which blood is exposed to an artificial surface (such as catheters, stents or artificial heart valves) that promotes thrombosis.

The compounds of the present invention may also be administered in combination with one or more further therapeutic agents. Thus, in another embodiment, the present invention provides a method for treating a thromboembolic disorder comprising: administering to a patient in need thereof a therapeutically effective amount of a first and second therapeutic agent, wherein the first therapeutic agent is a compound of formula (I), as defined above, or a pharmaceutically acceptable salt thereof, an N-oxide thereof, a solvate thereof or a prodrug thereof, and the second therapeutic agent is at least one agent selected from a second factor XIa inhibitor, an anti-coagulant agent, an anti-platelet agent, a thrombin inhibiting agent, a thrombolytic agent, a fibrinolytic agent, a serine protease inhibitor, an elastase inhibitor and an steroid. Preferably, the second therapeutic agent is at least one agent selected from warfarin, unfractionated heparin, low molecular weight heparin, enoxaparin, dalteparin, bemiparin, tinzaparin, semuloparin, danaparoid, synthetic pentasaccharide, fondaparinux, hirudin, disulfatohirudin, lepirudin, bivalirudin, desirudin, argatroban, aspirin, ibuprofen, naproxen, sulindac, indomethacin, mefenamate, droxicam, diclofenac, sulfinpyrazone, piroxicam, ticlopidine, clopidogrel, prasugrel, ticagrelor, cangrelor, elinogrel, cilostazol, sarpogrelate, iroprost, beraprost, limaprost, tirofiban, eptifibatide, abciximab, melagatran, ximelagatran, dabigatran, rivaroxaban, apixaban, edoxaban, darexaban, betrixaban, TAK-442, tissue plasminogen activator, modified tissue plasminogen activator, anistreplase, urokinase, streptokinase, gabexate, gabexate mesilate, nafamostat, sivelestat, sivelestat sodium hydrate, alvelestat, ZD-8321/0892, ICI-200880, tiprelestat, elafin, alpha1-antitrypsin, cortisone, betamethasone, dexamethasone, hydrocortisone, methylprednisolone, prednisolone and triamcinolone. Preferably, the second therapeutic agent is at least one anti-platelet agent. Preferably, the anti-platelet agent(s) are clopidogrel, prasugrel, ticagrelor, cangrelor, elinogrel, cilostazol, sarpogrelate, iroprost, beraprost, limaprost and/or aspirin, or a combination thereof. The present invention also provides a compound of formula (I), as defined above, or a pharmaceutically acceptable salt thereof, an N-oxide thereof, a solvate thereof or a prodrug thereof, in combination with a second therapeutic agent selected from those listed above, for use in treating or preventing a thromboembolic disease. The present invention also provides the use of a compound of formula (I), as defined above, or a pharmaceutically acceptable salt thereof, an N-oxide thereof, a solvate thereof or a prodrug thereof, in combination with a second therapeutic agent, in the manufacture of a medicament for use in treating or preventing a thromboembolic disease.

In another embodiment, the present invention provides a pharmaceutical composition comprising a compound of formula (I), as defined above, or a pharmaceutically acceptable salt thereof, an N-oxide thereof, a solvate thereof or a prodrug thereof and an additional therapeutic agent. Preferably, the further additional therapeutic agent(s) are selected from potassium channel openers, potassium channel blockers, calcium channel blockers, sodium hydrogen exchanger inhibitors, antiarrhythmic agents, antiatherosclerotic agents, anticoagulants, antiplatelets, antithrombotic agents, prothrombolytic agents, fibrinogen antagonists, diuretics, antihypertensive agents, ATPase inhibitors, mineralcorticoid receptor antagonists, phospodiesterase inhibitors, antidiabetic agents, protease inhibitors, elastase inhibitors, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, a serine protease inhibitor, an elastase inhibitor, an anti-inflammatory agent, or a combination thereof.

In another embodiment, the present invention provides a pharmaceutical composition further comprising additional therapeutic agent(s) selected from warfarin, unfractionated heparin, low molecular weight heparin, enoxaparin, dalteparin, bemiparin, tinzaparin, semuloparin, danaparoid, synthetic pentasaccharide, fondaparinux, hirudin, disulfatohirudin, lepirudin, bivalirudin, desirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, prasugrel, ticagrelor, cangrelor, elinogrel, cilostazol, sarpogrelate, iroprost, beraprost, limaprost, tirofiban, eptifibatide, abciximab, melagatran, ximelagatran, dabigatran, rivaroxaban, apixaban, edoxaban, darexaban, betrixaban, TAK-442, tissue plasminogen activator, modified tissue plasminogen activator, anistreplase, urokinase, streptokinase gabexate, gabexate mesilate, nafamostat, sivelestat, sivelestat sodium hydrate, alvelestat, ZD-8321/0892, ICI-200880, tiprelestat, elafin, alpha1-antitrypsin, cortisone, betamethasone, dexamethasone, hydrocortisone, methylprednisolone, prednisolone and triamcinolone or a combination thereof.

In a preferred embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, and vasopepsidase inhibitors, an anti-arrythmic agent selected from IKur inhibitors, elastase inhibitors, serine protease inhibitors, steroids, an anticoagulant selected from thrombin inhibitors, antithrombin-III activators, heparin co-factor II activators, other factor XIa inhibitors, plasma and/or tissue kallikrein inhibitors, plasminogen activator inhibitor (PAI-1) inhibitors, thrombin activatable fibrinolysis inhibitor (TAFI) inhibitors, factor VIIa inhibitors, factor VIIIa inhibitors, factor IXa inhibitors, factor Xa inhibitors and factor XIIa inhibitors, or an anti-platelet agent selected from GPII/IIIa blockers, protease activated receptor (PAR-1) antagonists, PAR-4 antagonists, phosphodiesterase-III inhibitors, other phosphodiesterase inhibitors, P2X1 antagonits, P2Y$_1$ receptor antagonists, P2Y$_{12}$ antagonists, thromboxane receptor antagonists, thromboxane A2 synthase inhibitors, cyclooxygense-1 inhibitors, phospholipase D1 inhibitors, phospholipase D2 inhibitors, phospholipase D inhibitors, glycoprotein VI (GPVI) antagonists, glycoprotein Ib (GPIb) antagonists, Growth arrest-specific gene 6 product (Gas6) antagonists and aspirin, or a combination thereof.

In a preferred embodiment, the present invention provides a pharmaceutical composition, wherein the additional therapeutic agent(s) are an anti-platelet agent or a combination thereof.

BEST MODE FOR CARRYING OUT THE INVENTION

The present invention is illustrated by the following Examples and biological Examples, but it is not limited thereto.

The solvents in the parentheses described in chromatographic separation and TLC show the eluting or developing solvents, and the ratios of the solvents used are given as percentage mixtures in chromatographic separations or TLC. Where a compound is described as dried, either anhydrous magnesium or sodium sulphate was used. The solvents in the parentheses in NMR show the solvents used in measurement. DMSO-d$_6$ represents deuterated dimethylsulfoxide; CDCl$_3$ represents deuterated chloroform; CD$_3$OD represents deuterated methanol; D$_2$O represents deuterated water. The following abbreviations are used in reporting the $^1$H NMR spectra: s (singlet), d (doublet), t (triplet), q (quartet), quint. (quintet), br. (broad), app. (apparent), obs. (obscured).

Including compounds in the following Examples, compounds used in the present specification were commonly named using a computer program capable of naming in accordance with IUPAC rules; ACD/Name® manufactured by Advanced Chemistry Development Inc., J Chem for Excel or MarvinSketch manufactured by ChemAxon Ltd., or IUPAC nomenclature. In each of the following Examples, the name of the objective compound of the Example is described subsequently to the number of the Example, and the compound is sometimes referred to as the "title compound".

Example 1 methyl(2S,4R)-4-hydroxy-2-pyrrolidinecarboxylate hydrochloride

To a solution of (2S,4R)-4-hydroxy-2-pyrrolidinecarboxylic acid hydrochloride (1.0 g, 7.6 mmol) in methanol (25 mL) at 0° C. was added thionyl chloride (0.83 mL, 11.4 mmol). The reaction was warmed to room temperature and heated at reflux overnight. After cooling to room temperature, the reaction mixture was concentrated to dryness to give the title compound (1.2 g, 92%) as a white solid.

$^1$H NMR (300 MHz, DMSO-d$_6$) δ 9.99 (br. s, 2H), 5.58 (br. s, 1H), 4.49-4.41 (m, 2H), 3.75 (s, 3H), 3.38 (dd, 1H), 3.07 (d, 1H), 2.23-2.04 (m, 2H).

Example 2

1-benzyl 2-methyl(2S,4R)-4-hydroxy-1,2-pyrrolidinedicarboxylate

Chlorobenzylformate (1.0 mL, 7.9 mmol) was added to a mixture of the compound prepared in Example 1 (1.2 g, 6.6 mmol), NaHCO$_3$ (4.0 g) and saturated aqueous NaHCO$_3$ (5.0 mL) in THF (20 mL) at 0° C. After stirring at room temperature for 3 h, tris(hydroxymethyl)aminomethane (1.4 g) was added and the reaction mixture was partitioned between ethyl acetate and water, the combined organic extracts were dried and concentrated and purified by flash chromatography (silica gel, 40 g, 20-80% ethyl acetate/hexanes) to give the title compound (1.3 g, 72%) as a pale yellow oil.

$^1$H NMR (300 MHz, CD$_3$OD, rotamers present) δ 7.35-7.29 (m, 5H), 5.18-4.97 (m, 2H), 4.47-4.39 (m, 2H), 3.71 (s, 1.5H), 3.62-3.51 (m, 3.5H), 2.30-2.25 (m, 1H), 2.09-2.00 (m, 1H).

Example 3

1-benzyl 2-methyl(2S,4S)-4-[4-(methylsulfonyl)-1-piperazinyl]-1,2-pyrrolidinedicarboxylate To a solution of the compound prepared in Example 2 (1.0 g, 3.6 mmol) and N,N-diisopropylethylamine (1.24 mL, 7.16 mmol) in dichloromethane (20 mL) at −20° C. was added trifluoromethylsulfonic anhydride (0.904 g, 5.36 mmol). The reaction mixture was stirred at room temperature for 1 h then concentrated to dryness to obtain the crude triflate. The crude material was dissolved in tert-butanol (50 mL) and N,N-diisopropylethylamine (1.24 mL, 7.16 mmol) and 1-(methylsulfonyl)piperazine (1.76 g, 10.7 mmol) were added to the reaction at room temperature. The resulting mixture was heated at 100° C. for 48 h. After cooling to room temperature, the solvent was removed and the crude reaction mixture was purified by flash chromatography (silica gel, 40 g, 20-60% ethyl acetate/hexanes) to give the title compound (2.35 g, 85%) as an off-white solid.

$^1$H NMR (400 MHz, CDCl$_3$, rotamers present) δ 7.35-7.28 (m, 5H), 5.19-5.00 (m, 2H), 4.15-4.31 (m, 1H), 3.98-3.82 (m, 1H), 3.75 (s, 1.7H), 3.55 (s, 1.3H), 3.33-3.22 (m, 5H), 2.91-2.81 (m, 1H), 2.76 (s, 3H), 2.62-2.46 (m, 5H), 1.91-1.81 (m, 1H).

Example 4

(2S,4S)-1-[(benzyloxy)carbonyl]-4-[4-(methylsulfonyl)-1-piperazinyl]-2-pyrrolidinecarboxylic acid To a solution of the compound prepared in Example 3 (0.90 g, 2.11 mmol) in tetrahydrofuran (20 mL) and water (20 mL) at 0° C. was added lithium hydroxide (0.203 g, 8.4 mmol). The reaction was warmed to room temperature and stirred overnight. The reaction mixture was carefully acidified to pH 5 with 2 M hydrochloric acid. The aqueous solution was extracted with ethyl acetate (2×300 mL) and the combined organic extracts were dried and concentrated to give the title compound (0.565 g, 65%) as a white solid.

$^1$H NMR (400 MHz, CDCl$_3$, rotamers present) δ 7.36-7.33 (m, 5H), 5.18-5.12 (m, 2H), 4.43-4.36 (m, 1H), 3.98-3.82 (m, 2H), 3.37-3.17 (m, 4H), 3.00-2.91 (m, 1H), 2.82-2.71 (m, 6H), 2.64-2.49 (m, 2H), 2.24-2.12 (m, 1H), 1.97-1.85 (m, 1H).

Example 5 benzyl(2S,4S)-2-[(4-{[(2-methyl-2-propanyl)oxy]carbonyl}phenyl)carbamoyl]-4-[4-(methylsulfonyl)-1-piperazinyl]-1-pyrrolidinecarboxylate To a solution of the compound prepared in Example 4 (0.20 g, 0.40 mmol) and 2-methyl-2-propanyl 4-aminobenzoate (0.154 g, 0.80 mmol) in pyridine (50 mL) was added 1-ethyl-3-(3-dimethyllaminopropyl)carbodiimide hydrochloride (0.630 mg 3.2 mmol) at 0° C. The reaction was stirred at room temperature for 18 h. The mixture was concentrated under reduced pressure and the resulting residue diluted with dichloromethane (20 mL). This solution was washed with brine, dried and concentrated. Purification by flash chromatography (silica gel, 40 g, 20-80% ethyl acetate/hexanes) gave the title compound (0.185 g, 65%) as a white solid.

$^1$H NMR (400 MHz, CDCl$_3$, rotamers present) δ 9.15 (br. s, 0.6H), 8.33 (br. s, 0.4H), 7.88 (d, 2H), 7.50 (d, 2H), 7.35-7.01 (m, 5H), 5.22-4.93 (m, 2H), 4.56-4.36 (m, 1H), 3.88-3.76 (m, 1H), 3.22-3.00 (m, 4H), 2.93-2.78 (m, 3H), 2.69-2.48 (m, 6H), 2.45-2.24 (m, 2H), 1.58 (s, 9H).

Example 6

2-methyl-2-propanyl 4-[({(2S,4S)-4-[4-(methylsulfonyl)-1-piperazinyl]-2-pyrrolidinyl}carbonyl)amino]benzoate To a solution of the compound prepared in Example 5 (2.1 g, 7.4 mmol) in ethanol (100 mL) was added Pd/C (0.40 g, 20% by wt). The reaction was stirred under an atmosphere of hydrogen (50 psi) at room temperature for 6 h. The reaction mixture was filtered through diatomaceous earth and concentrated to give the title compound (1.10 g, 69%) as a white solid.

$^1$H NMR (400 MHz, CDCl$_3$) δ 9.85 (s, 1H), 7.95 (d, 2H), 7.63 (d, 2H), 3.95 (dd, 1H), 3.28 (dd, 1H), 3.14 (t, 4H), 2.89-2.85 (m, 1H), 2.83-2.76 (m, 1H), 2.63 (s, 3H), 2.60-2.44 (m, 5H), 2.05 (br. s, 1H), 2.03-1.98 (m, 1H), 1.58 (s, 9H).

Example 7

1-(N,N'-bis{[(2-methyl-2-propanyl)oxy]carbonyl}carbamimidoyl)-4-piperidinecarboxylic acid To a solution of piperidine-4-carboxylic acid trifluoroacetate salt (0.20 g, 0.82 mmol) in methanol (10 mL), triethylamine (0.20 mL, 1.6 mmol) and N,N'-bis{[(2-methyl-2-propanyl)oxy]carbonyl}-1H-pyrazole-1-carboximidamide (0.30 g, 0.98 mmol) was added and the reaction mixture stirred at room temperature for 18 h. The solvent was evaporated under reduced pressure and the resulting residue dissolved in ethyl acetate and washed with brine. The organic layer was dried and concentrated to dryness to obtain the title compound (200 mg, 76%) as a white solid.

$^1$H NMR (400 MHz, DMSO-d$_6$) δ 3.91 (d, 2H), 3.30 (t, 2H), 2.63-2.66 (m, 1H), 1.90-1.96 (m, 2H), 1.67-1.69 (m, 2H), 1.45 (s, 18H).

Example 8

2-methyl-2-propanyl 4-[({(2S,4S)-1-{[1-(N,N'-bis{[(2-methyl-2-propanyl)oxy]carbonyl}carbamimidoyl)-4-piperidinyl]carbonyl}-4-[4-(methylsulfonyl)-1-piperazinyl]-2-pyrrolidinyl}carbonyl)amino]benzoate To a solution of the compound prepared in Example 6 (0.2 g, 0.7 mmol) in N,N-dimethylformamide (2 mL) was added 2-(7-aza-1H-benzotriazole-1-yl)-1,1,3,3-tetramethyluronium hexafluorophosphate (0.10 g, 0.26 mmol) at 0° C.

After stirring for 20 minutes, the compound prepared in Example 7 (0.12 g, 0.26 mmol) and N,N-diisopropylethylamine (0.15 mL, 0.8 mmol) were added and the reaction stirred at room temperature for 2 h. The reaction was quenched by adding ice cold water and the resulting precipitate was collected by filtration, dried and the crude product purified by flash chromatography to afford the title compound (0.11 g, 61%) as a white solid.

$^1$H NMR (400 MHz, CDCl$_3$, rotamers present) δ 9.35 (s, 1H), 7.92 (d, 2H), 7.52 (d, 2H), 4.75 (t, 1H), 4.28-4.10 (m, 2H), 3.88-3.84 (m, 1H), 3.37 (t, 1H), 3.34 (t, 3H), 3.10-2.93 (m, 4H), 2.75 (s, 3H), 2.73-2.57 (m, 6H), 2.30-2.22 (m, 1H), 1.83-1.75 (m, 4H), 1.57 (s, 9H), 1.47 (s, 18H).

Example 9

4-[({(2S,4S)-1-[(1-carbamimidoyl-4-piperidinyl)carbonyl]-4-[4-(methylsulfonyl)-1-piperazinyl]-2-pyrrolidinyl}carbonyl)amino]benzoic acid bis(trifluoroacetate)

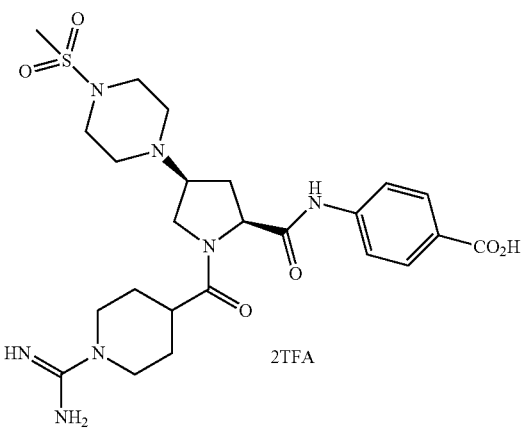 [SMILES: CS(=O)(=O)N1CCN([C@H]2C[C@@H](C(=O)Nc3ccc(C(=O)O)cc3)N(C(=O)C3CCN(C(=N)N)CC3)C2)CC1]

To a solution of the compound prepared in Example 8 (0.11 g, 0.13 mmol) in dichloromethane (15 mL) at 0° C. was added trifluoroacetic acid (0.5 mL). The reaction was warmed to room temperature and stirred for 18 h. The solvent and excess trifluoroacetic acid was removed under reduced pressure. The solid was dissolved in water and lyophilized to dryness to afford the title compound (0.030 g, 40%) as an off-white solid.

$^1$H NMR (400 MHz, CD$_3$OD, rotamers present) 7.97 (d, 2H), 7.69 (d, 2H), 4.55 (t, 1H), 4.26-4.01 (m, 1H), 3.93-3.87 (m, 2H), 3.72 (t, 1H), 3.55-3.51 (m, 1H), 3.41 (br. s, 4H), 3.25-3.04 (m, 6H), 3.05-2.91 (m, 1H), 2.90 (s, 3H), 2.78-2.71 (m, 1H), 2.20-2.06 (m, 1H), 2.00-1.96 (m, 1H), 1.89-1.85 (m, 1H), 1.73-1.67 (m, 2H).

ESI MS m/z 550 (M+H)$^+$

Example 10

4-(N',N''-bis{[(2-methyl-2-propanyl)oxy]carbonyl}carbamimidamido)benzoic acid

To a solution of 4-carbamimidamidobenzoic acid hydrochloride (0.27 g, 1.3 mmol) in ethanol (10 mL), 2 M aqueous NaOH (1.0 mL) and di-tert-butyl dicarbonate (0.68 g, 3.1 mmol) were added and stirred at room temperature overnight. The reaction was concentrated and the residue purified by flash chromatography (silica gel, 20% ethyl acetate/hexanes) to afford the title compound (0.43 g, 75%) as an off-white solid.

$^1$H NMR (300 MHz, DMSO-$d_6$) δ 13.1 (br. s, 1H), 9.05 (br. s, 2H), 7.93 (d, 2H), 7.52 (d, 2H), 1.31 (s, 9H), 1.25 (s, 9H).

Example 11

2-methyl-2-propanyl 4-[({(2S,4S)-1-[4-(N',N''-bis{[(2-methyl-2-propanyl)oxy]carbonyl}carbamimidamido)benzoyl]-4-[4-(methylsulfonyl)-1-piperazinyl]-2-pyrrolidinyl}carbonyl)amino]benzoate Following the procedure described in Example 8, the compound prepared in Example 6 was treated with the compound prepared in Example 10 to give the title compound as a white solid.

$^1$H NMR (400 MHz, CDCl$_3$, rotamers present) δ 9.52 (s, 1H), 7.92 (d, 2H), 7.61 (d, 2H), 7.57 (d, 2H), 7.22 (d, 2H), 5.00 (t, 1H), 3.94-3.90 (m, 1H), 3.45 (t, 1H), 3.29-3.21 (m, 5H), 2.88-2.81 (m, 1H), 2.76 (s, 3H), 2.68-2.59 (m, 4H), 2.54-2.46 (m, 2H), 2.41-2.34 (m, 1H), 1.59 (s, 9H), 1.57 (s, 18H).

Example 12

4-[({(2S,4S)-1-(4-carbamimidamidobenzoyl)-4-[4-(methylsulfonyl)-1-piperazinyl]-2-pyrrolidinyl}carbonyl)amino]benzoic acid bis(trifluoroacetate)

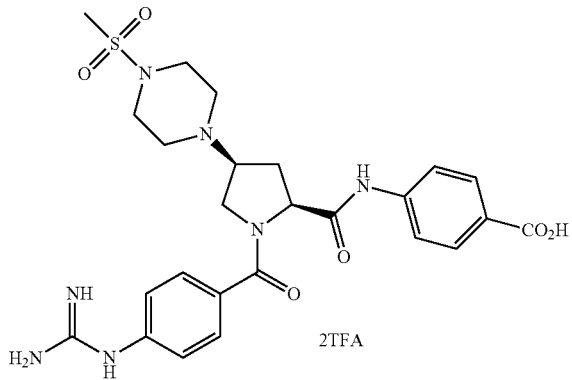 [SMILES: CS(=O)(=O)N1CCN([C@H]2C[C@@H](C(=O)Nc3ccc(C(=O)O)cc3)N(C(=O)c3ccc(NC(=N)N)cc3)C2)CC1]

The compound prepared in Example 11 was treated following the procedure described in Example 9 to give the title compound as an off-white solid.

$^1$H NMR (400 MHz, D$_2$O, rotamers present) δ 8.01 (d, 1H), 7.90 (d, 1H), 7.68 (d, 1H), 7.62 (d, 1H), 7.49 (d, 1H), 7.42 (d, 1H), 7.23-7.20 (m, 2H), 4.84-4.74 (m, 1H), 4.44-4.39 (m, 0.5H), 4.18-4.09 (m, 1H), 3.98-3.95 (m, 1H), 3.87-3.82 (m, 0.5H), 3.66-3.11 (m, 8H), 3.05 (s, 1.5H), 3.01 (m, 1.5H), 3.00-2.95 (m, 1H), 2.38-2.29 (m, 1H). ESI MS m/z 558 (M+H)$^+$ Example 13

2-methyl-2-propanyl 4-[({(2S,4S)-1-({cis-4-[({[(2-methyl-2-propanyl)oxy]carbonyl}amino)methyl]cyclohexyl}carbonyl)-4-[4-(methylsulfonyl)-1-piperazinyl]-2-pyrrolidinyl}carbonyl)amino]benzoate Following the procedure described in Example 8, the compound prepared in Example 6 was treated with cis-4-[({[(2-methyl-2-propanyl)oxy]carbonyl}amino)methyl]cyclohexanecarboxylic acid to give the title compound as a white solid.

$^1$H NMR (400 MHz, CD$_3$OD, rotamers present) δ 7.89 (d, 2H), 7.66 (d, 2H), 4.47 (t, 1H), 4.12-4.04 (m, 1H), 3.48 (t, 2H), 3.33 (t, 4H), 3.24-3.22 (m, 2H), 2.83 (s, 3H), 2.79 (s, 1H), 2.70-2.59 (m, 6H), 2.01 (s, 1H), 1.92-1.80 (m, 6H), 1.58 (s, 9H), 1.43 (s, 9H), 1.23-1.09 (m, 2H).

Example 14

4-[({(2S,4S)-1-{[cis-4-(aminomethyl)cyclohexyl]carbonyl}-4-[4-(methylsulfonyl)-1-piperazinyl]-2-pyrrolidinyl}carbonyl)amino]benzoic acid bis(trifluoroacetate)

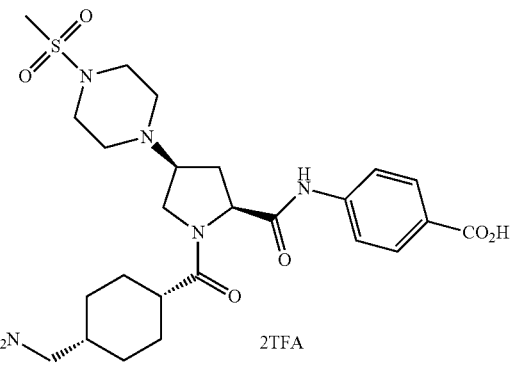

The compound prepared in Example 13 was treated following the procedure described in Example 9 to give the title compound as an off-white solid.

$^1$H NMR (300 MHz, CD$_3$OD, rotamers present) δ 7.97 (d, 2H), 7.71 (d, 2H), 4.55 (t, 1H), 4.17 (t, 1H), 4.19-4.16 (m, 1H), 3.68-3.65 (m, 1H), 3.54-3.53 (m, 6H), 3.07-3.05 (m, 4H), 3.01-2.98 (m, 4H), 2.92-2.89 (m, 2H), 2.05-2.02 (m, 2H), 1.37-1.29 (m, 7H). ESI MS m/z 536 (M+H)$^+$ Example 15

2-methyl-2-propanyl 4-[({(2S,4S)-1-({trans-4-[(1S)-1-({[(2-methyl-2-propanyl)oxy]carbonyl}amino)ethyl]cyclohexyl}carbonyl)-4-[4-(methylsulfonyl)-1-piperazinyl]-2-pyrrolidinyl}carbonyl)amino]benzoate Following the procedure described in Example 8, the compound prepared in Example 6 was treated with trans-4-[(1S)-1-({[(2-methyl-2-propanyl)oxy]carbonyl}amino)ethyl]cyclohexanecarboxylic acid to give the title compound as a light brown solid.

$^1$H NMR (400 MHz, CDCl$_3$) δ 9.46 (s, 1H), 7.90 (d, 2H), 7.52 (d, 2H), 4.77 (t, 1H), 4.34 (d, 1H), 3.86-3.82 (m, 1H), 3.53-3.51 (m, 1H), 3.37 (t, 1H), 3.24-3.22 (m, 4H), 2.95-2.88 (m, 1H), 2.78 (s, 3H), 2.74-2.70 (m, 2H), 2.69-2.56 (m, 4H), 2.35-2.34 (m, 1H), 2.26-2.19 (m, 1H), 1.92-1.81 (m, 4H), 1.62 (s, 9H), 1.58-1.49 (m, 2H), 1.48 (s, 9H), 1.31-1.24 (m, 1H), 1.10 (d, 3H), 1.06-1.04 (m, 1H).

Example 16

4-[({(2S,4S)-1-({trans-4-[(1S)-1-aminoethyl]cyclohexyl}carbonyl)-4-[4-(methylsulfonyl)-1-piperazinyl]-2-pyrrolidinyl}carbonyl)amino]benzoic acid bis(trifluoroacetate)

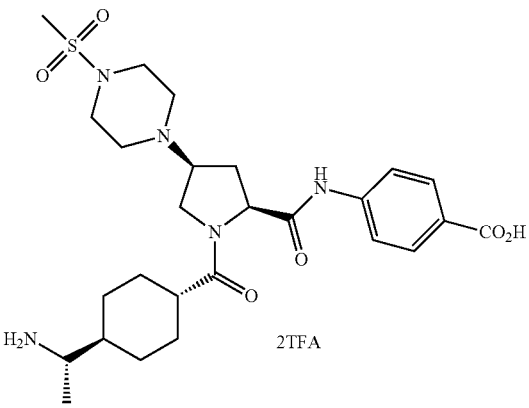 [SMILES: C[C@H](N)[C@H]1CC[C@H](C(=O)N2C[C@@H](N3CCN(S(C)(=O)=O)CC3)C[C@H]2C(=O)Nc2ccc(C(=O)O)cc2)CC1]

The compound prepared in Example 15 was treated following the procedure described in Example 9 to give the title compound as a brown solid.

$^1$H NMR (400 MHz, CD$_3$OD) δ 7.98 (d, 2H), 7.70 (d, 2H), 4.54 (t, 1H), 4.25-4.20 (m, 1H), 3.76 (t, 1H), 3.59-3.55 (m, 1H), 3.43-3.34 (m, 4H), 3.29-3.08 (m, 6H), 2.91 (s, 3H), 2.70-2.65 (m, 1H), 2.60-2.54 (m, 1H), 2.16-2.11 (m, 1H), 2.09-2.03 (m, 1H), 1.91-1.84 (m, 4H), 1.58-1.42 (m, 3H), 1.27 (d, 3H).

ESI MS m/z 550 (M+H)$^+$

Example 17 methyl 4-(N-{[(2-methyl-2-propanyl)oxy]carbonyl}carbamimidoyl)benzoate

To a solution of methyl 4-(N-carbamimidoyl)benzoate (2.18 g, 9.18 mmol) and triethylamine (1.02 mL, 7.32 mmol) in anhydrous methanol (100 mL) was added di-tert-butyl dicarbonate (3.0 g, 13.8 mmol). The mixture was heated at 40° C. under nitrogen for 5 h. The reaction mixture was cooled and then concentrated under reduced pressure. The resulting residue was diluted with ethyl acetate (100 mL) and washed with aqueous sodium bicarbonate solution. The aqueous layer was then extracted with dichloromethane (2×30 mL). The combined organic extracts were dried and concentrated. Purification by flash chromatography (silica gel, 80 g, 0-30% ethyl acetate/hexanes) afforded the title compound (1.98 g, 77%) as a white solid.

$^1$H NMR (500 MHz, CDCl$_3$, Amidine NH protons were not observed.) δ 8.09 (d, 2H), 7.91 (d, 2H), 3.94 (s, 3H), 1.55 (s, 9H).

Example 18

4-(N-{[(2-methyl-2-propanyl)oxy]carbonyl}carbamimidoyl)benzoic acid

To a solution of the compound prepared in Example 17 (0.20 g, 0.72 mmol) in methanol (10 mL) was added 1 M aqueous sodium hydroxide (5 mL). The reaction was stirred at room temperature for 1 h. The mixture was concentrated and the resulting aqueous residue was diluted with ethyl acetate. The aqueous layer was acidified with 1 M hydrochloric acid to pH 4-5 and extracted with ethyl acetate (2×20 mL). The combined organic extracts were dried and concentrated to give the title compound (0.208 g, >99%) as a white solid.

$^1$H NMR (500 MHz, DMSO-d$_6$) δ 8.98 (app. s, 3H), 8.00 (app. s, 4H), 1.44 (s, 9H).

ESI MS m/z 263 (M+H)$^+$

Example 19

2-methyl-2-propanyl 4-[({(2S,4S)-1-[4-(N-{[(2-methyl-2-propanyl)oxy]carbonyl}carbamimidoyl)benzoyl]-4-[4-(methylsulfonyl)-1-piperazinyl]-2-pyrrolidinyl}carbonyl)amino]benzoate Following the procedure described in Example 8, the compound prepared in Example 6 was treated with the compound prepared in Example 18 to give the title compound as a white solid.

$^1$H NMR (400 MHz, CDCl$_3$, rotamers present) δ 9.47 (s, 1H), 7.93-7.89 (m, 4H), 7.61-7.56 (m, 4H), 4.97 (t, 1H), 3.69-3.64 (m, 1H), 3.41 (t, 1H), 3.28-3.19 (m, 4H), 2.87-2.80 (m, 1H), 2.77 (s, 3H), 2.65-2.60 (m, 3H), 2.48-2.34 (m, 3H), 1.57 (s, 9H), 1.54 (s, 9H).

Example 20

4-[({(2S,4S)-1-(4-carbamimidoylbenzoyl)-4-[4-(methylsulfonyl)-1-piperazinyl]-2-pyrrolidinyl}carbonyl)amino]benzoic acid bis(trifluoroacetate)

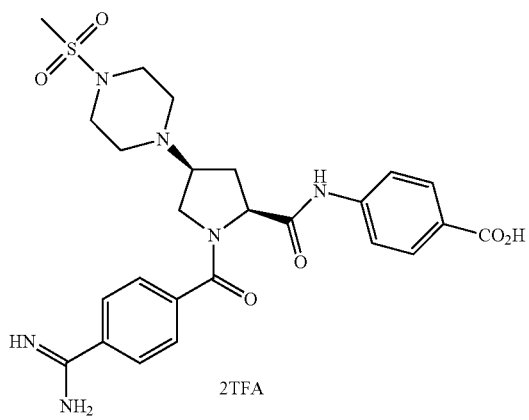 [SMILES: CS(=O)(=O)N1CCN([C@H]2C[C@@H](C(=O)Nc3ccc(C(=O)O)cc3)N(C(=O)c3ccc(C(=N)N)cc3)C2)CC1]

The compound prepared in Example 19 was treated following the procedure described in Example 9 to give the title compound as an off-white solid.

$^1$H NMR (400 MHz, D$_2$O, rotamers present) δ 9.47 (s, 1H), 8.01-7.61 (m, 7H), 7.17 (d, 1H), 4.84-4.76 (m, 1H), 4.09-3.81 (m, 2H), 3.62-3.44 (m, 6H), 3.43-3.25 (m, 2H), 3.04-3.00 (m, 4H), 2.36-2.29 (m, 1H).

ESI MS m/z 543 (M+H)$^+$

Example 21 methyl trans-4-carbamoylcyclohexanecarboxylate

To a cooled (−10° C.) solution of trans-4-(methoxycarbonyl)cyclohexane-1-carboxylic acid (1.01 g, 5.43 mmol) in tetrahydrofuran (25 mL) was sequentially added triethylamine (1.50 mL, 10.9 mmol) and ethyl chloroformate (0.60 mL, 6.2 mmol) under a nitrogen atmosphere and the reaction mixture stirred at room temperature for 3 h. The reaction was then cooled to −10° C., ammonium hydroxide (5.0 mL, 33 mmol) was added and the reaction mixture warmed to room temperature and stirred overnight whereupon the mixture was diluted with water and extracted with ethyl acetate (3×50 mL). The combined organic extracts were dried and concentrated to give the title compound (0.84 g, 84%) as a white solid.

$^1$H NMR (400 MHz, DMSO-$d_6$) δ 7.17 (s, 1H), 6.66 (s, 1H), 3.58 (s, 3H), 2.29-2.20 (m, 1H), 2.07-1.98 (m, 1H), 1.94-1.86 (m, 2H), 1.81-1.71 (m, 2H), 1.39-1.23 (m, 4H).

Example 22 methyl trans-4-cyanocyclohexanecarboxylate

To a solution of the compound prepared in Example 21 (0.84 g, 4.6 mmol) in pyridine (20 mL) was added imidazole (1.0 g, 4.6 mmol) and phosphorousoxychloride (1.0 mL) in one portion at 0° C. under a nitrogen atmosphere. The reaction mixture was stirred at room temperature for 4 h whereupon the reaction was quenched with water and extracted with ethyl acetate. The organic extract was washed with 2 M hydrochloric acid, dried and concentrated to give the title compound (0.76 g, 99%) as a white solid.

$^1$H NMR (300 MHz, DMSO-$d_6$) δ 3.58 (s, 3H), 2.71 (t, 1H), 2.38 (t, 1H), 2.05-1.80 (m, 4H), 1.63-1.29 (m, 4H).

Example 23 trans-4-cyanocyclohexanecarboxylic acid

To a solution of the compound prepared in Example 22 (0.200 g, 1.19 mmol) in tetrahydrofuran (5.0 mL), methanol (1.0 mL) and water (5.0 mL) at 0° C. was added lithium hydroxide (0.073 g, 1.79 mmol). The reaction was warmed to room temperature and stirred overnight whereupon the mixture was carefully acidified to pH 5.0 with 2 N hydrochloric acid and extracted with ethyl acetate (2×300 mL). The combined organic extracts were dried and concentrated to give the title compound (0.15 g, 82%) as a white solid.

$^1$H NMR (400 MHz, DMSO-$d_6$) δ 12.14 (br. s, 1H), 2.72-2.65 (m, 1H), 2.29-2.22 (m, 1H), 2.0-1.95 (m, 2H), 1.90-1.82 (m, 2H), 1.57-1.47 (m, 2H), 1.41-1.34 (m, 2H).

Example 24

2-methyl-2-propanyl 4-[({(2S,4S)-1-[(trans-4-cyanocyclohexyl)carbonyl]-4-[4-(methylsulfonyl)-1-piperazinyl]-2-pyrrolidinyl}carbonyl)amino]benzoate Following the procedure described in Example 8, the compound prepared in Example 23 was treated with the compound prepared in Example 6 to give the title compound as a white solid.

$^1$H NMR (400 MHz, CDCl$_3$, rotamers present) δ 10.20 (s, 1H), 7.83 (d, 2H), 7.67 (d, 2H), 4.34 (t, 1H), 4.03 (t, 1H), 3.10 (m, 5H), 2.86 (s, 3H), 2.73-2.56 (m, 4H), 2.05-2.01 (m, 2H), 1.90-1.61 (m, 4H), 1.53 (s, 11H), 1.41-1.15 (m, 4H), 1.01-0.96 (m, 1H).

Example 25 ethyl 4-[({(2S,4S)-1-[(trans-4-carbamimidoylcyclohexyl)carbonyl]-4-[4-(methylsulfonyl)-1-piperazinyl]-2-pyrrolidinyl}carbonyl)amino]benzoate hydrochloride Anhydrous HCl gas was bubbled into a solution of the compound prepared in Example 24 (0.11 g, 0.18 mmol) in ethanol (15 mL) at 0° C. for 30 min and the reaction mixture was stirred overnight. 7 M ammonia in methanol was added to the reaction mixture. After stirring for 5 h, the excess ammonia was evaporated to afford the title compound (0.070 g, 65%) which was used without further purification.

ESI MS m/z 577 (M+H)$^+$

Example 26

4-[({(2S,4S)-1-[(trans-4-carbamimidoylcyclohexyl)carbonyl]-4-[4-(methylsulfonyl)-1-piperazinyl]-2-pyrrolidinyl}carbonyl)amino]benzoic acid bis(trifluoroacetate)

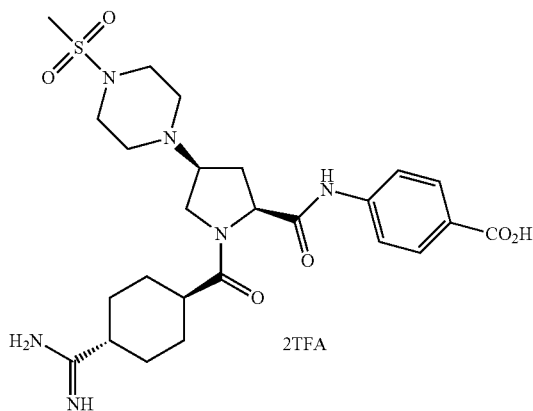 [SMILES: CS(=O)(=O)N1CCN([C@H]2C[C@@H](C(=O)Nc3ccc(C(=O)O)cc3)N(C(=O)[C@H]3CC[C@H](C(=N)N)CC3)C2)CC1]

To a solution of the compound prepared in Example 25 (0.070 g, 0.12 mmol) in water (0.5 mL) was added 2 M hydrochloric acid (1.0 mL) at 0° C. and the reaction was warmed to room temperature and stirred for 4 h. Solvent was evaporated and the crude compound was purified by Prep-HPLC (0.1% TFA containing CH$_3$CN—H$_2$O gradient) to provide the title compound (0.014 g, 21%) as an off-white solid.

$^1$H NMR (400 MHz, CD$_3$OD, rotamers present) 7.98 (d, 2H), 7.70 (d, 2H), 4.54 (t, 1H), 4.22-4.18 (m, 1H), 3.70 (t, 1H), 3.50-3.35 (m, 5H), 3.14-2.99 (m, 4H), 2.9 (s, 3H), 2.73-2.65 (m, 2H), 2.49-2.33 (m, 1H), 2.10-1.96 (m, 5H), 1.67-1.54 (m, 4H).

ESI MS m/z 549 (M+H)$^+$

Example 27 benzyl 4-(N,N'-bis{[(2-methyl-2-propanyl)oxy]carbonyl}carbamimidoyl)-1-piperazinecarboxylate Following the procedure described in Example 7, the reaction of N,N'-bis{[(2-methyl-2-propanyl)oxy]carbonyl}-1H-pyrazole-1-carboximidamide (0.25 g, 1.1 mmol), triethylamine (0.5 mL, 3.4 mmol) and benzyl piperazine-1-carboxylate (0.422 g, 1.36 mmol) in methanol (10 mL) gave the title compound (0.256 g, 50%) as a colorless liquid.

¹H NMR (400 MHz, DMSO-d₆) δ 9.63 (br. s, 1H), 7.52-7.34 (m, 5H), 5.10 (s, 2H), 3.42-3.40 (m, 8H), 1.36 (s, 18H).

Example 28 bis(2-methyl-2-propanyl) (1-piperazinylmethylylidene)biscarbamate

To a solution of the compound prepared in Example 27 (0.045 g, 0.056 mmol) in ethanol (10 mL) was added Pd/C (20% by wt, 0.010 g). The reaction was stirred under an atmosphere of hydrogen (40 psi) at room temperature for 2 h. The reaction mixture was filtered through diatomaceous earth and the filtrate concentrated to afford the title compound (0.03 g, 69%) as a pale green solid.
¹H NMR (400 MHz, DMSO-d₆) δ 9.53 (br. s, 1H), 5.09 (s, 1H), 3.42-3.41 (m, 4H), 2.66-2.64 (m, 4H), 1.43 (s, 18H).

Example 29

2-methyl-2-propanyl 4-[({(2S,4S)-1-{[4-(N,N'-bis{[(2-methyl-2-propanyl)oxy]carbonyl}carbamimidoyl)-1-piperazinyl]carbonyl}-4-[4-(methylsulfonyl)-1-piperazinyl]-2-pyrrolidinyl}carbonyl)amino]benzoate To a solution of the compound prepared in Example 28 (0.05 g, 0.15 mmol) in THF (10 mL), triphosgene (0.054 g, 0.182 mmol) and N,N-diisopropylethylamine (0.08 mL, 0.456 mmol) were added at 0° C. and the reaction mixture warmed to room temperature. After stirring for 1 h, the reaction mixture was concentrated to dryness and the crude residue was dissolved in THF. To this mixture, the compound prepared in Example 6 (0.065 g, 0.152 mmol) and N,N-diisopropylethylamine (0.08 mL, 0.456 mmol) were added at 0° C., and the reaction warmed to room temperature. After stirring for 4 h, the mixture was diluted with ice cold water and extracted with ethyl acetate (2×50 mL). The organic layer was washed with brine, dried and concentrated. Purification by flash chromatography (silica gel, 40 g, 20-60% ethyl acetate/hexanes) provided the title compound (0.045 g, 39%) as a white solid.
¹H NMR (400 MHz, CD₃OD, rotamers present) δ 7.89 (d, 2H), 7.67 (d, 2H), 4.65-4.62 (m, 1H), 4.11-4.09 (m, 1H), 3.75-3.71 (m, 2H), 3.52-3.49 (m, 8H), 3.23 (t, 4H), 2.86-2.85 (m, 1H), 2.83 (s, 3H), 2.71-2.62 (m, 5H), 1.61 (s, 9H), 1.47 (s, 18H).

Example 30

4-[({(2S,4S)-1-[(4-carbamimidoyl-1-piperazinyl)carbonyl]-4-[4-(methylsulfonyl)-1-piperazinyl]-2-pyrrolidinyl}carbonyl)amino]benzoic acid bis(trifluoroacetate)

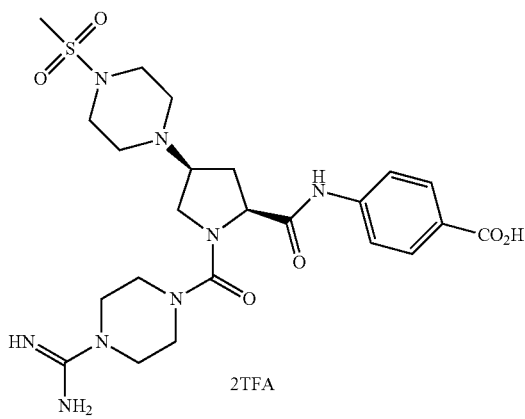 [SMILES: CS(=O)(=O)N1CCN([C@H]2C[C@@H](C(=O)Nc3ccc(C(=O)O)cc3)N(C(=O)N3CCN(C(=N)N)CC3)C2)CC1]

The compound prepared in Example 29 was treated following the procedure described in Example 9 to give the title compound as an off-white solid.
¹H NMR (400 MHz, CD₃OD, rotamers present) δ 7.84 (d, 2H), 7.71 (d, 2H), 4.69-4.67 (m, 1H), 3.88-3.84 (m, 1H), 3.64-3.55 (m, 5H), 3.54-3.52 (m, 2H), 3.50-3.49 (m, 2H), 3.48-3.38 (m, 5H), 3.03-3.02 (m, 2H), 2.99-2.89 (s, 3H), 2.72 (m, 2H), 1.37-1.12 (m, 2H).
ESI MS m/z 551 (M+H)⁺

Example 31

2-methyl-2-propanyl 4-[({(2S,4S)-1-({trans-4-[({[(2-methyl-2-propanyl)oxy]carbonyl}amino)methyl]cyclohexyl}carbonyl)-4-[4-(methylsulfonyl)-1-piperazinyl]-2-pyrrolidinyl}carbonyl)amino]benzoate Following the procedure described in Example 8, the compound prepared in Example 6 was treated with trans-4-[({[(2-methyl-2-propanyl)oxy]carbonyl}amino)methyl]cyclohexanecarboxylic acid to give the title compound as a white solid.
¹H NMR (400 MHz, CD₃OD, rotamers present) δ 7.89 (d, 2H), 7.66 (d, 2H), 4.47 (t, 1H), 4.12-4.04 (m, 1H), 3.48 (t, 2H), 3.33 (t, 4H), 3.24-3.22 (m, 2H), 2.83 (s, 3H), 2.79 (s, 1H), 2.70-2.59 (m, 6H), 2.01 (s, 1H), 1.92-1.80 (m, 6H), 1.58 (s, 9H), 1.43 (s, 9H), 1.23-1.09 (m, 2H).

Example 32

4-[({(2S,4S)-1-{[trans-4-(aminomethyl)cyclohexyl]carbonyl}-4-[4-(methylsulfonyl)-1-piperazinyl]-2-pyrrolidinyl}carbonyl)amino]benzoic acid bis(trifluoroacetate)

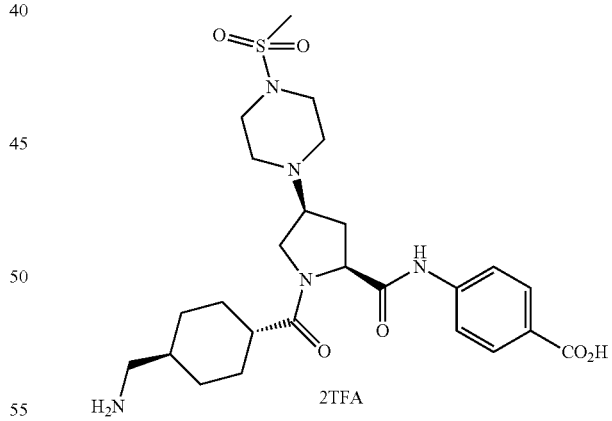

The compound prepared in Example 31 was treated following the procedure described in Example 9 to give the title compound as a white solid.
¹H NMR (500 MHz, CD₃OD, rotamers present) δ 7.98 (d, 2H), 7.71 (d, 2H), 4.59 (t, 1H), 4.37-4.26 (m, 1H), 3.99-3.84 (m, 2H), 3.54 (br. s, 4H), 3.43 (br. s, 4H), 2.96 (s, 3H), 2.88-2.77 (m, 3H), 2.60 (tt, 1H), 2.37-2.22 (m, 1H), 2.03-1.96 (m, 1H), 1.96-1.83 (m, 3H), 1.69-1.56 (m, 1H), 1.56-1.41 (m, 2H), 1.21-1.10 (m, 2H).
ESI MS m/z 536 (M+H)⁺

Example 33

4-({[(2S,4S)-1-{[trans-4-(aminomethyl)cyclohexyl]carbonyl}-4-(4-morpholinyl)-2-pyrrolidinyl]carbonyl}amino)benzoic acid bis(trifluoroacetate)

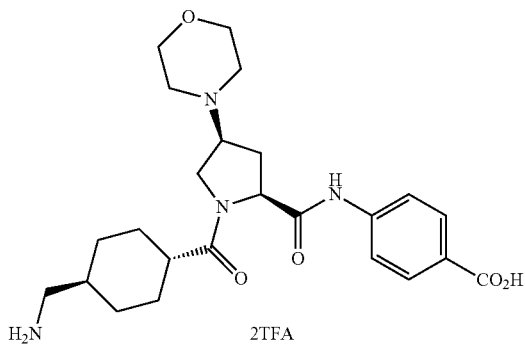 [SMILES: NC[C@H]1CC[C@H](C(=O)N2C[C@@H](N3CCOCC3)C[C@H]2C(=O)Nc2ccc(C(=O)O)cc2)CC1]

The compound prepared in Example 2 was treated following the procedures described in Examples 3, 4, 5, 6, 31 and 32 to give the title compound having the following physical properties. (Note: in the step corresponding to Example 3 in the operation, morpholine was used in place of 1-(methylsulfonyl)piperazine)

$^1$H NMR (250 MHz, CD$_3$OD, rotamers present) δ 7.98 (d, 2H), 7.71 (d, 2H), 4.60 (t, 1H), 4.43-4.28 (m, 1H), 4.15-3.79 (m, 6H), 3.44 (br. s, 4H), 2.92-2.76 (m, 3H), 2.75-2.50 (m, 1H), 2.41-2.24 (m, 1H), 2.07-1.80 (m, 4H), 1.80-1.35 (m, 3H), 1.27-1.02 (m, 2H).

ESI MS m/z 459 (M+H)$^+$

Example 34

4-({[(3'S,5'S)-1'-{[trans-4-(aminomethyl)cyclohexyl]carbonyl}-1,3'-bipyrrolidin-5'-yl]carbonyl}amino)benzoic acid bis(trifluoroacetate)

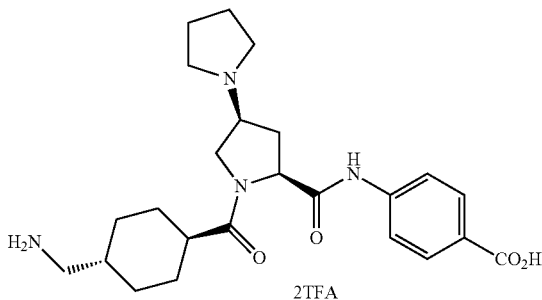 [SMILES: NC[C@H]1CC[C@H](C(=O)N2C[C@@H](N3CCCC3)C[C@H]2C(=O)Nc2ccc(C(=O)O)cc2)CC1]

The compound prepared in Example 2 was treated following the procedures described in Examples 3, 4, 5, 6, 31 and 32 to give the title compound having the following physical properties. (Note: in the step corresponding to Example 3 in the operation, pyrrolidine was used in place of 1-(methylsulfonyl)piperazine).

$^1$H NMR (500 MHz, CD$_3$OD, rotamers present) δ 7.98 (d, 2H), 7.72 (d, 2H), 4.62 (dd, 1H), 4.26 (dd, 1H), 4.06 (quint., 1H), 3.98 (dd, 1H), 3.73 (br. s, 2H), 3.28 (br. s, 2H), 2.87-2.77 (m, 3H), 2.59 (tt, 1H), 2.38-2.31 (m, 1H), 2.14 (br. s, 4H), 2.01-1.83 (m, 4H), 1.69-1.58 (m, 1H), 1.53-1.41 (m, 2H), 1.21-1.09 (m, 2H).

ESI MS m/z 443 (M+H)$^+$

Example 35

4-({[(2S,4S)-1-{[trans-4-(aminomethyl)cyclohexyl]carbonyl}-4-(1-piperidinyl)-2-pyrrolidinyl]carbonyl}amino)benzoic acid bis(trifluoroacetate)

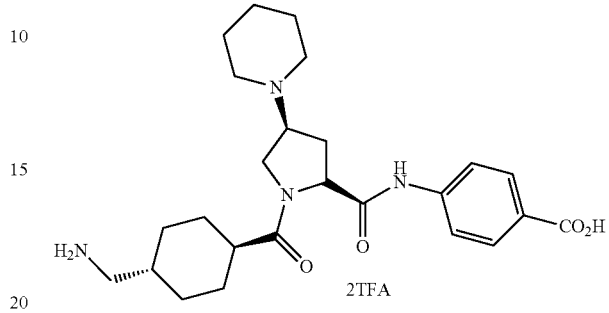

The compound prepared in Example 2 was treated following the procedures described in Examples 3, 4, 5, 6, 31 and 32 to give the title compound having the following physical properties. (Note: in the step corresponding to Example 3 in the operation, piperidine was used in place of 1-(methylsulfonyl)piperazine).

$^1$H NMR (500 MHz, CD$_3$OD, rotamers present) δ 7.98 (d, 2H), 7.71 (d, 2H), 4.57 (t, 1H), 4.37 (dd, 1H), 3.99 (quint., 1H), 3.87 (t, 1H), 3.65 (br. s, 2H), 3.05 (br. s, 2H), 2.87 (ddd, 1H), 2.80 (d, 2H), 2.60 (tt, 1H), 2.29-2.20 (m, 1H), 2.07-1.71 (m, 9H), 1.69-1.57 (m, 1H), 1.57-1.39 (m, 3H), 1.22-1.09 (m, 2H).

ESI MS m/z 457 (M+H)$^+$

Example 36

4-({[(2S,4S)-1-{[trans-4-(aminomethyl)cyclohexyl]carbonyl}-4-(3-oxo-1-piperazinyl)-2-pyrrolidinyl]carbonyl}amino)benzoic acid bis(trifluoroacetate)

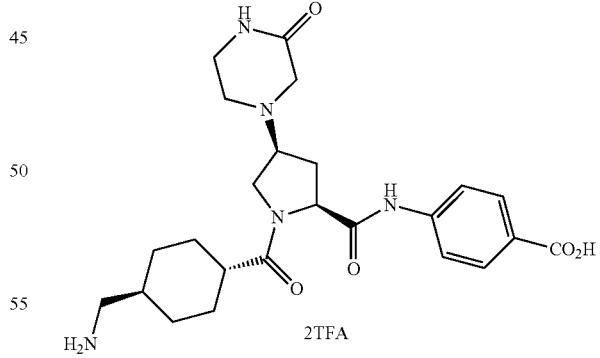

The compound prepared in Example 2 was treated following the procedures described in Examples 3, 4, 5, 6, 31 and 32 to give the title compound having the following physical properties. (Note: in the step corresponding to Example 3, 2-oxopiperazine was used in place of 1-(methylsulfonyl)piperazine)

$^1$H NMR (500 MHz, CD$_3$OD, rotamers present) δ 7.98 (d, 2H), 7.71 (d, 2H), 4.56 (t, 1H), 4.24 (dd, 1H), 3.81 (dd, 1H), 3.75-3.60 (m, 3H), 3.50 (dd, 2H), 3.39-3.31 (m, 1H), 3.27-.

3.19 (m, 1H), 2.80 (d, 2H), 2.80-2.71 (m, 1H), 2.60 (tt, 1H), 2.20 (dt, 1H), 2.03-1.95 (m, 1H), 1.95-1.83 (m, 3H), 1.69-1.58 (m, 1H), 1.54-1.40 (m, 2H), 1.21-1.09 (m, 2H).
ESI MS m/z 472 (M+H)+

Example 37

4-({[(2S,4S)-1-{(2E)-3-[5-chloro-2-(1H-tetrazol-1-yl)phenyl]-2-propenoyl}-4-(4-morpholinyl)-2-pyrrolidinyl]carbonyl}amino)benzoic acid trifluoroacetate

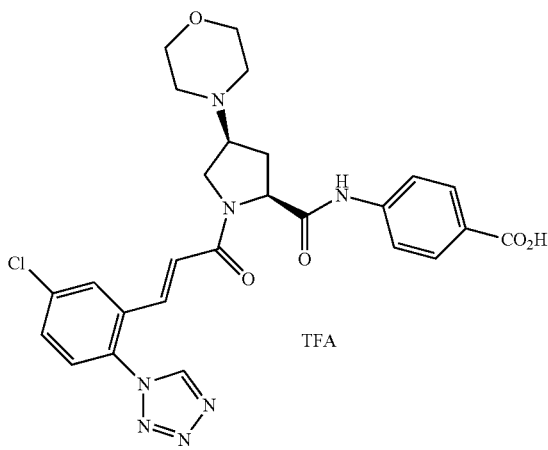 [SMILES: O=C(O)c1ccc(NC(=O)[C@@H]2C[C@H](N3CCOCC3)CN2C(=O)/C=C/c2cc(Cl)ccc2-n2cnnn2)cc1]

The compound prepared in Example 2 was treated following the procedures described in Examples 3, 4, 5, 6, 8 and 9 to give the title compound having the following physical properties. (Note: in the step corresponding to Example 3, morpholine was used in place of 1-(methylsulfonyl)piperazine. In the step corresponding to Example 8, (2E)-3-[5-chloro-2-(1H-tetrazol-1-yl)phenyl]acrylic acid was used in place of 1-(N,N'-bis{[(2-methyl-2-propanyl)oxy]carbonyl}carbamimidoyl)-4-piperidinecarboxylic acid).
$^1$H NMR (500 MHz, CD$_3$OD, rotamers present) δ 9.53 (s, 1H), 8.15 (d, 1H), 7.98 (d, 2H), 7.70 (d, 2H), 7.68 (dd, 1H), 7.59 (d, 1H), 7.18 (d, 1H), 7.05 (d, 1H), 4.70 (t, 1H), 4.41 (dd, 1H), 4.17-3.84 (m, 6H), 3.45 (br. s, 4H), 2.90-2.81 (m, 1H), 2.46-2.36 (m, 1H).
ESI MS m/z 552 (M+H)+

Example 38 methyl 4-({[(2S,4S)-1-{(2E)-3-[5-chloro-2-(1H-tetrazol-1-yl)phenyl]-2-propenoyl}-4-(4-morpholinyl)-2-pyrrolidinyl]carbonyl}amino)benzoate

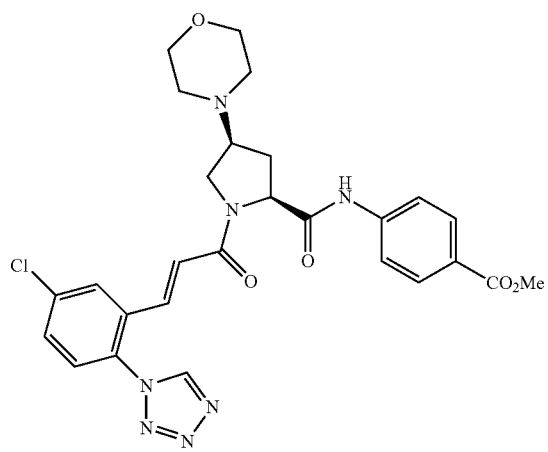 [SMILES: COC(=O)c1ccc(NC(=O)[C@@H]2C[C@H](N3CCOCC3)CN2C(=O)/C=C/c2cc(Cl)ccc2-n2cnnn2)cc1]

The compound prepared in Example 2 was treated following the procedures described in Examples 3, 4, 5, 6 and 8 to give the title compound having the following physical properties. (Note: in the step corresponding to Example 3, morpholine was used in place of 1-(methylsulfonyl)piperazine. In the step corresponding to Example 5, methyl 4-aminobenzoate was used in place of tert-butyl 4-aminobenzoate. In the step corresponding to Example 8, (2E)-3-[5-chloro-2-(1H-tetrazol-1-yl)phenyl]acrylic acid was used in place of 1-(N,N'-bis{[(2-methyl-2-propanyl)oxy]carbonyl}carbamimidoyl)-4-piperidinecarboxylic acid).
$^1$H NMR (500 MHz, DMSO-d$_6$, rotamers present) δ 10.38 (s, 1H), 9.85 (s, 1H), 8.36 (d, 1H), 7.91 (d, 2H), 7.76 (dd, 1H), 7.74-7.67 (m, 3H), 7.28 (d, 1H), 6.85 (d, 1H), 4.44 (dd, 1H), 4.28 (dd, 1H), 3.82 (s, 3H), 3.65-3.55 (m, 4H), 3.41 (t, 1H), 2.93-2.83 (m, 1H), 2.52-2.40 (m, 5H), 1.70 (q, 1H).
ESI MS m/z 566 (M+H)+

Example 39

(2S,4S)-1-{(2E)-3-[5-chloro-2-(1H-tetrazol-1-yl)phenyl]-2-propenoyl}-N-phenyl-4-[4-(phenylsulfonyl)-1-piperazinyl]-2-pyrrolidinecarboxamide

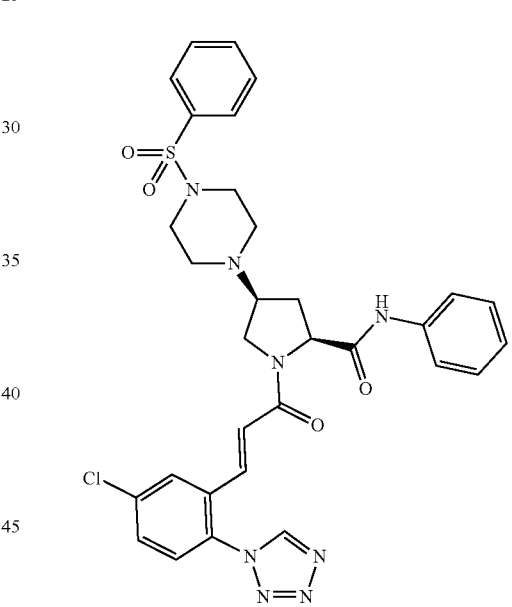

The compound prepared in Example 2 was treated following the procedures described in Example 3, 4, 5, 6 and 8 to give the title compound having the following physical properties. (Note: in the step corresponding to Example 3, 1-benzenesulfonyl-piperazine was used in place of 1-(methylsulfonyl)piperazine. In the step corresponding to Example 5, aniline was used in place of tert-butyl 4-aminobenzoate. In the step corresponding to Example 8, (2E)-3-[5-chloro-2-(1H-tetrazol-1-yl)phenyl]acrylic acid was used in place of 1-(N,N'-bis{[(2-methyl-2-propanyl)oxy]carbonyl}carbamimidoyl)-4-piperidinecarboxylic acid).
$^1$H NMR (500 MHz, DMSO-d$_6$, rotamers present) δ 10.02 (s, 1H), 9.85 (s, 1H), 8.34 (d, 1H), 7.78-7.69 (m, 5H), 7.67 (t, 2H), 7.52 (d, 2H), 7.30-7.22 (m, 3H), 7.01 (t, 1H), 6.83 (d, 1H), 4.40 (t, 1H), 4.26 (dd, 1H), 3.31 (dd, 1H), 2.94-2.85 (m, 5H), 2.62-2.49 (m, 4H), 2.47-2.38 (m, 1H), 1.60 (dd, 1H).
ESI MS m/z 647 (M+H)+

Example 40

(2S,4S)-1-{(2E)-3-[5-chloro-2-(1H-tetrazol-1-yl)phenyl]-2-propenoyl}-N-[4-(methylsulfonyl)phenyl]-4-(4-morpholinyl)-2-pyrrolidinecarboxamide

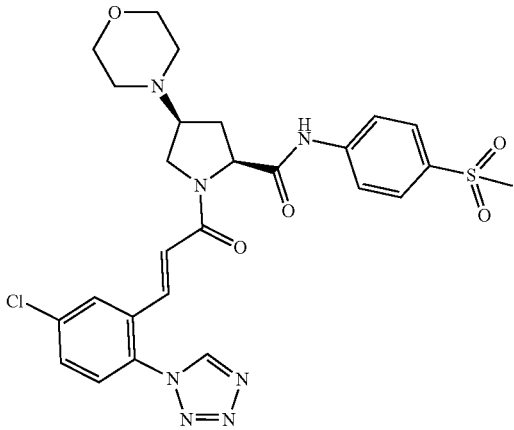 [SMILES: CS(=O)(=O)c1ccc(NC(=O)[C@@H]2C[C@H](N3CCOCC3)CN2C(=O)/C=C/c2cc(Cl)ccc2-n2cnnn2)cc1]

The compound prepared in Example 2 was treated following the procedures described in Examples 3, 4, 5, 6 and 8 to give the title compound having the following physical properties. (Note: in the step corresponding to Example 3, morpholine was used in place of 1-(methylsulfonyl)piperazine. In the step corresponding to Example 5, 4-(methanesulfonyl)aniline was used in place of tert-butyl 4-aminobenzoate. In the step corresponding to Example 8, (2E)-3-[5-chloro-2-(1H-tetrazol-1-yl)phenyl]acrylic acid was used in place of 1-(N,N'-bis{[(2-methyl-2-propanyl)oxy]carbonyl}carbamimidoyl)-4-piperidinecarboxylic acid).

$^1$H NMR (500 MHz, DMSO-$d_6$, rotamers present) δ 10.49 (s, 1H), 9.85 (s, 1H), 8.36 (d, 1H), 7.85 (d, 2H), 7.81 (d, 2H), 7.76 (dd, 1H), 7.72 (d, 1H), 7.28 (d, 1H), 6.85 (d, 1H), 4.44 (t, 1H), 4.29 (dd, 1H), 3.60 (br. s, 4H), 3.41 (t, 1H), 3.15 (s, 3H), 2.94-2.84 (m, 1H), 2.46 (app. br. s, 5H), 1.70 (dd, 1H).

ESI MS m/z 586 (M+H)$^+$

Example 41

(2S,4S)-1-{(2E)-3-[5-chloro-2-(1H-tetrazol-1-yl)phenyl]-2-propenoyl}-4-(4-morpholinyl)-N-(3-pyridinyl)-2-pyrrolidinecarboxamide

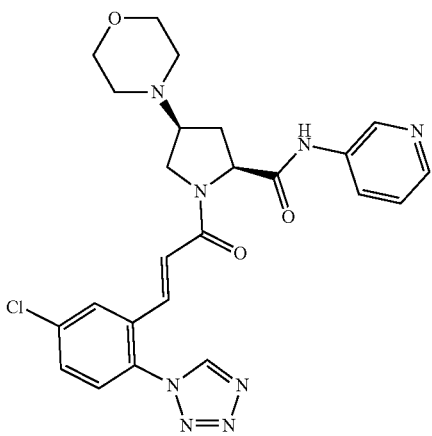 [SMILES: O=C(Nc1cccnc1)[C@@H]1C[C@H](N2CCOCC2)CN1C(=O)/C=C/c1cc(Cl)ccc1-n1cnnn1]

The compound prepared in Example 2 was treated following the procedures described in Examples 3, 4, 5, 6 and 8 to give the title compound having the following physical properties. (Note: in the step corresponding to Example 3, morpholine was used in place of 1-(methylsulfonyl)piperazine. In the step corresponding to Example 5, 3-aminopyridine was used in place of tert-butyl 4-aminobenzoate. In the step corresponding to Example 8, (2E)-3-[5-chloro-2-(1H-tetrazol-1-yl)phenyl]acrylic acid was used in place of 1-(N,N'-bis{[(2-methyl-2-propanyl)oxy]carbonyl}carbamimidoyl)-4-piperidinecarboxylic acid).

$^1$H NMR (500 MHz, DMSO-$d_6$, rotamers present) δ 10.26 (s, 1H), 9.86 (s, 1H), 8.72 (d, 1H), 8.36 (d, 1H), 8.25 (d, 1H), 8.01 (d, 1H), 7.76 (dd, 1H), 7.72 (d, 1H), 7.33 (dd, 1H), 7.28 (d, 1H), 6.86 (d, 1H), 4.43 (t, 1H), 4.28 (dd, 1H), 3.60 (br. s, 4H), 3.41 (t, 1H), 2.93-2.83 (m, 1H), 2.53-2.30 (m, 5H), 1.71 (dd, 1H).

ESI MS m/z 509 (M+H)$^+$

Example 42

(2S,4S)-1-{(2E)-3-[5-chloro-2-(1H-tetrazol-1-yl)phenyl]-2-propenoyl}-N-(4-methoxyphenyl)-4-(4-morpholinyl)-2-pyrrolidinecarboxamide

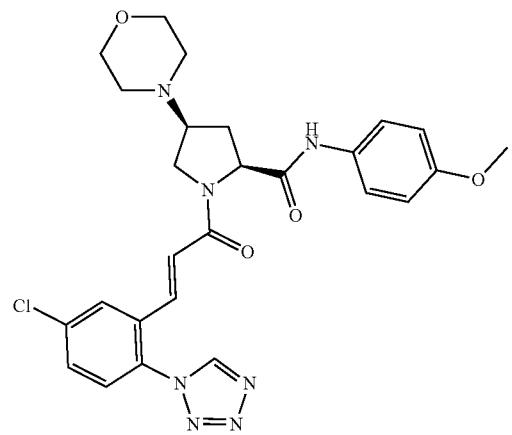 [SMILES: COc1ccc(NC(=O)[C@@H]2C[C@H](N3CCOCC3)CN2C(=O)/C=C/c2cc(Cl)ccc2-n2cnnn2)cc1]

The compound prepared in Example 2 was treated following the procedures described in Examples 3, 4, 5, 6 and 8 to give the title compound having the following physical properties. (Note: in the step corresponding to Example 3, morpholine was used in place of 1-(methylsulfonyl)piperazine. In the step corresponding to Example 5, 4-methoxyaniline was used in place of tert-butyl 4-aminobenzoate. In the step corresponding to Example 8, (2E)-3-[5-chloro-2-(1H-tetrazol-1-yl)phenyl]acrylic acid was used in place of 1-(N,N'-bis{[(2-methyl-2-propanyl)oxy]carbonyl}carbamimidoyl)-4-piperidinecarboxylic acid).

$^1$H NMR (500 MHz, DMSO-$d_6$, rotamers present) δ 9.87 (s, 1H), 9.86 (s, 1H), 8.36 (d, 1H), 7.76 (dd, 1H), 7.71 (d, 1H), 7.47 (d, 2H), 7.28 (d, 1H), 6.86 (d, 2H), 6.85 (d, 1H), 4.38 (t, 1H), 4.27 (dd, 1H), 3.71 (s, 3H), 3.63-3.57 (m, 4H), 3.38 (obs. t, 1H), 2.88-2.79 (m, 1H), 2.53-2.39 (m, 5H), 1.68 (dd, 1H).

ESI MS m/z 538 (M+H)$^+$

Example 43

(2S,4S)—N-(1H-benzotriazol-6-yl)-1-{(2E)-3-[5-chloro-2-(1H-tetrazol-1-yl)phenyl]-2-propenoyl}-4-(4-morpholinyl)-2-pyrrolidinecarboxamide trifluoroacetate

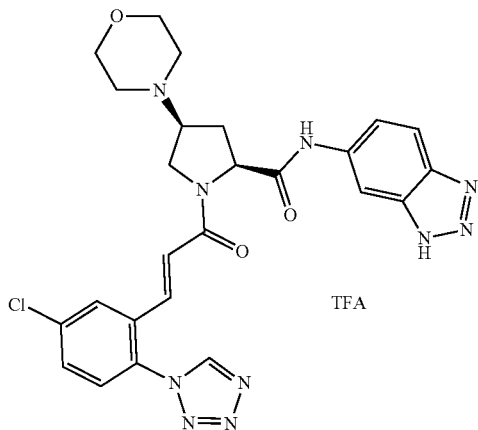 [SMILES: O=C(Nc1ccc2nn[nH]c2c1)[C@@H]1C[C@H](N2CCOCC2)CN1C(=O)/C=C/c1cc(Cl)ccc1-n1cnnn1]

The compound prepared in Example 2 was treated following the procedures described in Example 3, 4, 5, 6 and 8 to give the title compound having the following physical properties. (Note: in the step corresponding to Example 3, morpholine was used in place of 1-(methylsulfonyl)piperazine. In the step corresponding to Example 5, 5-aminobenzotriazole was used in place of tert-butyl 4-aminobenzoate. In the step corresponding to Example 8, (2E)-3-[5-chloro-2-(1H-tetrazol-1-yl)phenyl]acrylic acid was used in place of 1-(N,N'-bis{[(2-methyl-2-propanyl)oxy]carbonyl}carbamimidoyl)-4-piperidinecarboxylic acid).

$^1$H NMR (500 MHz, CD$_3$OD, rotamers present) δ 9.53 (s, 1H), 8.35 (d, 1H), 8.16 (d, 1H), 7.84 (d, 1H), 7.68 (dd, 1H), 7.59 (d, 1H), 7.46 (dd, 1H), 7.19 (d, 1H), 7.07 (d, 1H), 4.74 (t, 1H), 4.42 (dd, 1H), 4.12 (dd, 1H), 4.09-4.02 (m, 1H), 3.98 (br. s, 4H), 3.47 (br. s, 4H), 2.91-2.83 (m, 1H), 2.49-2.41 (m, 1H).

ESI MS m/z 549 (M+H)$^+$

Example 44

(2S,4S)—N-(3-chlorophenyl)-1-{(2E)-3-[5-chloro-2-(1H-tetrazol-1-yl)phenyl]-2-propenoyl}-4-(4-morpholinyl)-2-pyrrolidinecarboxamide

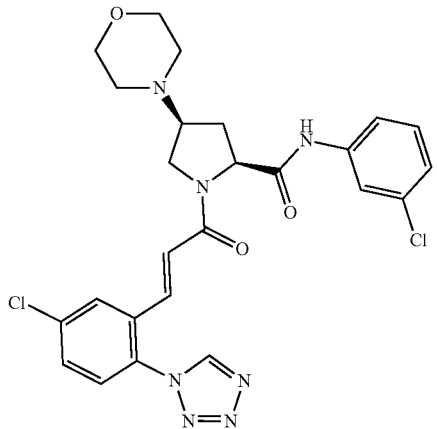 [SMILES: O=C(Nc1cccc(Cl)c1)[C@@H]1C[C@H](N2CCOCC2)CN1C(=O)/C=C/c1cc(Cl)ccc1-n1cnnn1]

The compound prepared in Example 2 was treated following the procedures described in Examples 3, 4, 5, 6 and 8 to give the title compound having the following physical properties. (Note: in the step corresponding to Example 3, morpholine was used in place of 1-(methylsulfonyl)piperazine. In the step corresponding to Example 5, 3-chloroaniline was used in place of tert-butyl 4-aminobenzoate. In the step corresponding to Example 8, (2E)-3-[5-chloro-2-(1H-tetrazol-1-yl)phenyl]acrylic acid was used in place of 1-(N,N'-bis{[(2-methyl-2-propanyl)oxy]carbonyl}carbamimidoyl)-4-piperidinecarboxylic acid).

$^1$H NMR (500 MHz, DMSO-d$_6$, rotamers present) δ 10.21 (s, 1H), 9.86 (s, 1H), 8.35 (d, 1H), 7.78 (app. s, 1H), 7.75 (dd, 1H), 7.71 (d, 1H), 7.41 (d, 1H), 7.33 (t, 1H), 7.28 (d, 1H), 7.10 (d, 1H), 6.86 (d, 1H), 4.39 (t, 1H), 4.27 (dd, 1H), 3.58 (br. s, 4H), 3.39 (t, 1H), 2.94-2.82 (m, 1H), 2.51-2.38 (m, 5H), 1.68 (dd, 1H).

ESI MS m/z 542/544 (M+H)$^+$

Example 45

(2S,4S)—N-(3-chloro-4-fluorophenyl)-1-{(2E)-3-[5-chloro-2-(1H-tetrazol-1-yl)phenyl]-2-propenoyl}-4-(4-morpholinyl)-2-pyrrolidinecarboxamide

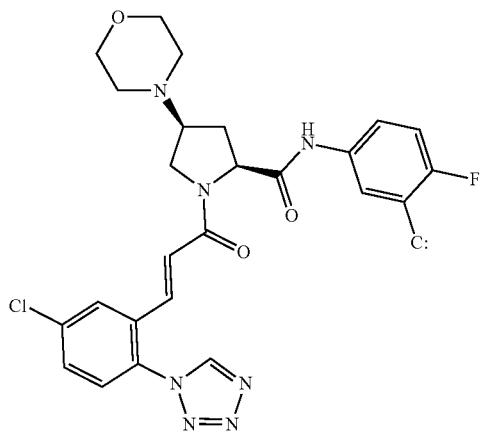

The compound prepared in Example 2 was treated following the procedures described in Examples 3, 4, 5, 6 and 8 to give the title compound having the following physical properties. (Note: in the step corresponding to Example 3, morpholine was used in place of 1-(methylsulfonyl)piperazine. In the step corresponding to Example 5, 3-chloro-4-fluoroaniline was used in place of tert-butyl 4-aminobenzoate. In the step corresponding to Example 8, (2E)-3-[5-chloro-2-(1H-tetrazol-1-yl)phenyl]acrylic acid was used in place of 1-(N,N'-bis{[(2-methyl-2-propanyl)oxy]carbonyl}carbamimidoyl)-4-piperidinecarboxylic acid).

$^1$H NMR (500 MHz, DMSO-d$_6$, rotamers present) δ 10.27 (s, 1H), 9.86 (s, 1H), 8.32 (d, 1H), 7.90 (dd, 1H), 7.75 (dd, 1H), 7.71 (d, 1H), 7.48-7.40 (m, 1H), 7.36 (t, 1H), 7.27 (d, 1H), 6.85 (d, 1H), 4.38 (t, 1H), 4.27 (dd, 1H), 3.58 (br. s, 4H), 3.41 (t, 1H), 2.93-2.79 (m, 1H), 2.52-2.39 (m, 5H), 1.68 (dd, 1H).

ESI MS (ES$^+$) m/z 560/562 (M+H)$^+$

Example 46

(2S,4S)-1-{(2E)-3-[5-chloro-2-(1H-tetrazol-1-yl)phenyl]-2-propenoyl}-4-(4-morpholinyl)-N-(2-oxo-2,3-dihydro-1H-benzimidazol-5-yl)-2-pyrrolidinecarboxamide trifluoroacetate

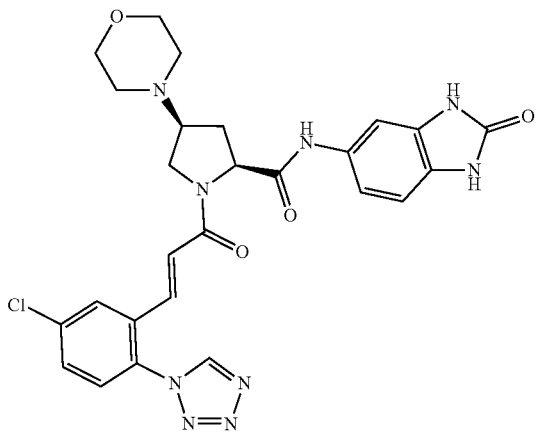 [SMILES: O=C(Nc1ccc2[nH]c(=O)[nH]c2c1)[C@@H]1C[C@H](N2CCOCC2)CN1C(=O)/C=C/c1cc(Cl)ccc1-n1cnnn1]

The compound prepared in Example 2 was treated following the procedures described in Examples 3, 4, 5, 6 and 8 to give the title compound having the following physical properties. (Note: in the step corresponding to Example 3, morpholine was used in place of 1-(methylsulfonyl)piperazine. In the step corresponding to Example 5, 5-aminobenzimidazolone was used in place of tert-butyl 4-aminobenzoate. In the step corresponding to Example 8, (2E)-3-[5-chloro-2-(1H-tetrazol-1-yl)phenyl]acrylic acid was used in place of 1-(N,N'-bis{[(2-methyl-2-propanyl)oxy]carbonyl}carbamimidoyl)-4-piperidinecarboxylic acid).

$^1$H NMR (500 MHz, DMSO-d$_6$, rotamers present) δ 10.68 (s, 1H), 10.52 (s, 1H), 10.37-9.93 (br. s, 1H), 9.87 (s, 1H), 8.29 (app. br. s, 1H), 7.78 (dd, 1H), 7.75 (d, 1H), 7.39 (s, 1H), 7.26 (d, 1H), 6.99 (d, 1H), 6.94-6.73 (m, 2H), 4.48 (app. br. s, 1H), 4.32-3.48 (m, 7H), 3.26-2.15 (m, 5H), 2.18-1.94 (m, 1H).

ESI MS m/z 564 (M+H)$^+$

Example 47

(2S,4S)-1-[(3-chloro-1H-indol-5-yl)carbonyl]-4-[4-(cyclopropylsulfonyl)-1-piperazinyl]-N-phenyl-2-pyrrolidinecarboxamide

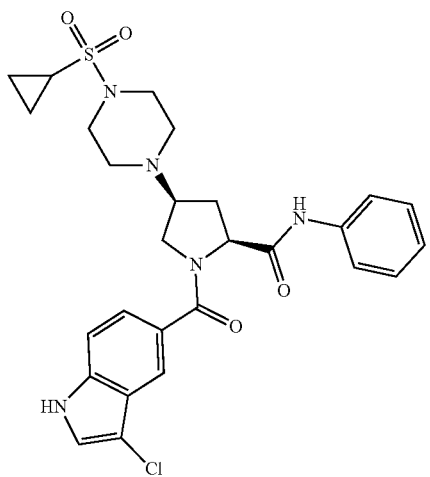 [SMILES: O=C(Nc1ccccc1)[C@@H]1C[C@H](N2CCN(S(=O)(=O)C3CC3)CC2)CN1C(=O)c1ccc2[nH]cc(Cl)c2c1]

The compound prepared in Example 2 was treated following the procedures described in Examples 3, 4, 5, 6 and 8 to give the title compound having the following physical properties. (Note: in the step corresponding to Example 3, 1-(cyclopropanesulfonyl)piperazine was used in place of 1-(methylsulfonyl)piperazine. In the step corresponding to Example 5, aniline was used in place of tert-butyl 4-aminobenzoate. In the step corresponding to Example 8, 3-chloroindole-5-carboxylic acid was used in place of 1-(N,N'-bis{[(2-methyl-2-propanyl)oxy]carbonyl}carbamimidoyl)-4-piperidinecarboxylic acid).

$^1$H NMR (500 MHz, CDCl$_3$, rotamers present) δ 9.43 (s, 1H), 8.53 (s, 1H), 7.86 (s, 1H), 7.57 (d, 2H), 7.43 (d, 1H), 7.40 (d, 1H), 7.32-7.25 (m, 3H), 7.08 (t, 1H), 5.105.00 (m, 1H), 3.93-3.84 (m, 1H), 3.59-3.50 (m, 1H), 3.31 (br. s, 4H), 2.88-2.78 (m, 1H), 2.73-2.57 (m, 3H), 2.53-2.44 (m, 2H), 2.43-2.35 (m, 1H), 2.28-2.20 (m, 1H), 1.19-1.13 (m, 2H), 1.02-0.95 (m, 2H).

ESI MS m/z 556 (M+H)$^+$

Example 48 methyl 4-({[(2S,4S)-4-amino-1-({trans-4-[({[(2-methyl-2-propanyl)oxy]carbonyl}amino)methyl]cyclohexyl}carbonyl)-2-pyrrolidinyl]carbonyl}amino)benzoate Methyl-4-[(2S,4S)-1-{[4-({[(tert-butoxy)carbonyl]amino}methyl)cyclohexyl]carbonyl}-4-{[(9H-fluoren-9-ylmethoxy)carbonyl]amino}pyrrolidine-2-amido]benzoate was synthesized by following the procedures described in Examples 5, 9 and 8 starting from (2S,4S)-1-tert-butoxycarbonyl-4-(9-fluorenylmethoxycarbonyl)amino-pyrrolidine-2-carboxylic acid. (Note: in the step corresponding to Example 5, methyl 4-aminobenzoate was used in place of tert-butyl 4-aminobenzoate. In the step corresponding to Example 8, trans-4-(tert-butoxycarbonylamino)cyclohexanecarboxylic acid was used in place of the compound prepared in Example 7) The crude material (11.61 g) was suspended in anhydrous tetrahydrofuran (120 mL) and piperidine (6.6 mL) added dropwise. The reaction was stirred for 2 hours then further piperidine (6.6 mL) was added and the reaction stirred overnight. The solvent was removed in vacuo and the residue purified by column chromatography (silica gel, 25-100% ethyl acetate/heptanes, 5-10% methanol/ethyl acetate then 0-20% methanol/dichloromethane) to give the title compound (3.04 g) as pale yellow foam.

ESI MS m/z 503 (M+H)$^+$

Example 49 methyl 4-({[(2S,4S)-4-(4-benzyl-1-piperazinyl)-1-({cis-4-[({[(2-methyl-2-propanyl)oxy]carbonyl}amino)methyl]cyclohexyl}carbonyl)-2-pyrrolidinyl]carbonyl}amino)benzoate To a solution of the compound prepared in Example 48 (1.05 g) in 2-propanol (56 mL) was added N-benzyl-N,N-bis(2-chloroethyl)amine hydrochloride (0.59 g) and sodium bicarbonate (3.6 g) and the reaction refluxed for 16 h. The reaction was reduced in vacuo, the residue diluted with water and extracted with ethyl acetate. The combined ethyl acetate fractions were washed with brine, dried and concentrated. The residue was purified by column chromatography (silica gel, 0-20% methanol/dichloromethane) to give the title compound (0.90 g) as a colourless solid.

ESI MS m/z 662 (M+H)$^+$

Example 50 methyl 4-({[(2S,4S)-1-({cis-4-[({[(2-methyl-2-propanyl)oxy]carbonyl}amino)methyl]cyclohexyl}carbonyl)-4-(1-piperazinyl)-2-pyrrolidinyl]carbonyl}amino)benzoate To a flask under nitrogen was added the compound prepared in Example 49 (0.90 g), ammonium formate (2.57 g) and palladium on carbon (1.61 g). Methanol was added (45 mL) under nitrogen and the reaction heated at reflux for 2.5 h. The reaction mixture was cooled and filtered through Celite®, washing the filter cake with methanol. The solvent was removed in vacuo, diluted with water and extracted with ethyl acetate. The combined ethyl acetate fractions were washed with brine, dried and concentrated to give the title compound (0.57 g) as a colourless solid.

ESI MS m/z 572 (M+H)+

Example 51 methyl 4-[(3S,5S)-5-{[4-(methoxycarbonyl)phenyl]carbamoyl}-1-({cis-4-[({[(2-methyl-2-propanyl)oxy]carbonyl}amino)methyl]cyclohexyl}carbonyl)-3-pyrrolidinyl]-1-piperazinecarboxylate To a stirred solution of the compound prepared in Example 50 (150 mg) in dichloromethane (3 mL) was added triethylamine (0.3 mL) and methyl chloroformate (22 μL). The mixture was stirred at room temperature overnight. Further methyl chloroformate (11 μL) was added and the reaction stirred at room temperature for an additional 4 days. The reaction mixture was partitioned between dichloromethane (20 mL) and brine (20 mL), the organic layer separated, dried and concentrated. The residue was purified by column chromatography (silica gel, ethyl acetate) to give the title compound (119 mg) as a white solid.

ESI MS m/z 630 (M+H)+

Example 52

4-[({(2S,4S)-1-{[trans-4-(aminomethyl)cyclohexyl]carbonyl}-4-[4-(methoxycarbonyl)-1-piperazinyl]-2-pyrrolidinyl}carbonyl)amino]benzoic acid bis(trifluoroacetate)

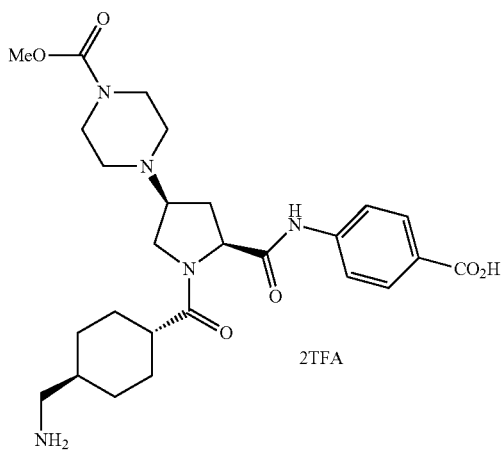 [SMILES: COC(=O)N1CCN([C@H]2C[C@@H](C(=O)Nc3ccc(C(=O)O)cc3)N(C(=O)[C@H]3CC[C@H](CN)CC3)C2)CC1]

To a solution of the compound prepared in Example 51 (119 mg) in methanol (1 mL) and THF (1 mL) was added 1 N sodium hydroxide (2 mL) and the mixture stirred at room temperature for 2 h. The organic solvents were removed in vacuo, the residual aqueous phase neutralised by addition of 1 N hydrochloric acid (2 mL) and extracted into dichloromethane (3×10 mL). The combined organic phases were washed with brine, dried and concentrated. The residue (99 mg) was redissolved in dichloromethane (5 mL) and treated with trifluoroacetic acid (2 mL). The reaction mixture was stirred at room temperature for 1 hour then concentrated. Purification by high performance liquid chromatography ([5 to 100% mobile phase B (0.1% trifluoroacetic acid in acetonitrile) in mobile phase A (0.1% trifluoroacetic acid in water] gave the title compound (90 mg, 64%) as a white solid.

$^1$H NMR (500 MHz, CD$_3$OD, rotamers present) δ 7.98 (d, 2H), 7.71 (d, 2H), 4.59 (t, 1H), 4.34 (dd, 1H), 4.04-3.96 (m, 1H), 3.93 (dd, 1H), 3.78 (br. s, 4H), 3.75 (s, 3H), 3.48-3.33 (m, 4H), 2.89-2.81 (m, 1H), 2.80 (d, 2H), 2.60 (tt, 1H), 2.32 (dt, 1H), 2.03-1.95 (m, 1H), 1.95-1.83 (m, 3H), 1.69-1.55 (m, 1H), 1.55-1.41 (m, 2H), 1.23-1.09 (m, 2H).

ESI MS m/z 516 (M+H)+

Example 53

4-({[(2S,4S)-4-(4-acetyl-1-piperazinyl)-1-{[trans-4-(aminomethyl)cyclohexyl]carbonyl}-2-pyrrolidinyl]carbonyl}amino)benzoic acid bis(trifluoroacetate)

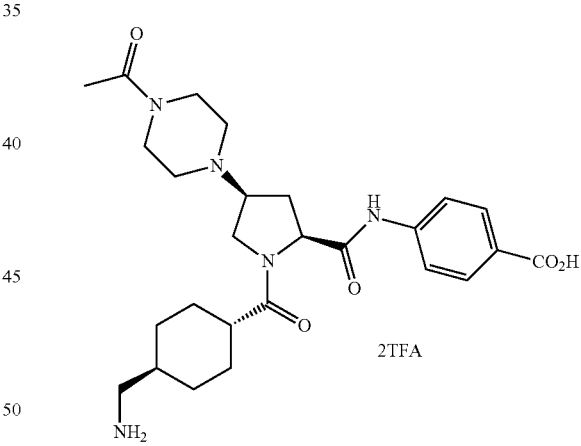

The compound prepared in Example 50 was treated following the procedures described in Example 51 and 52 to give the title compound having the following physical properties. (Note: in the step corresponding to Example 51, acetic anhydride was used in place of methyl chloroformate.)

$^1$H NMR (500 MHz, CD$_3$OD, rotamers present) δ 7.98 (d, 2H), 7.71 (d, 2H), 4.59 (t, 1H), 4.35-4.28 (m, 1H), 3.95-3.76 (m, 6H), 3.39 (br. s, 2H), 3.35 (br. s, 2H), 2.88-2.77 (m, 3H), 2.60 (tt, 1H), 2.34-2.25 (m, 1H), 2.16 (s, 3H), 2.03-1.96 (m, 1H), 1.96-1.84 (m, 3H), 1.70-1.58 (m, 1H), 1.53-1.42 (m, 2H), 1.21-1.09 (m, 2H).

ESI MS m/z 500 (M+H)+

Example 54

4-({[(2S,4S)-1-{[trans-4-(aminomethyl)cyclohexyl]carbonyl}-4-(4-carbamoyl-1-piperazinyl)-2-pyrrolidinyl]carbonyl}amino)benzoic acid bis(trifluoroacetate)

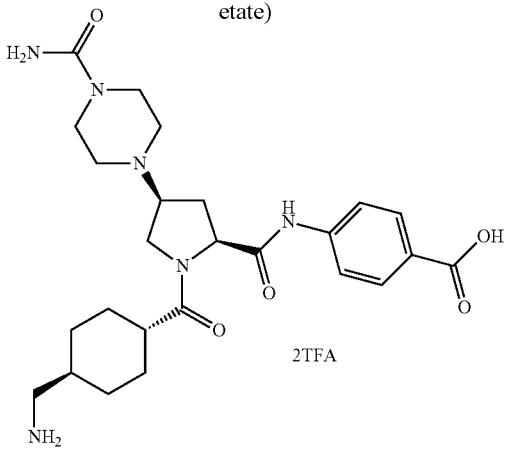

To a solution of the compound prepared in Example 50 (150 mg) in acetic acid (2 mL) and water (2 mL) was added potassium isocyanate (105 mg) and the mixture stirred at room temperature for 4 days. The reaction mixture was then treated with saturated aqueous sodium bicarbonate (10 mL) and extracted into dichloromethane (3×10 mL). The combined organic phases were washed with brine, dried and concentrated. Purification by flash chromatography (silica gel, 5-10% methanol/dichloromethane) gave methyl 4-[(2S,4S)-1-{[4-({[(tert-butoxy)carbonyl]amino}methyl)cyclohexyl]carbonyl}-4-(4-carbamoylpiperazin-1-yl)pyrrolidine-2-amido]benzoate (54 mg) as a colourless oil.

The compound thus obtained was treated following the procedure described in Example 52 to give the title compound (51 mg, 29%) as a white solid.

$^1$H NMR (500 MHz, CD$_3$OD, rotamers present) δ 7.98 (d, 2H), 7.71 (d, 2H), 4.60 (t, 1H), 4.36 (dd, 1H), 4.08-3.99 (m, 1H), 3.95 (dd, 1H), 3.74 (br. s, 4H), 3.43 (br. s, 4H), 2.91-2.83 (m, 1H), 2.80 (d, 2H), 2.60 (tt, 1H), 2.34 (dt, 1H), 2.03-1.95 (m, 1H), 1.95-1.83 (m, 3H), 1.69-1.56 (m, 1H), 1.55-1.41 (m, 2H), 1.22-1.10 (m, 2H).

ESI MS m/z 501 (M+H)$^+$

Example 55

4-[({(2S,4S)-1-{[trans-4-(aminomethyl)cyclohexyl]carbonyl}-4-[4-(cyclopropylsulfonyl)-1-piperazinyl]-2-pyrrolidinyl}carbonyl)amino]benzoic acid bis(trifluoroacetate)

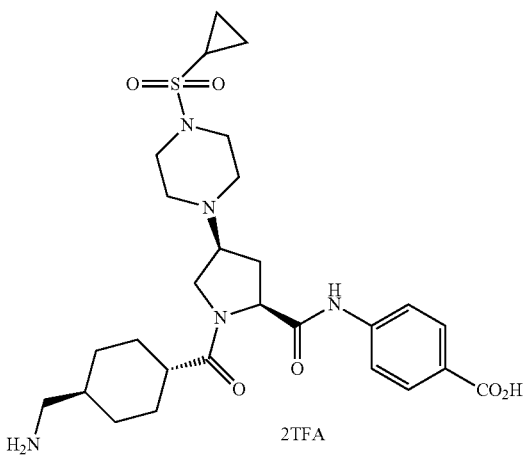 [SMILES: NC[C@H]1CC[C@H](C(=O)N2C[C@@H](N3CCN(S(=O)(=O)C4CC4)CC3)C[C@H]2C(=O)Nc2ccc(C(=O)O)cc2)CC1]

The compound prepared in Example 50 was treated following the procedures described in Example 51 and 52 to give the title compound having the following physical properties. (Note: in the step corresponding to Example 51, cyclopropanesulfonyl chloride was used in place of methyl chloroformate.)

$^1$H NMR (300 MHz, CD$_3$OD, rotamers present) δ 8.03-7.91 (m, 2H), 7.77-7.63 (m, 2H), 4.55 (t, 1H), 4.26 (t, 1H), 3.96-3.60 (m, 2H), 3.60-3.40 (m, 4H), 3.40-3.09 (m, 4H), 2.88-2.45 (m, 5H), 2.43-2.08 (m, 1H), 2.06-1.35 (m, 7H), 1.27-0.96 (m, 6H).

FAB MS m/z 562 (M+H)$^+$

Example 55-2

4-[({(2S,4S)-1-{[trans-4-(aminomethyl)cyclohexyl]carbonyl}-4-[4-(ethylsulfonyl)-1-piperazinyl]-2-pyrrolidinyl}carbonyl)amino]benzoic acid bis(trifluoroacetate)

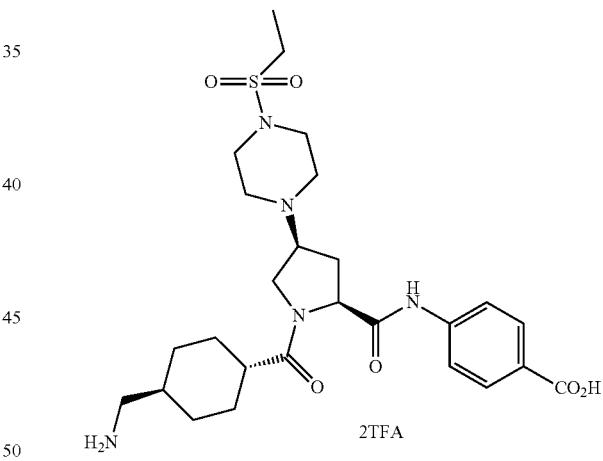

The compound prepared in Example 50 was treated following the procedures described in Example 51 and 52 to give the title compound having the following physical properties. (Note: in the step corresponding to Example 51, ethanesulfonyl chloride was used in place of methyl chloroformate.)

$^1$H NMR (300 MHz, CD$_3$OD, rotamers present) δ 8.06-7.91 (m, 2H), 7.88-7.62 (m, 2H), 4.55 (t, 1H), 4.35-4.17 (m, 1H), 3.88-3.61 (m, 2H), 3.61-3.41 (m, 4H), 3.41-3.03 (m, 6H), 2.89-2.49 (m, 3H), 2.44-2.08 (m, 1H), 2.06-1.25 (m, 11H), 1.25-0.98 (m, 2H).

FAB MS m/z 550 (M+H)$^+$

Example 56

(2S,4S)-1-{(2E)-3-[5-chloro-2-(1H-tetrazol-1-yl)phenyl]-2-propenoyl}-N-phenyl-4-(4-sulfamoyl-1-piperazinyl)-2-pyrrolidinecarboxamide trifluoroacetate

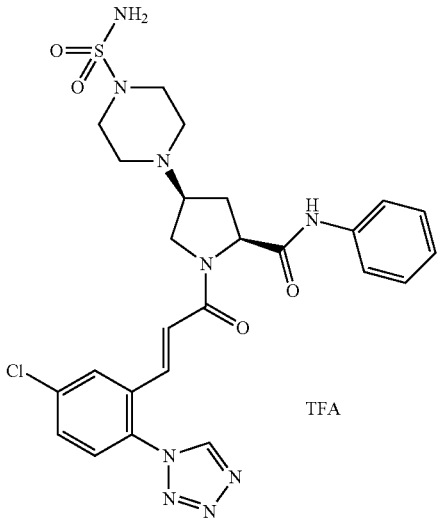 [SMILES: NS(=O)(=O)N1CCN([C@H]2C[C@@H](C(=O)Nc3ccccc3)N(C(=O)/C=C/c3cc(Cl)ccc3-n3cnnn3)C2)CC1]

The compound prepared in Example 2 was treated following the procedures described in Example 3, 4, 5, 9, 51, 6, 8 and 9 to give the title compound having the following physical properties. (Note: in the steps corresponding to Examples 3, 5, 8 and 51, 1-(tert-butoxycarbonyl)piperazine, aniline, (2E)-3-[5-chloro-2-(1H-tetrazol-1-yl)phenyl]acrylic acid and sulfamide in 1,4-dioxane were used respectively)

$^1$H NMR (500 MHz, DMSO-$d_6$, rotamers present) δ 10.06 (br. s, 1H), 9.86 (s, 1H), 8.37 (d, 1H), 7.76 (dd, 1H), 7.72 (d, 1H), 7.56 (d, 2H), 7.34-7.25 (m, 3H), 7.03 (t, 1H), 6.85 (d, 1H), 6.75 (br. s, 2H), 4.43 (t, 1H), 4.32 (dd, 1H), 3.43-3.34 (obs. m, 1H), 2.98 (br. s, 4H), 2.94-2.85 (m, 1H), 2.58 (br. s, 4H), 2.50-2.40 (obs. m, 1H), 1.68 (dd, 1H).

ESI MS m/z 586 (M+H)$^+$, 557 [(M-N$_2$)]

Example 57

(2S,4S)-1-{(2E)-3-[5-chloro-2-(1H-tetrazol-1-yl)phenyl]-2-propenoyl}-4-[(3S)-3-methyl-4-sulfamoyl-1-piperazinyl]-N-phenyl-2-pyrrolidinecarboxamide trifluoroacetate

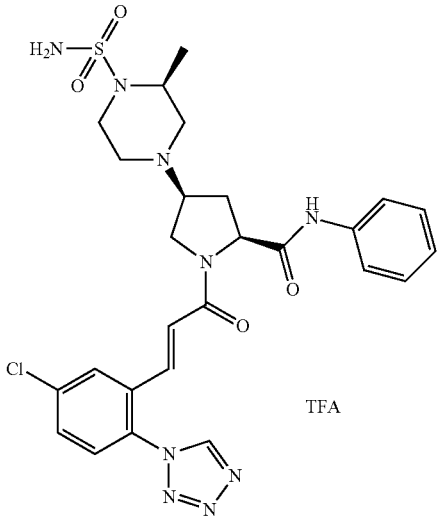 [SMILES: C[C@H]1CN([C@H]2C[C@@H](C(=O)Nc3ccccc3)N(C(=O)/C=C/c3cc(Cl)ccc3-n3cnnn3)C2)CCN1S(N)(=O)=O]

The compound prepared in Example 2 was treated following the procedures described in Example 3, 4, 5, 9, 51, 6, 8 and 9 to give the title compound having the following physical properties. (Note: in the step corresponding to the Example 3, 5, 8 and 51, 1-(tert-butoxycarbonyl)-2(S)-methylpiperazine, aniline, (2E)-3-[5-chloro-2-(1H-tetrazol-1-yl)phenyl]acrylic acid and sulfamide in 1,4-dioxane were used respectively)

$^1$H NMR (500 MHz, DMSO-$d_6$, rotamers present) δ 9.65 (s, 1H), 8.23-8.00 (m, 1H), 7.74-7.60 (m, 2H), 7.56 (d, 2H), 7.27 (t, 2H), 7.13-6.90 (m, 3H), 4.73-4.42 (m, 1H), 4.21-4.04 (m, 1H), 3.96-3.46 (m, 4H), 3.44-3.32 (m, 1H), 3.31-2.97 (m, 3H), 2.97-2.80 (m, 1H), 2.80-2.65 (m, 1H), 1.99-1.72 (m, 1H), 1.32-1.18 (m, 3H).

ESI MS m/z 600 (M+H)$^+$

Example 58

(3R,3'S,5'S)-1'-{(2E)-3-[5-chloro-2-(1H-tetrazol-1-yl)phenyl]-2-propenoyl}-N-phenyl-3-(sulfamoylamino)-1,3'-bipyrrolidine-5'-carboxamide

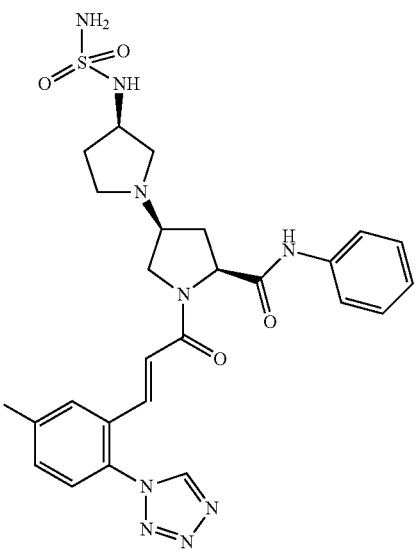

The compound prepared in Example 2 was treated following the procedures described in Examples 3, 4, 5, 9, 51, 6, 8 and 9 to give the title compound having the following physical properties. (Note: in the step corresponding to the Example 3, 5, 8 and 51, (3R)-3-(tert-butoxycarbonylamino)pyrrolidine, aniline, (2E)-3-[5-chloro-2-(1H-tetrazol-1-yl)phenyl]acrylic acid and sulfamide in 1,4-dioxane were used respectively)

$^1$H NMR (500 MHz, DMSO-$d_6$, rotamers present) δ 10.01 (s, 1H), 9.85 (s, 1H), 8.38 (d, 1H), 7.75 (dd, 1H), 7.71 (d, 1H), 7.55 (d, 2H), 7.31-7.25 (m, 3H), 7.03 (t, 1H), 6.85 (d, 1H), 6.72 (d, 1H), 6.53 (br. s, 2H), 4.42 (t, 1H), 4.20 (dd, 1H), 3.82-3.71 (m, 1H), 3.48-3.39 (obs. m, 1H), 2.99-2.89 (m, 1H), 2.88-2.77 (m, 1H), 2.64-2.51 (obs. m, 3H), 2.48-2.36 (m, 2H), 2.14-2.00 (m, 1H), 1.74-1.62 (m, 1H).

ESI MS (ES$^+$) m/z 608 (M+Na)$^+$, 586 (M+H)$^+$

Example 59

2-methyl-2-propanyl 4-[({(2S,4S)-1-({4-[({[(2-methyl-2-propanyl)oxy]carbonyl}amino)methyl]-1-piperidinyl}carbonyl)-4-[4-(methylsulfonyl)-1-piperazinyl]-2-pyrrolidinyl}carbonyl)amino]benzoate To a solution of the compound prepared in Example 6 (0.050 g, 0.11 mmol) in THF (10 mL) were added triphosgene (0.099 g, 0.33 mmol), (boc-4-aminomethyl)-piperidine (0.060 g, 0.28 mmol) and N,N-diisopropylethylamine (0.146 mL, 0.84 mmol) and the reaction stirred at 0° C. for 2 h. The reaction was quenched by adding ice cold water and the resulting precipitate was collected by filtration, dried and the crude product purified by flash chromatography to afford the title compound (0.052 g, 33%) as a white solid.

$^1$H NMR (400 MHz, CDCl$_3$, rotamers present) δ 9.12 (s, 1H), 7.93 (d, 2H), 7.55 (d, 2H), 4.80 (dd, 1H), 4.62-4.57 (m, 1H), 3.83-3.65 (m, 2H), 3.57-3.48 (m, 1H), 3.32 (t, 1H), 3.26-3.24 (m, 4H), 3.04-2.97 (m, 3H), 2.89-2.81 (m, 2H), 2.78 (s, 3H), 2.71-2.66 (m, 3H), 2.58-2.53 (m, 2H), 2.41-2.46 (m, 2H), 1.76-1.62 (m, 4H), 1.58 (s, 9H), 1.43 (s, 9H).

Example 60

4-[({(2S,4S)-1-{[4-(aminomethyl)-1-piperidinyl]carbonyl}-4-[4-(methylsulfonyl)-1-piperazinyl]-2-pyrrolidinyl}carbonyl)amino]benzoic acid bis(trifluoroacetate)

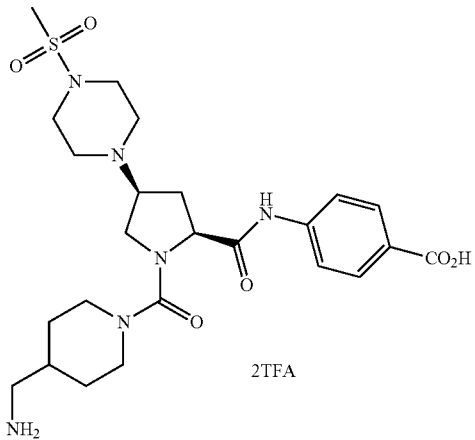 [SMILES: CS(=O)(=O)N1CCN([C@H]2C[C@@H](C(=O)Nc3ccc(C(=O)O)cc3)N(C(=O)N3CCC(CN)CC3)C2)CC1]

The compound prepared in Example 59 was treated following the procedure described in Example 9 to give the title compound as an off-white solid.

$^1$H NMR (400 MHz, CD$_3$OD, rotamers present) δ 7.98 (d, 2H), 7.71 (d, 2H), 4.68 (dd, 1H), 3.94-3.81 (m, 1H), 3.74-3.69 (m, 1H), 3.59-3.39 (m, 4H), 3.23-3.08 (m, 4H), 3.03-2.94 (m, 1H), 2.91 (s, 3H), 2.85-2.70 (m, 4H), 2.09 (q, 1H), 1.89-1.71 (m, 3H), 1.42-1.14 (m, 5H).

ESI MS m/z 537 (M+H)$^+$

Example 61

2-methyl 1-(2-methyl-2-propanyl)(2S)-4-(4-pyridinyl)-2,5-dihydro-1H-pyrrole-1,2-dicarboxylate A solution of 2-methyl 1-(2-methyl-2-propanyl) (2S)-4-(trifluoromethylsulfonyloxy)-1H-pyrrole-1,2(2H,5H)-dicarboxylate (11.3 g, 30.1 mmol) and 4-pyridineboronic acid (4.44 g, 36.1 mmol) in 1,4-dioxane (120 mL) was purged with argon gas, followed by the addition of tetrakis(triphenylphosphine)palladium (1.04 g, 0.9 mmol) and sodium carbonate (2 M in water, 38 mL, 76 mmol). The reaction was heated at 105° C. and stirred under argon atmosphere for 1 h whereupon the reaction was cooled to room temperature and concentrated to a volume of 50 mL. The solution was diluted with ethyl acetate (200 mL) and filtered through diatomaceous earth with a layer of sodium sulfate on the top. The filtrate was concentrated and purified by flash chromatography (silica gel, 400 g, 20-70% ethyl acetate/hexanes) to afford the title compound (6.4 g, 70%) as a pale yellow solid.

$^1$H NMR (500 MHz, CDCl$_3$, rotamers present) δ 8.63-8.61 (m, 2H), 7.25-7.23 (m, 2H), 6.33 (d, 0.4H), 6.28 (d, 0.6H), 5.23 (dt, 0.4H), 5.16 (dt, 0.6H), 4.65-4.55 (m, 2H), 3.78 (s, 1.2H), 3.77 (s, 1.8H), 1.53 (s, 3.6H), 1.46 (s, 5.4H).

Example 62 methyl(2S,4R)-1-{[(2-methyl-2-propanyl)oxy]carbonyl}-4-[1-(methylsulfonyl)-4-piperidinyl]-2-pyrrolidinecarboxylate A solution of the compound prepared in Example 61 (4.31 g, 14.1 mmol) and acetic acid (0.8 mL) in ethanol (80 mL) was purged with hydrogen. Platinum oxide (0.86 g, 20 wt %) was added and the mixture heated at 50° C. and stirred overnight under an atmosphere of hydrogen. The reaction mixture was then cooled to room temperature and filtered through diatomaceous earth with methanol. The filtrate was concentrated and the residue partitioned between dichloromethane (100 mL) and water (50 mL). The aqueous layer was adjusted to pH 10 by addition of 2 M sodium hydroxide and extracted with dichloromethane (4×50 mL). The combined organic extracts were concentrated and azeotroped with toluene to give the crude product as an off-white foam. The crude material was dissolved in dichloromethane (100 mL) and cooled to 0° C. Triethylamine (3.93 mL, 28.2 mmol) was added, followed by methylsulfonyl chloride (1.64 mL, 21.1 mmol). The reaction was stirred under nitrogen at 0° C. for 1 h then at room temperature overnight whereupon the mixture was diluted with ethyl acetate (300 mL) and washed with 1 M hydrochloric acid (50 mL), aqueous sodium bicarbonate (50 mL) and brine (50 mL). The organic layer was then dried and concentrated. Purification by flash chromatography (silica gel, 120 g, 0-8% methanol/dichloromethane) afforded the title compound (2.6 g, 47% for two steps) as a pale yellow foam.

$^1$H NMR (500 MHz, CDCl$_3$, rotamers present) δ 4.26 (dd, 0.3H), 4.20 (dd, 0.7H), 3.86-3.78 (m, 2.1H), 3.74 (s, 0.9H), 3.72 (s, 2.1H), 3.72-3.69 (m, 0.9H), 3.06 (t, 1H), 2.76 (s, 3H), 2.63-2.59 (m, 2H), 2.45-2.42 (m, 1H), 1.98-1.91 (m, 1H), 1.79-1.73 (m, 2H), 1.60-1.52 (m, 1H), 1.46 (s, 2.7H), 1.40 (s, 6.3H), 1.46-1.25 (m, 3H).

Example 63

(2S,4R)-1-{[(2-methyl-2-propanyl)oxy]carbonyl}-4-[1-(methylsulfonyl)-4-piperidinyl]-2-pyrrolidinecarboxylic acid To a solution of the compound prepared in Example 62 (2.87 g, 7.36 mmol) in tetrahydrofuran (20 mL) and water (20 mL) at 0° C. was added lithium hydroxide (0.35 g, 14.7 mmol). The reaction was warmed to room temperature and stirred overnight whereupon it was partitioned between methyl tert-butyl ether and water. The aqueous layer was separated and carefully acidified to pH 1 with 6 N hydrochloric acid. The aqueous solution was extracted with ethyl acetate (2×300 mL) and the combined organic extracts concentrated to give the title compound (2.35 g, 85%) as a white solid.

$^1$H NMR (500 MHz, CDCl$_3$, rotamers present) δ 4.35 (t, 0.7H), 4.27-4.23 (m, 0.3H), 3.83-3.73 (m, 3H), 3.10-2.97 (m, 1H), 2.77 (s, 3H), 2.62 (td, 2H), 2.54-2.47 (m, 0.3H), 2.36-2.32 (m, 0.7H), 2.13-2.06 (m, 0.7H), 1.96-1.89 (m, 1.3H), 1.77-1.73 (m, 1H), 1.50 (s, 6.3H), 1.42 (s, 2.7H), 1.45-1.32 (m, 4H).

Example 64

2-methyl-2-propanyl(2S,4R)-2-(5-{4-[(methoxycarbonyl)amino]phenyl}-1H-imidazol-2-yl)-4-[1-(methylsulfonyl)-4-piperidinyl]-1-pyrrolidinecarboxylate To a solution of the compound prepared in Example 62 (2.35 g, 6.2 mmol) in N,N-dimethylformamide (50 mL) at 0° C. was added methyl 4-(2-bromoacetyl)phenylcarbamate (2.04 g, 7.49 mmol) followed by cesium carbonate (4.47 g, 13.7 mmol). The reaction was warmed to room temperature and stirred for 1.5 h whereupon the mixture was filtered through diatomaceous earth and the filter cake washed with dichloromethane. The filtrate was concentrated to afford crude product as a yellow solid. To a suspension of crude material in xylene (45 mL) in a glass pressure bottle was added ammonium acetate (2.88 g, 37.4 mmol). The reaction vessel was filled with nitrogen, sealed and heated at 140° C. for 1 h whereupon the mixture was cooled to room temperature, concentrated and partitioned between ethyl acetate (200 mL) and water (50 mL). The organic layer was washed with aqueous sodium bicarbonate solution and brine, dried and concentrated. Purification by flash chromatography (silica gel, 120 g, 40-60% ethyl acetate/dichloromethane then 3-5% methanol/dichloromethane) afforded the title compound (2.42 g, 71% for two steps) as a pale yellow solid.

$^1$H NMR (500 MHz, CDCl$_3$, rotamers present) δ 11.06 (s, 0.4H), 10.66 (s, 0.6H), 7.70-7.67 (m, 2H), 7.40-7.36 (m, 2H), 7.19 (s, 0.6H), 7.13 (s, 0.4H), 6.71 (s, 0.4H), 6.66 (s, 0.6H), 4.97-4.91 (m, 1H), 3.83-3.77 (m, 3H), 3.77 (s, 3H), 2.96-2.94 (m, 1H), 2.76 (s, 3H), 2.62-2.59 (m, 2H), 2.56-2.50 (m, 1H), 2.14-2.11 (m, 0.6H), 2.00-1.92 (m, 1.4H), 1.78-1.75 (m, 1H), 1.48 (s, 9H), 1.45-1.38 (m, 4H).

ESI MS m/z 548 (M+H)$^+$

Example 65

2-methyl-2-propanyl(2S,4R)-2-(4-chloro-5-{4-[(methoxycarbonyl)amino]phenyl}-1H-imidazol-2-yl)-4-[1-(methylsulfonyl)-4-piperidinyl]-1-pyrrolidinecarboxylate To a solution of the compound prepared in Example 64 (2.41 g, 4.4 mmol) in acetonitrile (50 mL) and N,N-dimethylformamide (20 mL) at 0° C. was added N-chlorosuccinimide (0.62 g, 4.6 mmol). The reaction was warmed to room temperature, stirred under nitrogen overnight then heated between 50-70° C. for 2 h. The reaction was cooled to room temperature, concentrated under reduced pressure and the residue washed with aqueous sodium bicarbonate solution (1×50 mL). The solid residue was suspended in a mixture of ethyl acetate (100 mL) and dichloromethane (100 mL) and sonicated. The solids were collected by filtration to give the title compound (1.39 g) as an off-white solid.

$^1$H NMR (500 MHz, DMSO-d$_6$, rotamers present) δ 12.28 (s, 1H), 9.76 (s, 1H), 7.60 (d, 2H), 7.53 (d, 2H), 4.67-4.59 (m, 1H), 3.72-3.64 (m, 1H), 3.68 (s, 3H), 3.55-3.53 (m, 2H), 3.11 (t, 1H), 2.84 (s, 3H), 2.68-2.64 (m, 2H), 2.41-2.38 (m, 1H), 2.02-1.93 (m, 1H), 1.79-1.66 (m, 3H), 1.37 (s, 2.5H), 1.37-1.12 (m, 3H), 1.11 (s, 6.5H).

ESI MS m/z 582 (M+H)$^+$

Example 66 methyl [4-(2-{(2S,4R)-4-[1-(methylsulfonyl)-4-piperidinyl]-2-pyrrolidinyl}-1H-imidazol-5-yl)phenyl]carbamate hydrochloride To a solution of the compound prepared in Example 64 (0.447 g, 0.811 mmol) in 1,4-dioxane was added 4 M HCl in 1,4-dioxane (5.0 mL) and the reaction mixture stirred at room temperature for 1 h. The mixture was concentrated and the residue was purified by trituration with 1:1 dichloromethane/hexanes to afford the title compound (0.46 g, 99%) as a light brown solid.

$^1$H NMR (400 MHz, DMSO-d$_6$) δ 10.20 (br. s, 1H), 9.81 (br. s, 1H), 7.89 (br. s, 1H), 7.81 (d, 2H), 7.56 (d, 2H), 4.93-4.89 (m, 1H), 3.68 (s, 3H), 3.65-3.52 (m, 2H), 3.50-3.46 (m, 3H), 3.27-3.24 (m, 1H), 2.86 (s, 3H), 2.72-2.69 (m, 2H), 2.68-2.65 (m, 1H), 2.22-2.19 (m, 2H), 1.81-1.79 (m, 2H), 1.29-1.27 (m, 2H).

Example 67 methyl [4-(4-chloro-2-{(2S,4R)-4-[1-(methylsulfonyl)-4-piperidinyl]-2-pyrrolidinyl}-1H-imidazol-5-yl)phenyl]carbamate hydrochloride The compound prepared in Example 65 was treated following the procedure described in Example 66 to give the title compound as a light yellow solid.

$^1$H NMR (400 MHz, DMSO-d$_6$) δ 13.50 (br. s, 1H), 9.95 (br. s, 1H), 9.82 (s, 1H), 9.28 (br. s, 1H), 7.68 (d, 2H), 7.58 (d, 2H), 4.73-4.69 (m, 1H), 3.68 (s, 3H), 3.59-3.55 (m, 3H), 3.56-3.44 (m, 2H), 3.06-3.01 (m, 1H), 2.85 (s, 3H), 2.67 (t, 1H), 2.20-2.18 (m, 1H), 1.96-1.90 (m, 1H), 1.78-1.76 (m, 2H), 1.46-1.43 (m, 1H), 1.39-1.32 (m, 2H).

Example 68 bis(2-methyl-2-propanyl){[4-({(2S,4R)-2-(5-{4-[(methoxycarbonyl)amino]phenyl}-1H-imidazol-2-yl)-4-[1-(methylsulfonyl)-4-piperidinyl]-1-pyrrolidinyl}carbonyl)-1-piperidinyl]methylylidene}biscarbamate To a solution of the compound prepared in Example 66 (0.11 g, 0.25 mmol) in dichloromethane (5.0 mL) and N,N-dimethylformamide (2.0 mL) was added 1-hydroxy-7-azabenzotriazole (0.034 g, 0.25 mmol), followed by N-methyl morpholine (0.075 g, 0.74 mmol), 1-ethyl-3-(3-dimethylaminopropyl)carbodiimide hydrochloride (0.095 g, 0.50 mmol) and the compound prepared in Example 7 (0.10 g, 0.27 mmol). The reaction was stirred at room temperature under nitrogen overnight whereupon it was concentrated under reduced pressure. The resultant residue was diluted with dichloromethane (20 mL), washed with brine (10 mL), dried and concentrated. Purification by flash chromatography (silica gel, 12 g, 0-5% methanol/dichloromethane) and trituration from methanol and methyl tert-butyl ether afforded the title compound (0.067 g, 38%) as a yellow solid.

$^1$H NMR (300 MHz, CDCl$_3$, rotamers present) δ 10.84 (s, 0.3H), 10.54 (s, 0.7H), 10.16 (s, 1H), 7.72-7.65 (d, 1.4H), 7.46-7.31 (m, 2.6H), 7.20-7.08 (m, 1H), 6.65-6.50 (m, 1H), 5.30-5.16 (t, 1H), 4.28-4.10 (m, 2H), 3.93-3.81 (m, 3H), 3.78 (s, 3H), 3.35-3.15 (m, 1H), 3.10-2.98 (m, 2H), 2.92-2.87 (m, 0.7H), 2.85-2.77 (m, 0.3H), 2.78 (s, 3H), 2.71-2.57 (m, 3H), 2.51-2.45 (m, 1H), 2.18-2.10 (m, 0.6H), 2.08-1.90 (m, 2.4H), 1.81-1.65 (m, 4H), 1.49 (s, 18H), 1.50-1.32 (m, 3H).

ESI MS m/z 801 (M+H)$^+$

Example 69 methyl [4-(2-{(2S,4R)-1-[(1-carbamimidoyl-4-piperidinyl)carbonyl]-4-[1-(methylsulfonyl)-4-piperidinyl]-2-pyrrolidinyl}-1H-imidazol-5-yl)phenyl]carbamate dihydrochloride

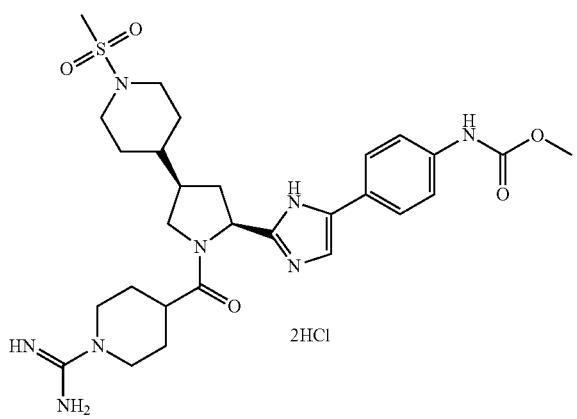 [SMILES: COC(=O)Nc1ccc(-c2cnc([C@@H]3C[C@H](C4CCN(S(C)(=O)=O)CC4)CN3C(=O)C3CCN(C(=N)N)CC3)[nH]2)cc1]

To a solution of the compound prepared in Example 68 (0.067 g, 0.084 mmol) in dichloromethane (2 mL) at 0° C. was added trifluoroacetic acid (0.09 mL, 1.2 mmol). The reaction was warmed to room temperature and stirred for 4 h whereupon the solvent and excess trifluoroacetic acid was removed in vacuo. The resulting residue was dissolved in methanol (5 mL) and 6 M hydrochloric acid (0.70 mL) was added. The mixture was concentrated to dryness and the process repeated twice. The residue was triturated with methanol and methyl tert-butyl ether, the resulting solids dissolved in water and lyophilized to afford the title compound (0.050 g, 96%) as a yellow solid.

$^1$H NMR (500 MHz, DMSO-d$_6$, rotamers present) δ 15.04 (s, 1H), 14.66 (s, 1H), 9.88 (s, 1H), 7.88 (s, 1H), 7.84-7.79 (d, 2H), 7.60-7.54 (d, 2H), 7.33 (app. s, 3H), 5.06-4.99 (m, 1H), 4.05-3.90 (m, 1H), 3.88-3.75 (m, 3H), 3.68 (s, 3H), 3.63-3.40 (m, 3H), 3.15-3.00 (m, 2H), 2.85 (s, 3H), 2.78-2.60 (m, 2H), 2.25-2.10 (m, 1H), 2.05-1.92 (m, 1H), 1.91-1.65 (m, 4H), 1.52-1.39 (m, 2H), 1.39-1.10 (m, 3H).

ESI MS m/z 601 (M+H)$^+$

Example 70 bis(2-methyl-2-propanyl) {[4-({(2S,4R)-2-(4-chloro-5-{4-[(methoxycarbonyl)amino]phenyl}-1H-imidazol-2-yl)-4-[1-(methylsulfonyl)-4-piperidinyl]-1-pyrrolidinyl}carbonyl)-1-piperidinyl]methylylidene}biscarbamate The compound prepared in Example 67 was treated with the compound prepared in Example 7 following the procedure described in Example 68 to give the title compound as a white solid.

$^1$H NMR (500 MHz, CDCl$_3$, rotamers present) δ 10.91 (s, 1H), 10.16 (s, 1H), 7.56 (d, 2H), 7.45 (d, 2H), 6.64 (s, 1H), 5.15 (t, 1H), 4.25-4.11 (m, 2H), 3.88-3.85 (m, 3H), 3.79 (s, 3H), 3.16 (t, 1H), 3.08-2.99 (m, 2H), 2.77 (s, 3H), 2.70-2.60 (m, 4H), 2.51-2.44 (m, 1H), 2.04-1.92 (m, 3H), 1.81-1.70 (m, 4H), 1.49 (s, 9H), 1.47 (s, 9H), 1.59-1.40 (m, 3H).

ESI MS m/z 835 (M+H)$^+$

Example 71 methyl [4-(2-{(2S,4R)-1-[(1-carbamimidoyl-4-piperidinyl)carbonyl]-4-[1-(methylsulfonyl)-4-piperidinyl]-2-pyrrolidinyl}-4-chloro-1H-imidazol-5-yl)phenyl]carbamate dihydrochloride

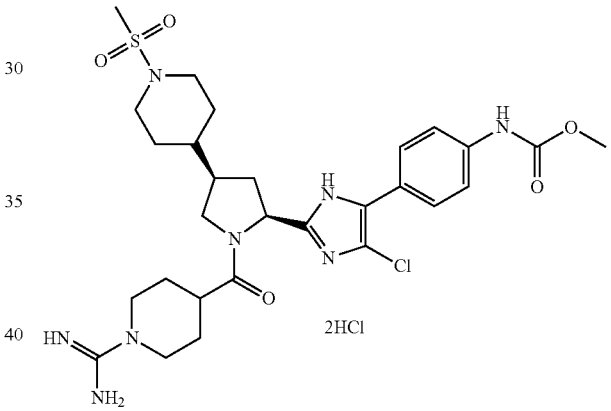

The compound prepared in Example 70 was treated following the procedure described in Example 69 to give the title compound as a white solid.

$^1$H NMR (500 MHz, DMSO-d$_6$, rotamers present) δ 13.05 (s, 0.4H), 12.68 (s, 0.6H), 9.80 (s, 0.4H), 9.79 (s, 0.6H), 7.65 (d, 0.8H), 7.60 (d, 1.2H), 7.56-7.53 (m, 2H), 7.31 (app. s, 2.4H), 7.26 (app. s, 1.6H), 5.12-5.10 (m, 0.4H), 4.84-4.80 (m, 0.6H), 3.99-3.95 (m, 1H), 3.84-3.79 (m, 1H), 3.68 (s, 3H), 3.58-3.53 (m, 2.4H), 3.40 (t, 0.6H), 3.09-3.07 (m, 2H), 2.84 (s, 3H), 2.72-2.64 (m, 3H), 2.49-2.43 (m, 2H), 2.10-1.97 (m, 0.6H), 1.87-1.65 (m, 5.4H), 1.52-1.19 (m, 5H).

ESI MS m/z 635 (M+H)$^+$

Example 72

2-methyl-2-propanyl {imino[4-({(2S,4R)-2-(5-{4-[(methoxycarbonyl)amino]phenyl}-1H-imidazol-2-yl)-4-[1-(methylsulfonyl)-4-piperidinyl]-1-pyrrolidinyl}carbonyl)phenyl]methyl}carbamate The compound prepared in Example 66 was treated with the compound prepared in Example 18 following the procedure described in Example 8 to give the title compound as a white solid.

¹H NMR (500 MHz, CDCl₃, rotamers present) δ 7.90 (d, 2H), 7.71 (s, 1H), 7.65-7.52 (d, 2H), 7.44-7.35 (d, 2H), 7.22-7.15 (m, 3H), 6.57 (s, 1H), 5.42-5.32 (t, 1H), 3.90-3.85 (m, 1H), 3.78 (s, 3H), 3.64-3.52 (m, 1H), 3.51-3.45 (d, 1H), 3.38-3.22 (t, 1H), 2.77 (s, 3H), 2.69-2.54 (m, 2H), 2.10-1.88 (m, 2H), 1.53 (s, 9H), 1.43-1.38 (m, 1H), 1.35-1.20 (m, 4H), 0.85-0.90 (m, 1H).

ESI MS m/z 694 (M+H)⁺

Example 73 methyl [4-(2-{(2S,4R)-1-(4-carbamimidoylbenzoyl)-4-[1-(methylsulfonyl)-4-piperidinyl]-2-pyrrolidinyl}-1H-imidazol-5-yl)phenyl]carbamate dihydrochloride

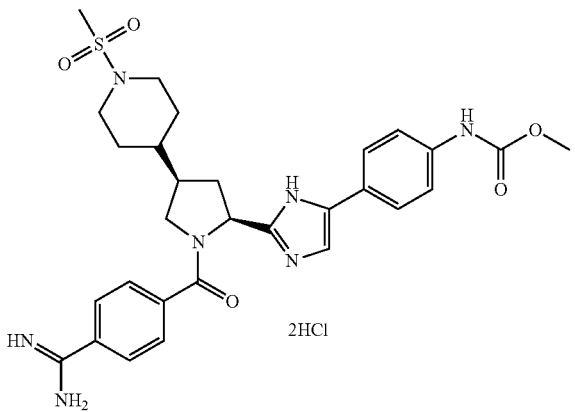 [SMILES: COC(=O)Nc1ccc(-c2cnc([C@@H]3C[C@H](C4CCN(S(C)(=O)=O)CC4)CN3C(=O)c3ccc(C(=N)N)cc3)[nH]2)cc1]

The compound prepared in Example 72 was treated following the procedure described in Example 69 to give the title compound as an off-white solid.

¹H NMR (500 MHz, DMSO-d₆, rotamers present) δ 15.25 (s, 1H), 14.87 (s, 1H), 9.88 (s, 1H), 9.46-9.38 (m, 2H), 9.15-9.05 (m, 2H), 8.05-7.75 (m, 6H), 7.65-7.50 (d, 2H), 5.35-5.22 (m, 1H), 4.10-3.89 (m, 1H), 3.68 (s, 3H), 2.83 (s, 3H), 2.70-2.55 (m, 3H), 2.40-2.34 (m, 1H), 2.25-2.15 (m, 1H), 2.09-1.90 (m, 2H), 1.85-1.75 (m, 1H), 1.60-1.50 (m, 1H), 1.50-1.35 (m, 2H), 1.34-1.15 (m, 1H), 0.85-0.90 (m, 1H).

ESI MS m/z 594 (M+H)⁺

Example 74

2-methyl-2-propanyl {[4-({(2S,4R)-2-(4-chloro-5-{4-[(methoxycarbonyl)amino]phenyl}-1H-imidazol-2-yl)-4-[1-(methylsulfonyl)-4-piperidinyl]-1-pyrrolidinyl}carbonyl)phenyl](imino)methyl}carbamate The compound prepared in Example 67 was treated with the compound prepared in Example 18 following the procedure described in Example 8 to give the title compound as a white solid.

¹H NMR (500 MHz, CDCl₃, rotamers present) δ 10.89-10.88 (m, 1H), 7.89 (d, 2H), 7.57-7.54 (m, 4H), 7.40 (d, 2H), 6.67 (s, 1H), 5.33 (t, 1H), 3.85-3.82 (m, 1H), 3.78 (s, 3H), 3.77-3.75 (m, 1H), 3.59 (dd, 1H), 3.29 (t, 1H), 2.77 (s, 3H), 2.76-2.56 (m, 4H), 1.95-1.94 (m, 2H), 1.59-1.53 (m, 1H), 1.55 (s, 9H), 1.42-1.25 (m, 3H).

ESI MS m/z 728 (M+H)⁺

Example 75 methyl [4-(2-{(2S,4R)-1-(4-carbamimidoylbenzoyl)-4-[1-(methylsulfonyl)-4-piperidinyl]-2-pyrrolidinyl}-4-chloro-1H-imidazol-5-yl)phenyl]carbamate dihydrochloride

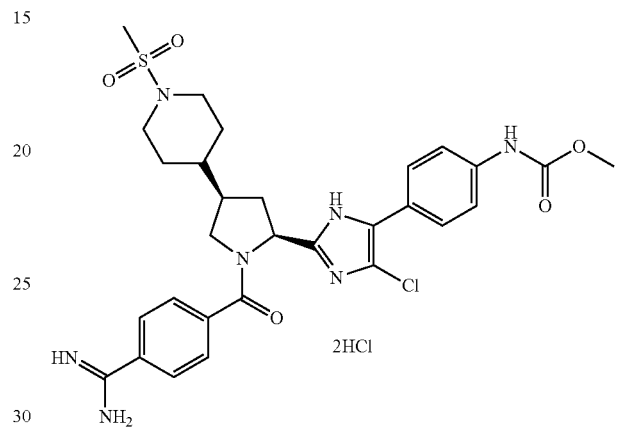

The compound prepared in Example 74 was treated following the procedure described in Example 69 to give the title compound as a white solid.

¹H NMR (500 MHz, DMSO-d₆, rotamers present) δ 12.80 (s, 0.8H), 12.25 (s, 0.2H), 9.78 (s, 1H), 9.41 (s, 1.6H), 9.25 (s, 0.4H), 9.09 (s, 1.6H), 8.96 (s, 0.4H), 7.88 (d, 1.6H), 7.83 (d, 1.6H), 7.76 (d, 0.4H), 7.63 (d, 1.6H), 7.54 (d, 1.6H), 7.49 (d, 0.4H), 7.39-7.34 (m, 0.8H), 5.08 (dd, 0.8H), 4.92 (t, 0.2H), 3.67 (s, 3H), 3.67-3.64 (m, 1H), 3.51-3.47 (m, 3H), 2.82 (s, 3H), 2.67-2.61 (m, 2H), 2.07-1.78 (m, 4H), 1.53-1.51 (m, 1H), 1.39-1.36 (m, 1H), 1.23-1.16 (m, 2H).

ESI MS m/z 628 (M+H)⁺

Example 76 methyl [4-(2-{(2R,4S)-1-[4-(N',N''-bis{[(2-methyl-2-propanyl)oxy]carbonyl}carbamimidamido)benzoyl]-4-[1-(methylsulfonyl)-4-piperidinyl]-2-pyrrolidinyl}-1H-imidazol-5-yl)phenyl]carbamate The compound prepared in Example 66 was treated with the compound prepared in Example 10 following the procedure described in Example 8 to give the title compound as a light brown solid.

¹H NMR (400 MHz, CDCl₃, rotamers present) δ 9.53 (s, 0.5H), 9.38 (s, 0.5H), 7.73 (d, 1H), 7.66 (d, 1H), 7.54 (d, 1H), 7.42-7.39 (m, 2H), 7.34-7.29 (m, 0.5H), 7.21-7.18 (m, 1.5H), 6.99-6.96 (m, 1H), 6.60-6.58 (m, 1H), 5.40-5.38 (m, 0.5H), 4.51-4.29 (m, 0.5H), 3.86-3.83 (m, 2H), 3.80 (s, 3H), 3.50-3.48 (m, 1H), 2.95-2.93 (m, 0.5H), 2.79-2.76 (m, 2.5H), 2.71-2.58 (m, 2H), 2.01-1.99 (m, 2H), 1.63-1.59 (m, 6H), 1.50-1.47 (m, 2H), 1.32-1.24 (m, 18H).

Example 77 methyl [4-(2-[(2S,4R)-1-(4-carbamimidamidoben-zoyl)-4-[1-(methylsulfonyl)-4-piperidinyl]-2-pyrro-lidinyl]-1H-imidazol-5-yl)phenyl]carbamate bis(trif-luoroacetate)

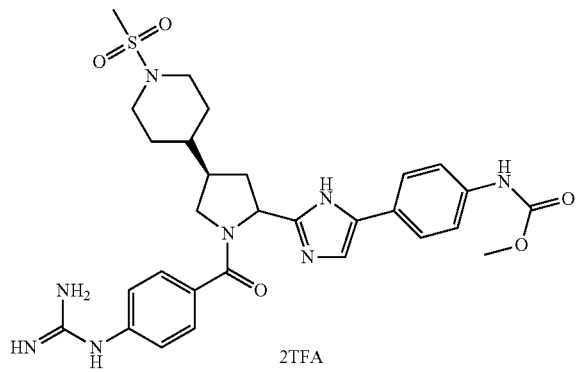 [SMILES: COC(=O)Nc1ccc(-c2cnc(C3C[C@H](C4CCN(S(C)(=O)=O)CC4)CN3C(=O)c3ccc(NC(=N)N)cc3)[nH]2)cc1]

The compound prepared in Example 76 was treated following the procedure described in Example 9 to give the title compound as an off-white solid.

¹H NMR (400 MHz, CD₃OD, rotamers present) δ 7.88 (d, 2H), 7.73 (s, 1H), 7.66 (d, 2H), 7.60 (d, 2H), 7.40 (d, 2H), 5.40 (q, 1H), 3.86-3.35 (m, 8H), 2.80 (s, 3H), 2.72-2.69 (m, 3H), 2.21-2.14 (m, 1H), 2.00-1.97 (m, 2H), 1.71-1.68 (m, 1H), 1.67-1.32 (m, 3H).

APCI MS m/z 609 (M+H)⁺

Example 78 methyl [4-(2-[(2R,4S)-1-[4-(N',N''-bis{[(2-methyl-2-propanyl)oxy]carbonyl}carbamimidamido)benzoyl]-4-[1-(methylsulfonyl)-4-piperidinyl]-2-pyrrolidinyl]-4-chloro-1H-imidazol-5-yl)phenyl]carbamate The compound prepared in Example 67 was treated with the compound prepared in Example 10 following the procedure described in Example 8 to give the title compound as a light brown solid.

¹H NMR (300 MHz, CDCl₃, rotamers present) δ 10.90 (br. s, 1H), 7.59 (d, 2H), 7.52 (d, 2H), 7.42 (d, 2H), 7.19 (d, 2H), 6.73 (s, 1H), 5.41-5.30 (m, 1H), 3.91-3.79 (m, 4H), 3.78 (s, 3H), 3.36 (t, 1H), 3.21-3.06 (m, 1H), 2.77 (s, 3H), 2.76-2.51 (m, 4H), 2.02-1.83 (m, 2H), 1.81-1.78 (m, 2H), 1.41-1.27 (m, 18H).

Example 79 methyl [4-(2-{(2S,4R)-1-(4-carbamimidamidoben-zoyl)-4-[1-(methylsulfonyl)-4-piperidinyl]-2-pyrro-lidinyl}-4-chloro-1H-imidazol-5-yl)phenyl]carbam-ate bis(trifluoroacetate)

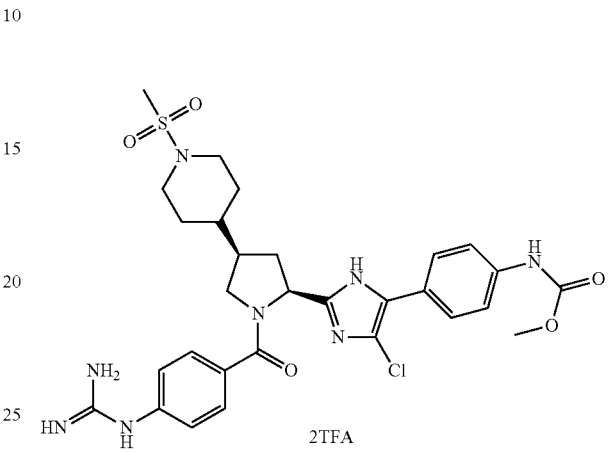

The compound prepared in Example 78 was treated following the procedure described in Example 9 to give the title compound as an off-white solid.

¹H NMR (400 MHz, CD₃OD, rotamers present) δ 7.74 (d, 2H), 7.64 (d, 2H), 7.54 (d, 2H), 7.37 (d, 2H), 5.19 (dd, 1H), 3.74 (s, 3H), 3.71-3.65 (m, 4H), 2.79 (s, 3H), 2.72-3.69 (m, 5H), 2.15-2.01 (m, 1H), 1.98-1.87 (m, 3H), 1.58-1.49 (m, 1H).

ESI MS m/z 643 (M+H)⁺

Example 80

2-methyl-2-propanyl {[cis-4-({(2S,4R)-2-(4-chloro-5-{4-[(methoxycarbonyl)amino]phenyl}-1H-imida-zol-2-yl)-4-[1-(methylsulfonyl)-4-piperidinyl]-1-pyrrolidinyl}carbonyl)cyclohexyl]methyl}carbamate Following the procedure described in Example 8, the compound prepared in Example 67 was treated with cis-4-[({[(2-methyl-2-propanyl)oxy]carbonyl}amino)methyl]cy-clohexanecarboxylic acid to give the title compound as a white solid.

¹H NMR (500 MHz, CDCl₃, rotamers present. One exchangeable proton was not observed.) δ 11.12 (s, 1H), 7.65-7.35 (m, 4H), 6.80-6.64 (m, 1H), 5.80-5.06 (m, 1H), 4.64-4.52 (m, 1H), 3.88-3.81 (m, 3H), 3.79 (s, 3H), 3.09-2.97 (m, 2H), 2.78 (s, 3H), 2.67-2.56 (m, 3H), 2.56-2.44 (m, 2H), 2.05-1.92 (m, 2H), 1.86-1.61 (m, 5H), 1.60-1.49 (m, 6H), 1.43 (s, 9H), 1.32-1.23 (m, 2H).

ESI MS m/z 721 (M+H)⁺

Example 81 methyl [4-(2-{(2S,4R)-1-{[cis-4-(aminomethyl)cyclohexyl]carbonyl}-4-[1-(methylsulfonyl)-4-piperidinyl]-2-pyrrolidinyl}-4-chloro-1H-imidazol-5-yl)phenyl]carbamate dihydrochloride

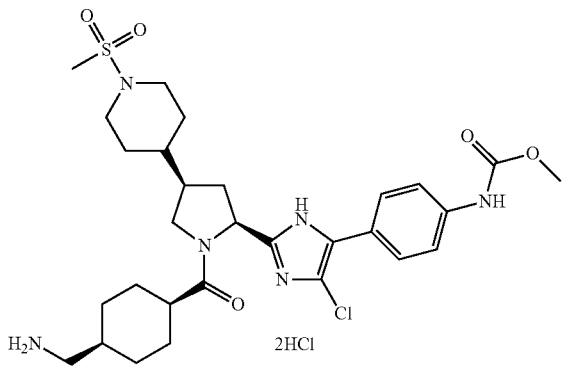 [SMILES: COC(=O)Nc1ccc(-c2[nH]c([C@@H]3C[C@H](C4CCN(S(C)(=O)=O)CC4)CN3C(=O)[C@H]3CC[C@@H](CN)CC3)nc2Cl)cc1]

The compound prepared in Example 80 was treated following the procedure described in Example 69 to give the title compound as a white solid.

$^1$H NMR (500 MHz, DMSO-d$_6$, rotamers present) δ 12.84 (s, 0.3H), 12.47 (s, 0.7H), 9.81-9.76 (m, 1H), 7.76-7.48 (m, 7H), 5.00 (t, 0.3H), 4.81 (t, 0.7H), 4.03-3.70 (m, 2H), 3.68 (s, 3H), 3.59-3.51 (m, 2H), 3.39-3.30 (m, 1H), 2.85 (s, 3H), 2.78-2.59 (m, 4H), 2.44-2.34 (m, 2H), 2.07-1.96 (m, 1H), 1.83-1.72 (m, 4H), 1.72-1.63 (m, 1H), 1.63-1.22 (m, 9H).

ESI MS m/z 621 (M+H)$^+$

Example 82

2-methyl-2-propanyl {(1S)-1-[trans-4-({(2S,4R)-2-(5-{4-[(methoxycarbonyl)amino]phenyl}-1H-imidazol-2-yl)-4-[1-(methylsulfonyl)-4-piperidinyl]-1-pyrrolidinyl}carbonyl)cyclohexyl]ethyl}carbamate Following the procedure described in Example 8, the compound prepared in Example 66 was treated with trans-4-[(1S)-1-({[(2-methyl-2-propanyl)oxy]carbonyl}amino)ethyl]cyclohexanecarboxylic acid to give the title compound as a light brown solid.

$^1$H NMR (400 MHz, CDCl$_3$, rotamers present) δ 7.52 (br s, 2H), 7.37 (d, 2H), 7.15 (s, 1H), 6.63 (br s, 1H), 5.20 (t, 1H), 4.44-4.41 (m, 1H), 3.92-3.80 (m, 3H), 3.78 (s, 3H), 3.60-3.49 (m, 1H), 3.22-3.10 (m, 1H), 2.79 (s, 3H), 2.71-2.59 (m, 2H), 2.55-2.48 (m, 1H), 2.41-2.29 (m, 1H), 2.12-2.09 (m, 1H), 2.08-1.98 (m, 1H), 1.91-1.70 (m, 6H), 1.65-1.49 (m, 4H), 1.44 (s, 9H), 1.38-1.32 (m, 2H), 1.09 (d, 3H), 1.04-1.03 (m, 1H).

Example 83 methyl [4-(2-{(2S,4R)-1-({trans-4-[(1S)-1-aminoethyl]cyclohexyl}carbonyl)-4-[1-(methylsulfonyl)-4-piperidinyl]-2-pyrrolidinyl}-1H-imidazol-5-yl)phenyl]carbamate bis(trifluoroacetate)

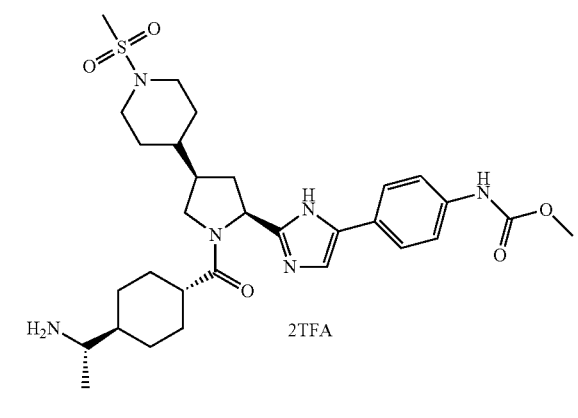 [SMILES: COC(=O)Nc1ccc(-c2cnc([C@@H]3C[C@H](C4CCN(S(C)(=O)=O)CC4)CN3C(=O)[C@H]3CC[C@H]([C@H](C)N)CC3)[nH]2)cc1]

The compound prepared in Example 82 was treated following the procedure described in Example 9 to give the title compound as a white solid.

$^1$H NMR (400 MHz, CD$_3$OD, rotamers present) δ 7.67 (s, 1H), 7.60-7.51 (m, 4H), 5.15-5.05 (m, 1H), 4.11-4.01 (m, 1H), 3.80-3.70 (m, 5H), 3.61-3.49 (m, 1H), 3.19-3.09 (m, 1H), 2.82 (s, 3H), 2.80-2.65 (m, 3H), 2.62-3.50 (m, 1H), 2.35-2.20 (m, 1H), 1.99-1.80 (m, 7H), 1.61-1.39 (m, 6H), 1.26 (d, 3H), 1.24-1.14 (m, 2H).

APCI MS m/z 601 (M+H)$^+$

Example 84 methyl [4-(4-chloro-2-{(2S,4R)-1-({4-[(methylamino)methyl]cyclohexyl}carbonyl)-4-[1-(methylsulfonyl)-4-piperidinyl]-2-pyrrolidinyl}-1H-imidazol-5-yl)phenyl]carbamate bis(trifluoroacetate)

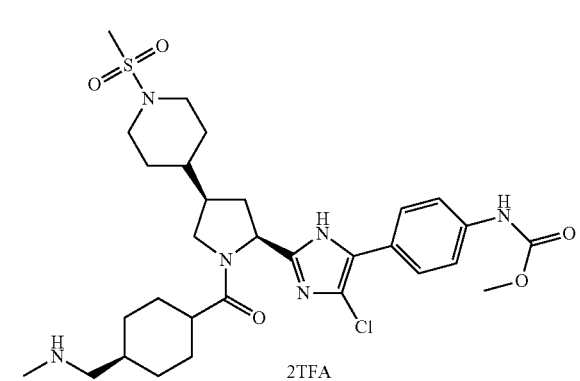

Following the procedure described in Example 8, the compound prepared in Example 67 was treated with trans-4-[(N-methyl-{[(2-methyl-2-propanyl)oxy]carbonyl}amino)methyl]cyclohexanecarboxilic acid to give the crude amide. After this, the crude amide was treated following the procedure described in Example 9 to give the title compound as an off-white solid.

¹H NMR (400 MHz, CD₃OD, rotamers present) δ 7.67-7.57 (m, 4H), 5.10 (dd, 1H), 4.06-4.00 (m, 1H), 3.75-3.68 (m, 5H), 3.60 (t, 1H), 2.87-2.81 (m, 6H), 2.74-2.66 (m, 8H), 2.29-2.26 (m, 2H), 2.23-1.67 (m, 5H), 1.49-1.28 (m, 4H), 1.17-0.60 (m, 3H).

ESI MS m/z 635 (M+H)⁺

Example 85

2-methyl-2-propanyl {(1S)-1-[trans-4-({(2S,4R)-2-(4-chloro-5-{4-[(methoxycarbonyl)amino]phenyl}-1H-imidazol-2-yl)-4-[1-(methylsulfonyl)-4-piperidinyl]-1-pyrrolidinyl}carbonyl)cyclohexyl]ethyl}carbamate Following the procedure described in Example 8, the compound prepared in Example 67 was treated with trans-4-[(1S)-1-({[(2-methyl-2-propanyl)oxy]carbonyl}amino)ethyl]cyclohexanecarboxylic acid to give the title compound as a light brown solid.

¹H NMR (300 MHz, CDCl₃, rotamers present) δ 11.0 (br. s, 1H), 7.57 (d, 2H), 7.45 (d, 2H), 6.68 (s, 1H), 5.17 (t, 1H), 4.34 (d, 1H), 3.87-3.83 (m, 3H), 3.79 (s, 3H), 3.52-3.49 (m, 1H), 3.16 (t, 1H), 2.88 (s, 3H), 2.68-2.59 (m, 3H), 2.50-2.47 (m, 1H), 2.30-2.28 (m, 1H), 2.00-1.87 (m, 3H), 1.85-1.73 (m, 5H), 1.48-1.46 (m, 1H), 1.45 (s, 9H), 1.25-1.23 (m, 4H), 1.09 (d, 3H), 1.06-1.03 (m, 1H).

Example 86 methyl [4-(2-{(2S,4R)-1-({trans-4-[(1S)-1-aminoethyl]cyclohexyl}carbonyl)-4-[1-(methylsulfonyl)-4-piperidinyl]-2-pyrrolidinyl}-4-chloro-1H-imidazol-5-yl)phenyl]carbamate bis(trifluoroacetate)

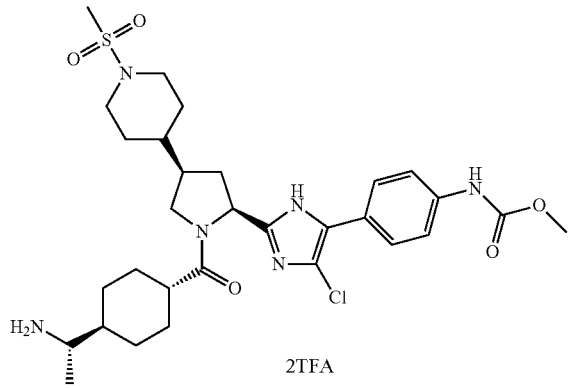 [SMILES: COC(=O)Nc1ccc(-c2[nH]c([C@@H]3C[C@H](C4CCN(S(C)(=O)=O)CC4)CN3C(=O)[C@H]3CC[C@H]([C@H](C)N)CC3)nc2Cl)cc1]

2TFA

The compound prepared in Example 85 was treated following the procedure described in Example 9 to give the title compound as an off-white solid.

¹H NMR (400 MHz, CD₃OD, rotamers present) δ 7.62 (d, 2H), 7.53 (d, 2H), 5.08-5.06 (m, 1H), 4.12-4.04 (m, 1H), 3.75 (app. s, 5H), 3.54-3.49 (m, 1H), 3.19-3.03 (m, 1H), 2.82 (s, 3H), 2.73-2.70 (m, 3H), 2.56-2.53 (m, 1H), 2.35-2.24 (m, 1H), 2.01-1.81 (m, 6H), 1.63-1.31 (m, 7H), 1.26 (d, 3H), 1.21-1.19 (m, 2H).

APCI MS m/z 635 (M+H)⁺

Example 87 bis(2-methyl-2-propanyl){[4-({(2S,4R)-2-(4-chloro-5-{4-[(methoxycarbonyl)amino]phenyl}-1H-imidazol-2-yl)-4-[1-(methylsulfonyl)-4-piperidinyl]-1-pyrrolidinyl}carbonyl)-1-piperazinyl]methylylidene}biscarbamate The compound prepared in Example 67 was treated with the compound prepared in Example 28 following the procedure described in Example 29 to give the title compound as a white solid.

¹H NMR (400 MHz, DMSO-d₆, rotamers present) δ 12.3 (s, 1H), 9.75 (s, 1H), 9.58 (s, 1H), 7.56 (d, 2H), 7.54 (d, 2H), 5.32-5.31 (m, 1H), 4.93 (t, 1H), 3.67 (s, 3H), 3.54-3.45 (m, 4H), 3.41-3.31 (m, 2H), 3.17-3.16 (m, 3H), 2.84 (s, 3H), 2.67-2.66 (m, 3H), 2.03-1.89 (m, 4H), 1.81-1.75 (m, 3H), 1.41 (s, 9H), 1.36 (s, 9H), 1.31-1.29 (m, 2H).

Example 88 methyl [4-(2-{(2S,4R)-1-[(4-carbamimidoyl-1-piperazinyl)carbonyl]-4-[1-(methylsulfonyl)-4-piperidinyl]-2-pyrrolidinyl}-4-chloro-1H-imidazol-5-yl)phenyl]carbamate bis(trifluoroacetate)

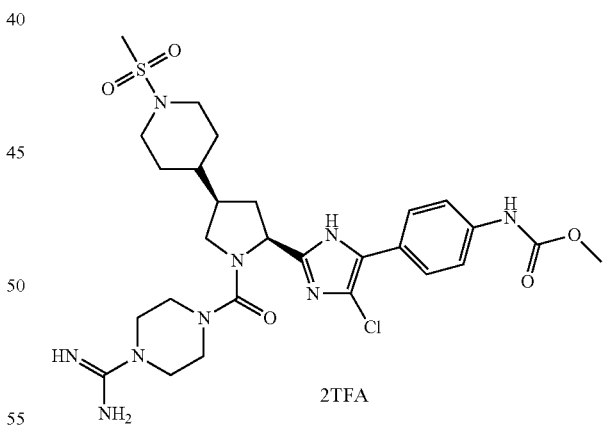

2TFA

The compound prepared in Example 87 was treated following the procedure described in Example 9 to give the title compound as an off-white solid.

¹H NMR (300 MHz, CD₃OD, rotamers present) δ 7.62 (d, 2H), 7.71 (d, 2H), 5.06-5.05 (m, 1H), 3.75 (s, 3H), 3.71-3.65 (m, 2H), 3.64-3.63 (m, 4H), 3.57-3.54 (m, 5H), 2.81 (s, 3H), 2.73 (t, 2H), 2.52-2.48 (m, 1H), 1.99-1.89 (m, 4H), 1.45-1.36 (m, 4H).

ESI MS, m/z 636 (M+H)⁺

Example 89

2-methyl-2-propanyl {[1-({(2S,4R)-2-(4-chloro-5-{4-[(methoxycarbonyl)amino]phenyl}-1H-imidazol-2-yl)-4-[1-(methylsulfonyl)-4-piperidinyl]-1-pyrrolidinyl}carbonyl)-4-piperidinyl]methyl}carbamate Following the procedure described in Example 29, the compound prepared in Example 67 was treated with 4-[({[(2-methyl-2-propanyl)oxy]carbonyl}amino)methyl]piperidine to give the title compound as a white solid.

$^1$H NMR (400 MHz, CDCl$_3$, rotamers present. One exchangeable proton was not observed.) δ 11.0 (s, 1H), 7.52-7.31 (m, 4H), 6.85 (s, 1H), 5.18-5.11 (m, 1H), 4.64-4.35 (m, 1H), 3.82-3.68 (m, 7H), 3.51-3.47 (m, 1H), 3.25 (t, 1H), 3.28-3.25 (m, 1H), 2.94-2.88 (m, 2H), 2.66 (s, 4H), 2.64-2.58 (m, 3H), 2.42-2.31 (m, 2H), 1.97-1.91 (m, 3H), 1.74-1.70 (m, 12H), 1.39-1.28 (m, 3H).

Example 90 methyl [4-(2-{(2S,4R)-1-{[4-(aminomethyl)-1-piperidinyl]carbonyl}-4-[1-(methylsulfonyl)-4-piperidinyl]-2-pyrrolidinyl}-4-chloro-1H-imidazol-5-yl)phenyl]carbamate bis(trifluoroacetate)

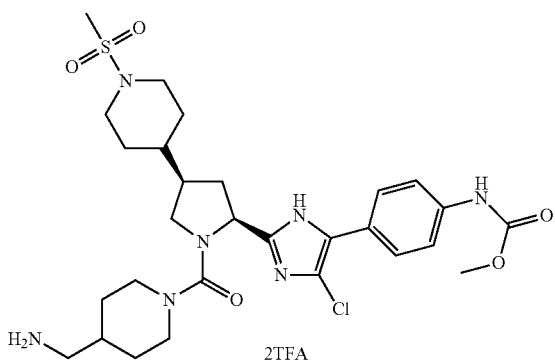 [SMILES: COC(=O)Nc1ccc(-c2[nH]c([C@@H]3C[C@H](C4CCN(S(C)(=O)=O)CC4)CN3C(=O)N3CCC(CN)CC3)nc2Cl)cc1]

The compound prepared in Example 89 was treated following the procedure described in Example 9 to give the title compound as an off-white solid.

$^1$H NMR (300 MHz, CD$_3$OD, rotamers present) δ 7.61 (d, 2H), 7.53 (d, 2H), 5.05 (dd, 1H), 3.95-3.90 (m, 1H), 3.88-3.81 (m, 1H), 3.76-3.68 (m, 4H), 3.57 (t, 1H), 3.50-3.48 (m, 1H), 2.92-2.89 (m, 1H), 2.85-2.73 (m, 6H), 2.70-2.48 (m, 3H), 2.47-2.45 (m, 1H), 2.03-2.09 (m, 1H), 1.88-1.70 (m, 4H), 1.46-1.14 (m, 7H).

ESI MS m/z 622 (M+H)$^+$

Example 91

4-[({(2S,4R)-1-{(2E)-3-[5-chloro-2-(1H-tetrazol-1-yl)phenyl]-2-propenoyl}-4-[1-(methylsulfonyl)-4-piperidinyl]-2-pyrrolidinyl}carbonyl)amino]benzoic acid

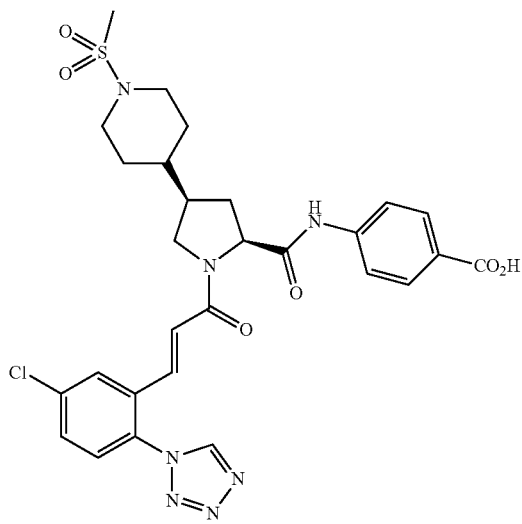 [SMILES: CS(=O)(=O)N1CCC([C@H]2C[C@@H](C(=O)Nc3ccc(C(=O)O)cc3)N(C(=O)/C=C/c3cc(Cl)ccc3-n3cnnn3)C2)CC1]

Allyl 4-[({(2S,4R)-1-{(2E)-3-[5-chloro-2-(1H-tetrazol-1-yl)phenyl]-2-propenoyl}-4-[1-(methylsulfonyl)-4-piperidinyl]-2-pyrrolidinyl}carbonyl)amino]benzoate was prepared by following the procedures described in Examples 5, 9 and 8 starting from the compound prepared in Example 63. (Note: in the step corresponding to Example 5, allyl 4-aminobenzoate was used in place of tert-butyl 4-aminobenzoate. In the step corresponding to Example 8, (2E)-3-[5-chloro-2-(1H-tetrazol-1-yl)phenyl]acrylic acid was used in place of 1-(N,N'-bis(tert-butoxycarbonyl)carbamimidoyl)piperidine-4-carboxylic acid). After that, to a solution of the crude allyl ester (48 mg) in N,N-dimethylformamide (1 mL) was added tetrakis(triphenylphosphine)palladium(0) (2 mg) and 1,3-dimethylbarbituric acid (4 mg) and the reaction stirred overnight at room temperature. Further tetrakis(triphenylphosphine)palladium(0) (3 mg) was added at this juncture and stirring continued at room temperature for 7 h. The reaction mixture was left to stand overnight, diluted with a 1:1 mixture of diisopropylether and dichloromethane (1 mL) and the resulting precipitate collected by filtration. The yellow powder obtained was washed with dichoromethane and dried to give the title compound having the following physical properties (25 mg).

$^1$H NMR (500 MHz, DMSO-d$_6$, rotamers present) δ 12.69 (br. s, 1H), 10.38 (s, 1H), 9.87 (s, 1H), 8.38 (d, 1H), 7.88 (d, 2H), 7.77 (dd, 1H), 7.72 (d, 1H), 7.68 (d, 2H), 7.30 (d, 1H), 6.85 (d, 1H), 4.42 (t, 1H), 4.21 (dd, 1H), 3.62-3.50 (m, 2H), 3.37-3.25 (obs. m, 1H), 2.86 (s, 3H), 2.75-2.62 (m, 2H), 2.45-2.37 (m, 1H), 2.14-2.01 (m, 1H), 1.88-1.77 (m, 2H), 1.53 (dd, 1H), 1.43-1.20 (m, 3H).

ESI MS m/z 628 (M+H)$^+$

Example 92

3-chloro-4-fluoro-1-methyl-1H-indole-5-carboxylic acid

To a solution of 4-fluoro-1-[tris(propan-2-yl)silyl]-1H-indole-5-carboxylic acid (1.86 g) in dichloromethane (18 mL) and N,N-dimethylformamide (7 mL) was added N-chlorosuccinimide (0.741 g) and the reaction stirred at room temperature under nitrogen for 3 h. Dimethylsulfoxide (10 mL) was added and the reaction stirred at room temperature for 1.5 h. The dichloromethane was removed in vacuo and the reaction left to stand at room temperature for 7 days. The reaction was then diluted with dichloromethane (8 mL) and N,N-dimethylformamide (12 mL) and further N-chlorosuccinimide (0.518 g) added. The reaction was stirred for 4 h, N-chlorosuccinimide (0.518 g) added and stirring continued over 16 hours. Further N-chlorosuccinimide (0.518 g×3) was added and the reaction mixture stirred for a further 24 hours. The reaction mixture was concentrated in vacuo and the residue partitioned between ethyl acetate and water. The aqueous layer was acidified with 1 M hydrochloric acid (pH=1-2) and extracted with ethyl acetate. The combined organic layers were washed with water, dried and concentrated.

The residue thus obtained was dissolved in N,N-dimethylformamide (15 mL) and the solution cooled to 0° C. Sodium hydride (611 mg, 63% dispersion in oil) was added and the reaction stirred at 0° C. for 10 minutes, methyl iodide (1.33 mL) was then added and the reaction stirred a further 10 minutes before diluting with N,N-dimethylformamide (15 mL) and stirring for 40 minutes at room temperature. A saturated solution of aqueous ammonium chloride (20 mL) was added and the reaction partitioned between ethyl acetate and water. The aqueous layer was extracted with ethyl acetate and the combined organic fractions washed with water, dried and concentrated. The crude product was purified by column chromatography (dichloromethane, then 20-30% ethyl acetate/dichloromethane) to give methyl 3-chloro-4-fluoro-1-methyl-1H-indole-5-carboxylate (1.04 g) as a yellow solid.

The ester thus obtained was dissolved in a mixture of tetrahydrofuran (10 mL), methanol (10 mL) and dichloromethane (3 mL). 2 M sodium hydroxide (4.31 mL) was added and the mixture stirred at room temperature for 3 h. Further 2 M sodium hydroxide (4.31 mL) was added and the reaction stirred at room temperature for 16 h. The mixture was concentrated in vacuo, diluted with water and ethyl acetate added. The resultant emulsion was acidified with 1 M hydrochloric acid (pH=2-3) and extracted with ethyl acetate. The combined ethyl acetate phases were dried and concentrated to give the title compound (0.274 g) as a pale yellow solid.

ESI MS m/z 228 (M+H)$^+$

Example 93

4-[({(2S,4R)-1-[(3-chloro-4-fluoro-1-methyl-1H-indol-5-yl)carbonyl]-4-[1-(methylsulfonyl)-4-piperidinyl]-2-pyrrolidinyl}carbonyl)amino]benzoic acid

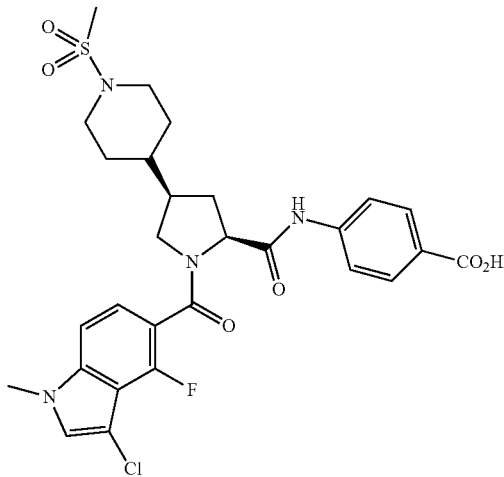 [SMILES: Cn1cc(Cl)c2c(F)c(C(=O)N3C[C@@H](C4CCN(S(C)(=O)=O)CC4)C[C@H]3C(=O)Nc3ccc(C(=O)O)cc3)ccc21]

Allyl 4-[({(2S,4R)-1-[(3-chloro-4-fluoro-1-methyl-1H-indol-5-yl)carbonyl]-4-[1-(methylsulfonyl)-4-piperidinyl]-2-pyrrolidinyl}carbonyl)amino]benzoate was prepared from the compound prepared in Example 63 following the procedures described in Example 5, 9 and 8. (Note: in the step corresponding to Example 5, allyl 4-aminobenzoate was used in place of tert-butyl 4-aminobenzoate. In the step corresponding to Example 8, the acid prepared in Example 92 was used in place of 1-(N,N'-bis(tert-butoxycarbonyl)carbamimidoyl)piperidine-4-carboxylic acid). After that, the crude allyl ester was treated with palladium(0) following the procedure described in Example 91 to give the title compound as an off-white solid.

$^1$H NMR (500 MHz, DMSO-d$_6$, rotamers present) δ 12.74 (br. s, 1H), 10.50 (s, 1H), 7.91 (d, 2H), 7.76 (d, 2H), 7.65 (s, 1H), 7.42 (d, 1H), 7.22 (dd, 1H), 4.61 (t, 1H), 3.80 (s, 3H), 3.58-3.38 (m, 3H), 3.27 (t, 1H), 2.80 (s, 3H), 2.65-2.55 (m, 3H), 2.09-1.98 (m, 1H), 1.82-1.73 (m, 1H), 1.62 (dd, 1H), 1.52-1.45 (m, 1H), 1.40-1.26 (m, 1H), 1.25-1.09 (m, 2H).

ESI MS m/z 605 (M+H)$^+$

Example 94 methyl [4-(4-chloro-2-{(2S,4R)-1-{(2E)-3-[5-chloro-2-(1H-tetrazol-1-yl)phenyl]-2-propenoyl}-4-[1-(methylsulfonyl)-4-piperidinyl]-2-pyrrolidinyl}-1H-imidazol-5-yl)phenyl]carbamate

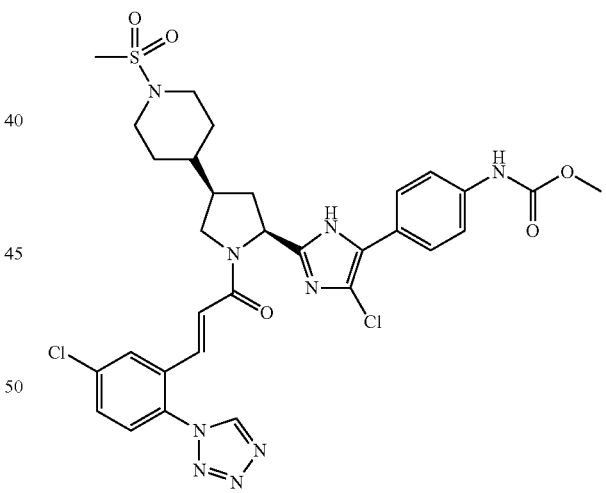

Following the procedure described in Example 68, the compound prepared in Example 67 was treated with (2E)-3-[5-chloro-2-(1H-tetrazol-1-yl)phenyl]acrylic acid to give the title compound as a white solid.

$^1$H NMR (300 MHz, DMSO-d$_6$, rotamers present) δ 12.80 (br. s, 0.3H), 12.40 (br. s, 0.7H), 9.95-9.64 (m, 2H), 8.42-6.58 (m, 8H), 7.24 (d, 0.7H), 6.97 (d, 0.3H), 6.80 (d, 0.7H), 6.67 (d, 0.3H), 5.23 (t, 0.3H), 4.86 (t, 0.7H), 4.18 (br. t, 0.7H), 3.97 (q, 0.3H), 3.80-2.30 (m, 12H), 2.20-1.61 (m, 3H), 1.55-0.96 (m, 3H).

FAB MS m/z 714 (M+H)$^+$

Example 95 methyl [4-(4-chloro-2-{(2S,4R)-1-[(3-chloro-4-fluoro-1-methyl-1H-indol-5-yl)carbonyl]-4-[1-(methylsulfonyl)-4-piperidinyl]-2-pyrrolidinyl}-1H-imidazol-5-yl)phenyl]carbamate

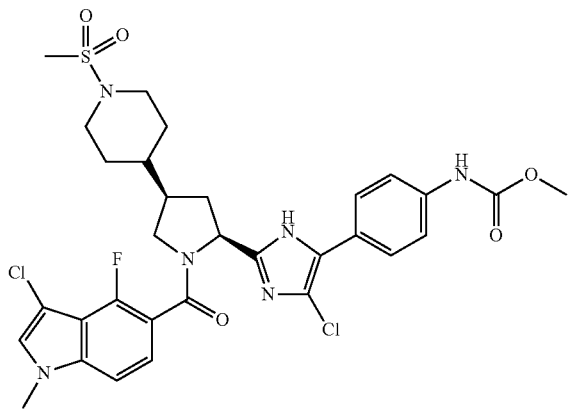 [SMILES: COC(=O)Nc1ccc(-c2[nH]c([C@@H]3C[C@H](C4CCN(S(C)(=O)=O)CC4)CN3C(=O)c3ccc4c(c(Cl)cn4C)c3F)nc2Cl)cc1]

Following the procedure described in Example 68, the compound prepared in Example 67 was treated with the compound prepared in Example 92 to give the title compound as a white solid.

$^1$H NMR (300 MHz, DMSO-d$_6$, rotamers present) δ 12.60 (s, 0.6H), 11.90 (s, 0.4H), 9.77 (s, 0.6H), 9.72 (s, 0.4H), 7.81-6.47 (m, 7H), 5.05 (t, 0.6H), 4.69 (br. t, 0.4H), 4.14-3.19 (m, 9H), 2.87 (s, 1.8H), 2.71 (s, 1.2H), 2.70-2.28 (m, 4H), 2.18-1.66 (m, 4H), 1.59-1.01 (m, 3H).

ESI MS m/z 691 (M+H)$^+$

Example 96 methyl [4-(2-{(2S,4R)-1-{[4-(aminomethyl)cyclohexyl]carbonyl}-4-[1-(methylsulfonyl)-4-piperidinyl]-2-pyrrolidinyl}-4-chloro-1H-imidazol-5-yl)phenyl]carbamate bis(trifluoroacetate)

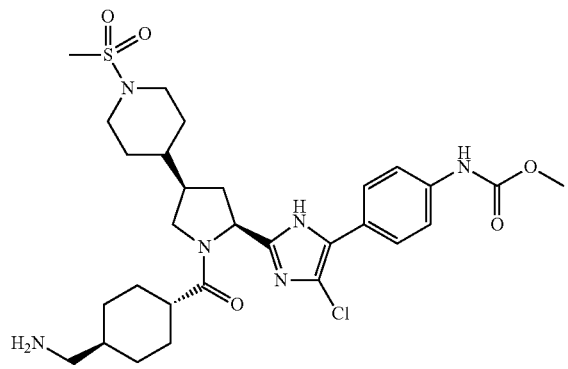 [SMILES: COC(=O)Nc1ccc(-c2[nH]c([C@@H]3C[C@H](C4CCN(S(C)(=O)=O)CC4)CN3C(=O)[C@H]3CC[C@H](CN)CC3)nc2Cl)cc1]

Following the procedure described in Example 68, the compound prepared in Example 67 was treated with trans-4-(tert-butoxycarbonylamino)-cyclohexanecarboxylic acid. After this, the crude amide was treated with TFA following the procedure described in Example 9 to give the title compound as a white solid.

$^1$H NMR (300 MHz, CD$_3$OD, rotamers present) δ 7.96-7.22 (m, 4H), 5.27-4.50 (m, 1H), 4.18-3.91 (m, 1H), 3.86-3.59 (m, 5H), 3.50 (br. t, 1H), 3.00-2.41 (m, 7H), 2.41-2.06 (m, 1H), 2.06-1.69 (m, 8H), 1.69-0.50 (m, 9H).

ESI MS m/z 621 (M+H)$^+$

Example 97 methyl [4-(2-{(2S,4S)-1-(4-carbamimidoylbenzoyl)-4-[4-(methylsulfonyl)-1-piperazinyl]-2-pyrrolidinyl}-1H-imidazol-5-yl)phenyl]carbamate trihydrochloride

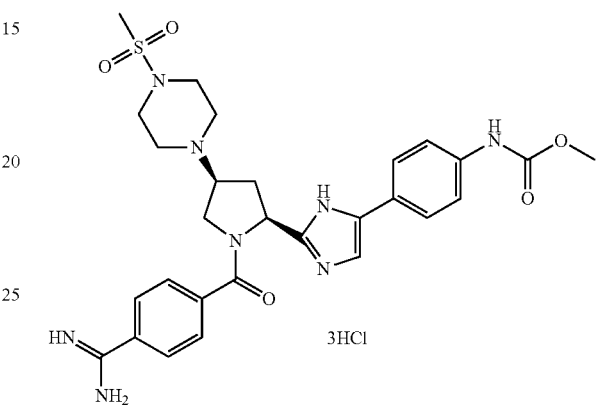

The compound prepared in Example 4 was treated following the procedures described in Example 64, 6, 8 and 69 to give the title compound as a white solid. (Note: in the step corresponding to Example 8, the compound prepared in Example 18 was used)

$^1$H NMR (300 MHz, CD$_3$OD, rotamers present) δ 7.91 (d, 2H), 7.89 (d, 2H), 7.75 (s, 1H), 7.65 (dd, 2H), 7.60 (dd, 2H), 5.38 (dd, 1H), 3.90-3.60 (m, 6H), 2.80 (s, 3H), 2.79-2.60 (m, 3H), 2.35-2.18 (m, 1H), 2.10-1.80 (m, 2H), 1.65-1.25 (m, 4H).

ESI MS m/z 595 (M+H)$^+$

Example 98 methyl [4-(2-{(2S,4S)-1-[(1-carbamimidoyl-4-piperidinyl)carbonyl]-4-[4-(methylsulfonyl)-1-piperazinyl]-2-pyrrolidinyl}-1H-imidazol-5-yl)phenyl]carbamate trihydrochloride

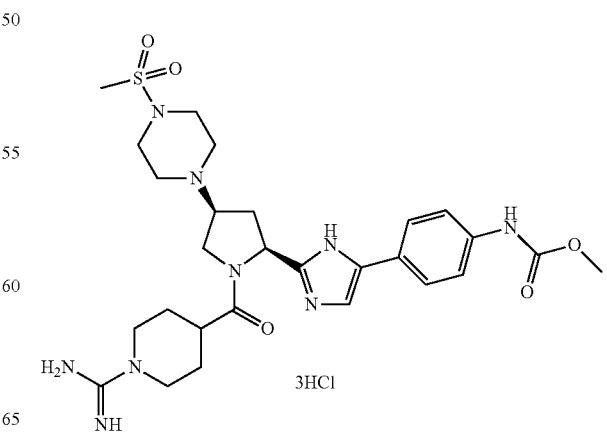

The compound prepared in Example 4 was treated following the procedures described in Example 64, 6, 8 and 69 to give the title compound as a white solid. (Note: in the step corresponding to Example 8, the compound prepared in Example 7 was used)

$^1$H NMR (300 MHz, DMSO-d$_6$, rotamers present) δ 9.90 (s, 1H), 7.94 (s, 1H), 7.85 (d, 2H), 7.60 (s, 2H), 7.52-7.31 (m, 3H), 5.21 (t, 1H), 4.51-2.20 (m, 24H), 2.05-1.89 (m, 1H), 1.89-1.69 (m, 1H), 1.57-1.25 (m, 2H).

ESI MS m/z 602 (M+H)$^+$

Example 99 methyl [4-(2-{(2S,4S)-1-[(1-carbamimidoyl-4-piperidinyl)carbonyl]-4-[4-(methylsulfonyl)-1-piperazinyl]-2-pyrrolidinyl}-4-chloro-1H-imidazol-5-yl)phenyl]carbamate trihydrochloride

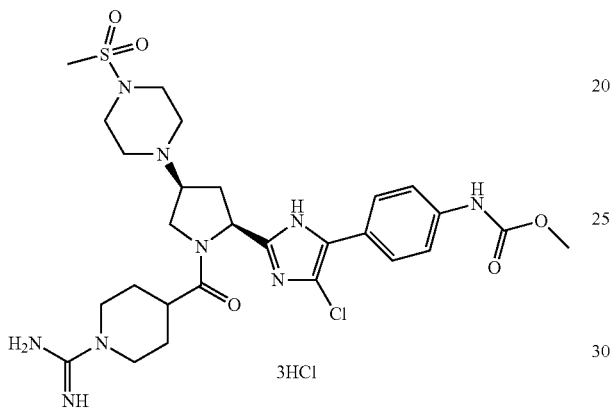

The compound prepared in Example 4 was treated following the procedures described in Example 64, 65, 6, 8 and 69 to give the title compound as a white solid. (Note: in the step corresponding to Example 8, the compound prepared in Example 7 was used)

$^1$H NMR (300 MHz, DMSO-d$_6$, rotamers present) δ 9.83 (s, 0.5H), 9.84 (s, 0.5H), 7.84 (d, 1H), 7.24 (d, 1H), 7.58-7.49 (m, 2H), 7.49-7.18 (m, 4H), 5.40 (t, 0.5H), 4.93 (t, 0.5H), 4.42-2.30 (m, 24H), 1.93-0.49 (m, 4H).

ESI MS m/z 636 (M+H)$^+$

Example 100

(3-chloro-4-fluoro-1-methyl-1H-indol-5-yl)[(2S,4S)-2-(4-chloro-5-phenyl-1H-imidazol-2-yl)-4-(4-morpholinyl)-1-pyrrolidinyl]methanone bis(trifluoroacetate)

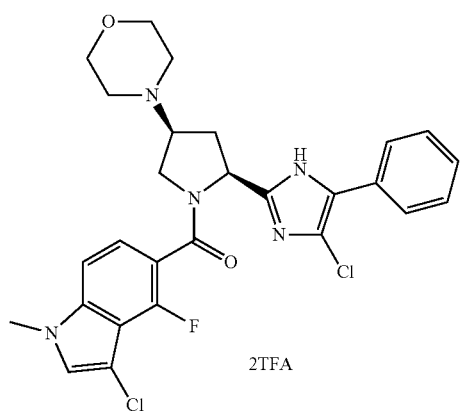 [SMILES: Cn1cc(Cl)c2c(F)c(C(=O)N3C[C@@H](N4CCOCC4)C[C@H]3c3nc(Cl)c(-c4ccccc4)[nH]3)ccc21]

The compound prepared in Example 2 was treated following the procedures described in Examples 3, 4, 64, 65, 6 and 8 to give the title compound after purification by high performance liquid chromatography [5 to 100% mobile phase B (0.1% trifluoroacetic acid in acetonitrile) in mobile phase A (0.1% trifluoroacetic acid in water)] as a white solid. (Note: in the steps corresponding to Examples 3, 64 and 8, morpholine, 2-bromo-1-phenylethane-1-one and the compound prepared in Example 92 were used respectively)

$^1$H NMR (500 MHz, CDCl$_3$, rotamers present) δ 10.92 (app. br. s, 3H), 7.81 (d, 1H), 7.72-7.58 (m, 1H), 7.49-7.31 (m, 3H), 7.30-6.99 (m, 3H), 6.02-5.62 (m, 1H), 4.65-4.28 (m, 1H), 4.24-3.84 (m, 6H), 3.81-3.61 (m, 3H), 3.60-2.89 (m, 6H).

ESI MS m/z 542/544 (M+H)$^+$

Example 101

(2E)-3-[5-chloro-2-(1H-tetrazol-1-yl)phenyl]-1-[(2S,4S)-4-(4-morpholinyl)-2-(5-phenyl-1H-imidazol-2-yl)-1-pyrrolidinyl]-2-propen-1-one

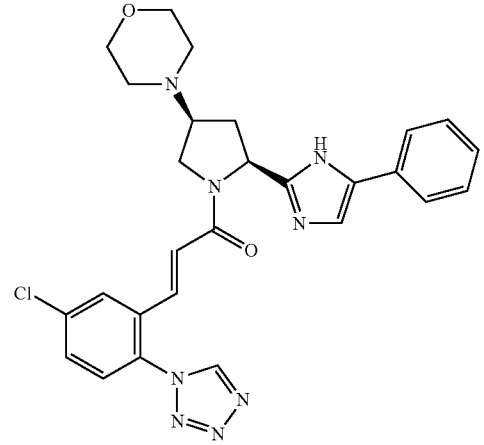 [SMILES: O=C(/C=C/c1cc(Cl)ccc1-n1cnnn1)N1C[C@@H](N2CCOCC2)C[C@H]1c1ncc(-c2ccccc2)[nH]1]

The compound prepared in Example 2 was treated following the procedures described in Examples 3, 4, 64, 6 and 8 to give the title compound as a white solid. (Note: in the step corresponding to Example 3, 64 and 8, morpholine, 2-bromo-1-phenylethane-1-one and (2E)-3-[5-chloro-2-(1H-tetrazol-1-yl)phenyl]acrylic acid were used respectively)

$^1$H NMR (500 MHz, CDCl$_3$, rotamers present) δ 8.69 (s, 1H), 7.87 (d, 1H), 7.78-7.67 (m, 1H), 7.64 (d, 1H), 7.47 (dd, 1H), 7.43-7.28 (m, 4H), 7.26-7.19 (m, 2H), 7.04 (d, 1H), 5.39 (dd, 1H), 4.23 (d, 1H), 3.90-3.71 (m, 6H), 3.65 (dd, 1H), 2.97-2.81 (m, 1H), 2.78-2.62 (m, 2H), 2.63-2.54 (m, 2H).

ESI MS m/z 531 (M+H)$^+$

Example 102

(2E)-1-[(2S,4S)-2-(4-chloro-5-phenyl-1H-imidazol-2-yl)-4-(4-morpholinyl)-1-pyrrolidinyl]-3-[5-chloro-2-(1H-tetrazol-1-yl)phenyl]-2-propen-1-one

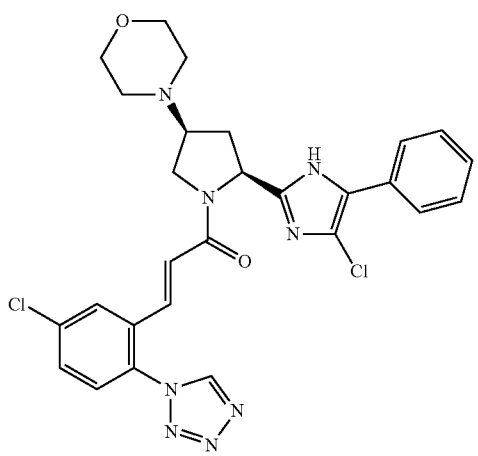 [SMILES: O=C(/C=C/c1cc(Cl)ccc1-n1cnnn1)N1C[C@@H](N2CCOCC2)C[C@H]1c1nc(Cl)c(-c2ccccc2)[nH]1]

The compound prepared in Example 2 was treated following the procedures described in Examples 3, 4, 64, 65, 6 and 8 to give the title compound as a white solid. (Note: in the step corresponding to Example 3, 64 and 8, morpholine, 2-bromo-1-phenylethane-1-one and (2E)-3-[5-chloro-2-(1H-tetrazol-1-yl)phenyl]acrylic acid were used respectively)

$^1$H NMR (500 MHz, CDCl$_3$, rotamers present) δ 12.60 (br. s, 1H), 8.85 (s, 1H), 7.90 (s, 1H), 7.74-7.60 (m, 2H), 7.57 (dd, 1H), 7.49-7.38 (m, 3H), 7.38-7.20 (m, 2H), 7.10 (d, 1H), 5.32-5.21 (m, 1H), 4.25 (d, 1H), 3.96 (dd, 1H), 3.87-3.57 (m, 4H), 3.08 (br. s, 1H), 2.90 (dd, 1H), 2.75-2.40 (m, 5H).

ESI MS m/z 565/567 (M+H)$^+$

Example 103 benzyl 3-acetylbenzoate

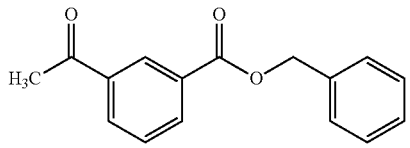 [SMILES: CC(=O)c1cccc(C(=O)OCc2ccccc2)c1]

To a solution of 3-acetylbenzoic acid (6.00 g, 0.36 mol) in DMF (36 mL) was added Na$_2$CO$_3$ (4.26 g, 0.40 mol) at 0° C. and the reaction stirred for 10 min. After 10 min, benzyl bromide (4.80 mL, 0.40 mol) was added and the reaction stirred at room temperature for 1 h. The reaction mixture was diluted with EtOAc (100 mL) and washed with H$_2$O (50 mL) and brine (50 mL), dried over Na$_2$SO$_4$, filtered and concentrated. The residue was purified by combiflash chromatography (silica gel, 40 g, 2-5% ethyl acetate/hexanes) to afford the title compound (7.73 g, 84%) as a white solid.

$^1$H NMR (300 MHz, CDCl$_3$) δ 8.61 (dd, 1H), 8.26 (ddd, 1H), 8.15 (ddd, 1H), 7.54 (t, 1H), 7.45-7.37 (m, 5H), 5.40 (s, 2H), 2.63 (s, 3H).

Example 104 benzyl 3-(2-bromoacetyl)benzoate

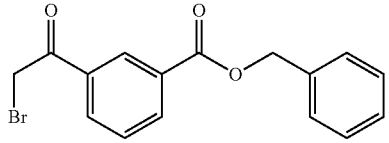 [SMILES: O=C(CBr)c1cccc(C(=O)OCc2ccccc2)c1]

To a solution of compound prepared in Example 103 (8.40 g, 0.33 mol) in THF (160 mL) was added Phenyl Trimethylammonium Tribromide (12.40 g, 0.33 mol) and the reaction mixture stirred at room temperature for 1 h. The reaction mixture was diluted with EtOAc (100 mL) and washed with H$_2$O (50 mL) and brine (50 mL), dried over Na$_2$SO$_4$, filtered and concentrated. The residue was purified by combiflash chromatography (silica gel, 40 g, 2-3% ethyl acetate/hexanes) to afford the title compound (7.99 g, 55%) as a white solid.

$^1$H NMR (300 MHz, CDCl$_3$) δ 8.64 (dd, 1H), 8.31 (ddd, 1H), 8.18 (ddd, 1H), 7.58 (t, 1H), 7.47-7.36 (m, 5H), 5.40 (s, 2H), 4.47 (s, 2H).

Example 105

3-[2-[(2S,4R)-1-(1-carbamimidoylpiperidine-4-carbonyl)-4-(1-methylsulfonyl-4-piperidyl)pyrrolidin-2-yl]-1H-imidazol-5-yl]benzoic acid bis(trifluoroacetate)

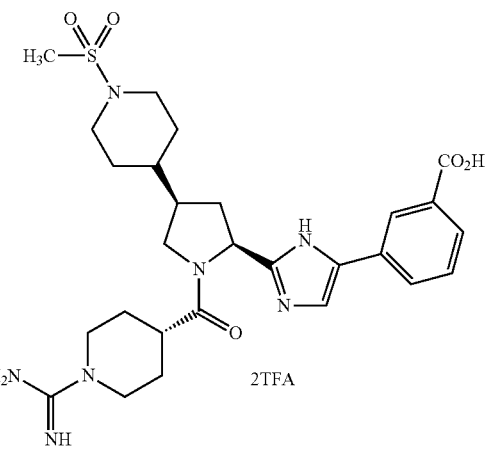

The compound prepared in Example 63 was treated following the procedures described in Examples 64, 66, 68, 6 and 9 to give the title compound as a white solid. (Note: in the steps corresponding to Examples 64, the compound prepared in Example 104 was used)

$^1$H NMR (300 MHz, D$_2$O) δ 8.19 (s, 1H), 7.98 (d, 1H), 7.83 (d, 1H), 7.61 (s, 1H), 7.61 (t, 1H), 5.19-5.16 (m, 1H), 4.11 (t, 1H), 3.85-3.81 (m, 2H), 3.70-3.57 (m, 3H), 3.20-3.11 (m, 2H), 3.00-2.98 (m, 4H), 2.84-2.71 (m, 3H), 2.32-2.30 (m, 1H), 1.92-1.80 (m, 5H), 1.66-1.60 (m, 3H), 1.48-1.43 (m, 2H).

ESI MS m/z 570 [C$_{27}$H$_{37}$N$_7$O$_5$S—H]$^-$

Example 106

3-[2-[(2S,4R)-1-[4-(aminomethyl)cyclohexanecarbonyl]-4-(1-methylsulfonyl-4-piperidyl)pyrrolidin-2-yl]-1H-imidazol-5-yl]benzoic acid bis(trifluoroacetate)

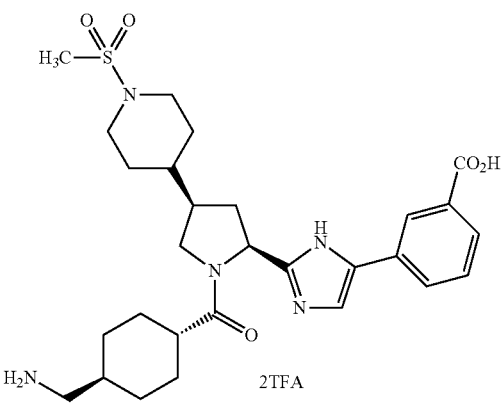 [SMILES: CS(=O)(=O)N1CCC([C@H]2C[C@@H](c3ncc(-c4cccc(C(=O)O)c4)[nH]3)N(C(=O)[C@H]3CC[C@H](CN)CC3)C2)CC1]

The compound prepared in Example 63 was treated following the procedures described in Examples 64, 66, 68, 6 and 9 to give the title compound as a white solid. (Note: in the steps corresponding to Examples 64 and 68, the compound prepared in Example 104 and trans-4-[({[(2-methyl-2-propanyl)oxy]carbonyl}amino)methyl]cyclohexanecarboxylic acid were used respectively)

$^1$H NMR (400 MHz, DMSO-d$_6$) δ 8.35 (s, 1H), 8.15 (s, 1H), 8.03-7.97 (m, 2H), 7.75 (br s, 3H), 7.65 (t, 1H), 5.03-4.99 (m, 1H), 3.95 (t, 1H), 3.62-3.52 (m, 2H), 3.46 (t, 1H), 2.85 (s, 3H), 2.72-2.70 (m, 4H), 2.58-2.42 (m, 1H), 2.29-2.12 (m, 1H), 1.89-1.66 (m, 7H), 1.54-0.98 (m, 9H).

APCI MS m/z 558 [C$_{28}$H$_{39}$N$_5$O$_5$S+H]$^+$

Example 107 methyl N-[4-[2-[(2S,4R)-1-[4-(aminomethyl)cyclohexanecarbonyl]-4-(1-methylsulfonyl-4-piperidyl)pyrrolidin-2-yl]-1H-imidazol-5-yl]phenyl]carbamate bishydrochloride

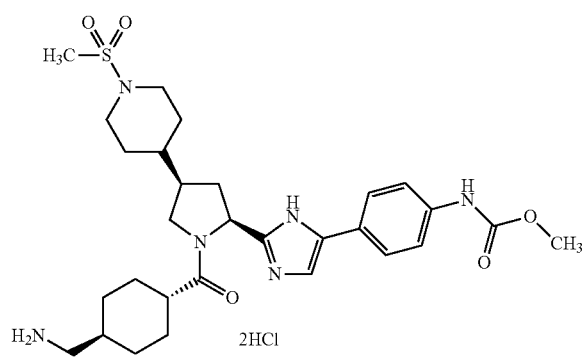 [SMILES: COC(=O)Nc1ccc(-c2cnc([C@@H]3C[C@H](C4CCN(S(C)(=O)=O)CC4)CN3C(=O)[C@H]3CC[C@H](CN)CC3)[nH]2)cc1]

Following the procedure described in Example 68, the compound prepared in Example 66 was treated with trans-4-(tert-butoxycarbonylamino)-cyclohexanecarboxylic acid. After this, the crude amide was treated following the procedure described in Example 69 to give the title compound as a white solid.

$^1$NMR (400 MHz, DMSO-d$_6$, rotamers present) δ 12.04 (br. s, 0.4H), 9.93 (br s, 0.6H), 7.84-7.78 (m, 7H), 7.57-7.52 (m, 2H), 5.11-5.00 (m, 0.62H), 3.93-3.86 (m, 0.69H), 3.71-3.68 (m, 1H), 3.68 (s, 3H), 3.61-3.53 (m, 2H), 3.52-3.44 (m, 1H), 2.85 (s, 3H), 2.69-2.60 (m, 4H), 2.18-2.09 (m, 1H), 1.95-1.89 (m, 2H), 1.82-1.74 (m, 5H), 1.55-1.42 (m, 2H), 1.36-1.18 (m, 5H), 1.06-0.98 (m, 3H).

ESI MS m/z 585 [C$_{29}$H$_{42}$N$_6$O$_5$S—H]$^-$

Example 108 benzyl N-[5-(2-bromoacetyl)-2-pyridyl]carbamate

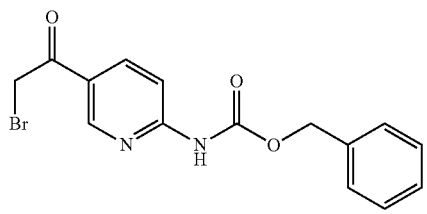 [SMILES: O=C(Nc1ccc(C(=O)CBr)cn1)OCc1ccccc1]

Benzyl N-(5-acetyl-2-pyridyl)carbamate was treated following the procedures described in Example 103 to give the title compound.

$^1$H NMR (300 MHz, DMSO-d$_6$, rotamers present) δ 10.93-10.68 (m, 1H), 8.99-8.78 (m, 1H), 8.41-8.19 (m, 1H), 8.05-7.89 (m, 1H), 7.48-7.25 (m, 5H), 5.21 (s, 2H), 4.93-4.83 (m, 1.5H), 4.77-4.67 (m, 0.5H).

Example 109

4-[(2S,4R)-2-[5-(6-amino-3-pyridyl)-1H-imidazol-2-yl]-4-(1-methylsulfonyl-4-piperidyl)pyrrolidine-1-carbonyl]piperidine-1-carboxamidine tri(trifluoroacetate)

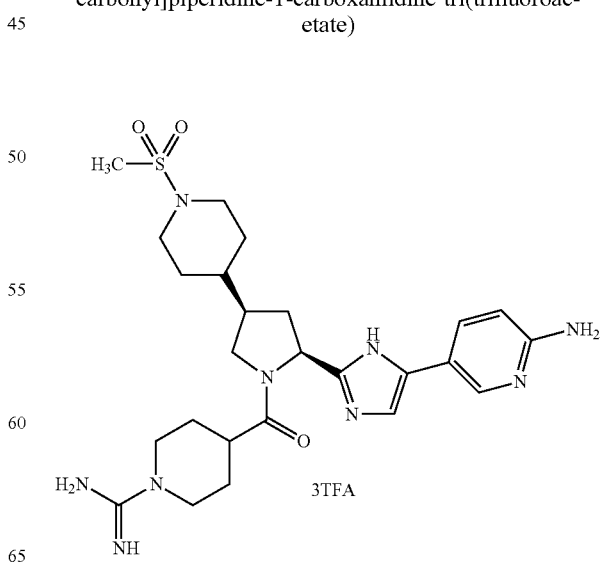

The compound prepared in Example 63 was treated following the procedures described in Examples 64, 66, 68 and 9 to give the title compound as a white semi-solid. (Note: in the steps corresponding to Examples 64, the compound prepared in Example 108 was used)

$^1$H NMR (400 MHz, D$_2$O) δ 8.07 (s, 1H), 8.04 (d, 1H), 7.57 (s, 1H), 7.08 (d, 1H), 5.12 (t, 1H), 4.07 (t, 1H), 3.80 (d, 2H), 3.64 (d, 2H), 3.53 (t, 1H), 3.10 (t, 2H), 2.99-2.23 (m, 1H), 2.91 (s, 3H), 2.82-2.62 (m, 3H), 2.33-2.19 (m, 1H), 1.91-1.73 (m, 5H), 1.60-1.44 (m, 3H), 1.44-1.27 (m, 2H).

ESI MS m/z 544 [C$_{25}$H$_{37}$N$_9$O$_3$S+H]$^-$

Example 110

4-[I{(2S,4R)-1-[(1-carbamimidoyl-4-piperidinyl)carbonyl]-4-[1-(methylsulfonyl)-4-piperidinyl]-2-pyrrolidinyl}carbonyl)amino]benzoic acid hydrochloride

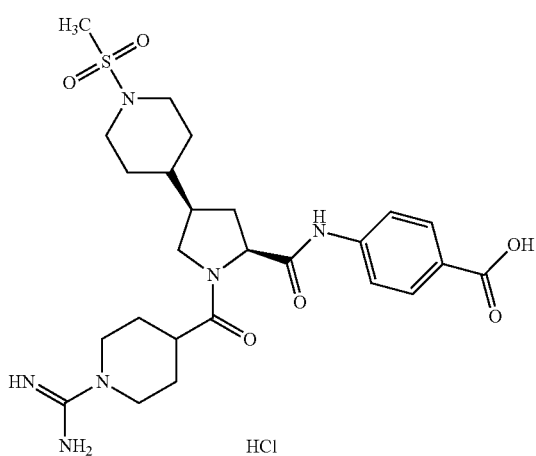 [SMILES: CS(=O)(=O)N1CCC([C@H]2C[C@@H](C(=O)Nc3ccc(C(=O)O)cc3)N(C(=O)C3CCN(C(=N)N)CC3)C2)CC1 ; Cl]

The compound prepared in Example 63 was treated following the procedures described in Examples 5, 66, 68 and 69 to give the title compound as a white powder.

$^1$H NMR (CD$_3$OD, 400 MHz) δ 7.99 (d, 2H), 7.58 (d, 2H), 4.47-4.41 (m, 1H), 4.02 (t, 1H), 3.90-3.79 (m, 2H), 3.69-3.61 (m, 2H), 3.36 (t, 1H), 3.23-3.08 (m, 2H), 2.94 (s, 4H), 2.82-2.69 (m, 2H), 2.61-2.49 (m, 1H), 2.09-2.22 (m, 1H), 1.98-1.74 (m, 4H), 1.72-1.56 (m, 3H) 1.51-1.25 (m, 3H).

ESI MS m/z 549 [C$_{25}$H$_{36}$N$_6$O$_6$S+H]$^+$

Example 111

4-[({(2S,4R)-1-(4-carbamimidoylbenzoyl)-4-[1-(methylsulfonyl)-4-piperidinyl]-2-pyrrolidinyl}carbonyl)amino]benzoic acid hydrochloride

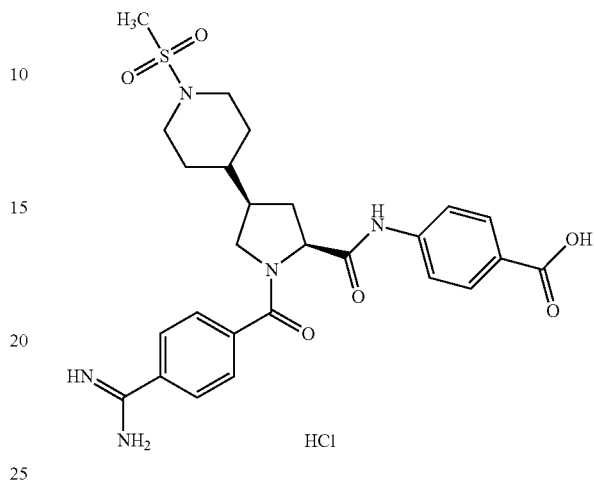

The compound prepared in Example 63 was treated following the procedures described in Examples 5, 66, 68 and 69 to give the title compound as a white solid. (Note: in the steps corresponding to Examples 68, the compound prepared in Example 18 was used)

$^1$H NMR (CD$_3$OD, 400 MHz) δ 7.98 (d, 2H), 7.91-7.85 (m, 4H), 7.75 (d, 2H), 4.77-4.69 (m, 1H), 3.77-3.60 (m, 3H), 3.51 (t, 1H), 2.79 (s, 3H), 2.75-2.60 (m, 3H), 2.17-2.07 (m, 1H), 1.92-1.85 (m, 1H), 1.84-1.73 (m, 1H), 1.64-1.56 (m, 1H), 1.49-1.22 (m, 3H).

ESI MS m/z 542 [C$_{26}$H$_{31}$N$_5$O$_6$S+H]$^+$

Example 112 benzyl 4-[({(2S,4S)-1-(4-{N'-[(benzyloxy)carbonyl]carbamimidoyl}benzoyl)-4-[4-(methylsulfonyl)-1-piperazinyl]-2-pyrrolidinyl}carbonyl)amino]benzoate

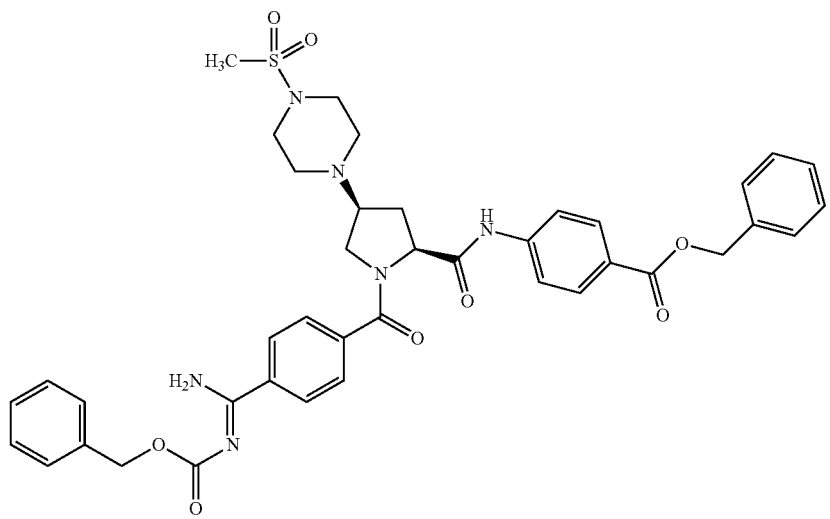 [SMILES: CS(=O)(=O)N1CCN([C@H]2C[C@@H](C(=O)Nc3ccc(C(=O)OCc4ccccc4)cc3)N(C(=O)c3ccc(/C(N)=N/C(=O)OCc4ccccc4)cc3)C2)CC1]

The compound prepared in Example 19 was treated following the procedures described in Examples 69, 2 and 22 to give the title compound as a white powder.

$^1$H NMR (300 MHz, DMSO-d$_6$) δ 10.49 (s, 1H), 9.17 (br. s, 2H), 8.03 (d, 2H), 7.95 (d, 2H), 7.76 (d, 2H), 7.66 (d, 2H), 7.49-7.24 (m, 10H), 5.31 (s, 2H), 5.10 (s, 2H), 4.62 (dd, 2H), 3.69-3.59 (m, 1H), 3.53 (t, 1H), 3.14-2.88 (m, 5H), 2.83 (s, 3H), 2.64-2.31 (m, 4H), 1.85-1.63 (m, 1H).

Example 113 ethyl 4-[({(2S,4S)-1-(4-carbamimidoylbenzoyl)-4-[4-(methylsulfonyl)-1-piperazinyl]-2-pyrrolidinyl}carbonyl)amino]benzoate bis(trifluoroacetate)

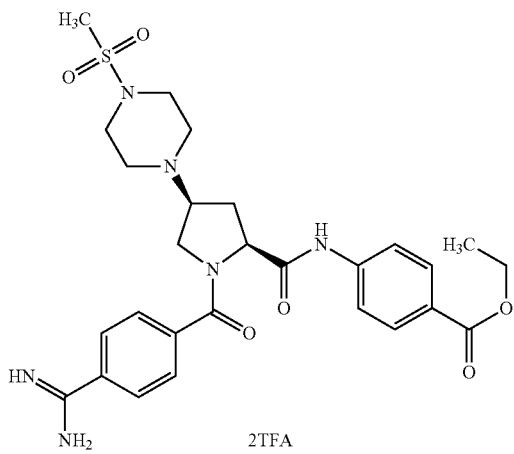 [SMILES: CCOC(=O)c1ccc(NC(=O)[C@@H]2C[C@H](N3CCN(S(C)(=O)=O)CC3)CN2C(=O)c2ccc(C(=N)N)cc2)cc1 ; "2TFA"]

To a stirred solution of compound prepared in Example 20 (500 mg) in ethanol (25 mL) was added concentrated sulfuric acid (20 drops) at 0° C. The resulting mixture was stirred at 60° C. for 44 h whereupon the mixture was concentrated in vacuo. The resulting residue was purified by Prep-HPLC (0.1% TFA containing CH$_3$CN—H$_2$O gradient) to provide the title compound (307 mg).

$^1$H NMR (300 MHz, D$_2$O, rotamers present) δ 8.07 (d, 1H), 7.97-7.93 (m, 2H), 7.86-7.77 (m, 2H), 7.69-7.65 (m, 2H), 7.22 (m, 1H), 4.90-4.35 (m, 3H), 4.12-3.75 (m, 3H), 3.60-3.13 (m, 8H), 3.09-2.97 (m, 4H), 2.31 (m, 1H), 1.44-1.34 (m, 3H).

FAB MS m/z 571 (M+H)$^+$

Example 114 benzyl 4-[({(2S,4S)-1-(4-cyanobenzoyl)-4-[4-(methylsulfonyl)-1-piperazinyl]-2-pyrrolidinyl}carbonyl)amino]benzoate

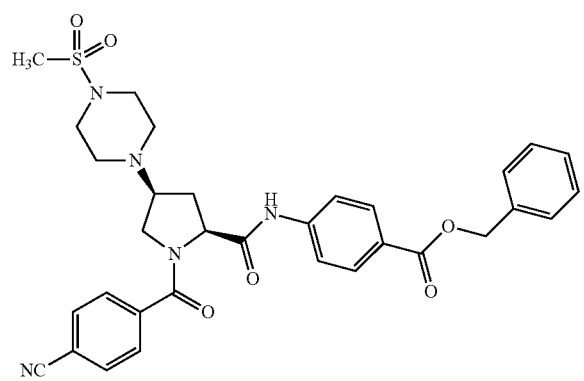 [SMILES: CS(=O)(=O)N1CCN([C@H]2C[C@@H](C(=O)Nc3ccc(C(=O)OCc4ccccc4)cc3)N(C(=O)c3ccc(C#N)cc3)C2)CC1]

The compound prepared in Example 4 was treated following the procedures described in Examples 5, 6 and 8 to give the title compound having the following physical properties. (Note: in the steps corresponding to Examples 5 and 8, benzyl 4-aminobenzoate and 4-cyanobenzoic acid were used respectively)

TLC: Rf 0.57 (5% methanol in ethyl acetate)

Example 115 benzyl 4-[({(2S,4S)-1-[4-(N'-hydroxycarbamimidoyl)benzoyl]-4-[4-(methylsulfonyl)-1-piperazinyl]-2-pyrrolidinyl}carbonyl)amino]benzoate

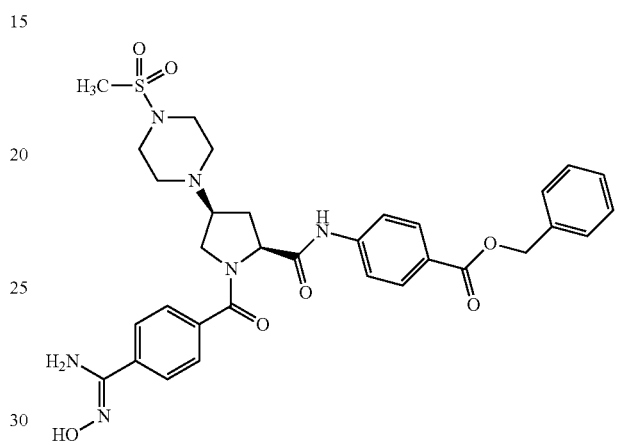

To a stirred solution of compound prepared in Example 114 (1.04 g) in N,N-dimethylformamide (8 mL) were added potassium phosphate (550 mg) and hydroxylamine hydrochloride (225 mg) at room temperature. The resulting mixture was stirred at 70° C. for 21 h. whereupon the mixture was diluted with dichloromethane (20 mL). The insoluble materials are removed by filtration. The filtrate was concentrated in vacuo and the residue purified by column chromatography (silica gel, 0-15% methanol/ethyl acetate) to give the title compound (384 mg).

$^1$H NMR (300 MHz, DMSO-d$_6$, rotamers present) δ 10.05 (br. s, 1H), 9.77 (s, 1H), 7.97-7.94 (m, 2H), 7.78-7.73 (m, 4H), 7.59-7.56 (m, 2H), 7.47-7.26 (m, 5H), 5.88 (br. s, 2H), 5.31 (s, 2H), 4.61 (m, 1H), 3.67-3.52 (m, 2H), 3.12-3.00 (m, 4H), 2.95-2.72 (m, 5H), 2.62-2.34 (m, 4H), 1.76 (m, 1H).

ESI MS m/z 649 (M+H)$^+$

PHARMACOLOGICAL ACTIVITIES

The compounds of the present invention possess factor XIa inhibitory activity, for example, such an effect of the compounds of the present invention was confirmed by the following tests.

All the procedures were conducted by conventionally used techniques on the basis of basic biological methods. Furthermore, the measuring method of the present invention was modified to improve the accuracy and/or sensitivity of measurement for evaluating the compound of the present invention. The detailed experimental method was as follows.

EXPERIMENTAL METHOD (1) In Vitro Assay

Inhibitory activities of compounds of the present invention against factor XIa, Xa, XIIa, IXa, VIIa, plasma kallikrein or thrombin were evaluated using appropriate purified proteases and synthetic substrates. The rate of hydrolysis of the chromogenic substrate by the relevant protease was continuously measured at 405 nm. Inhibitory activity against each enzyme was calculated as % inhibition using the equation described below.

% Inhibition=[[(rate without compound)−(rate with compound)]/(rate without compound)]×100%.

Each half maximal inhibitory concentration ($IC_{50}$) value was determined by plotting the concentration of compound of the invention against the % inhibition.

(1-1) Factor XIa Enzyme Activity

Human Factor XIa (Haematologic Technologies Inc.) activity was measured at an enzyme concentration of 0.1 U/mL in 150 mM NaCl, 5 mM KCl, 1 mg/mL PEG6000, 50 mM HEPES-NaOH (pH7.4) with 300 μM S-2366 (pyroGlu-Pro-Arg-pNA, Chromogenix).

(1-2) Plasma Kallikrein Enzyme Activity

Human plasma kallikrein (Enzyme Research Laboratories Ltd) activity was measured at an enzyme concentration of 0.605 mU/mL in 200 mM NaCl, 5 mg/mL PEG6000, 100 mM Phosphate-NaOH (pH7.4) with 150 μM S-2302 (H-D-Pro-Phe-Arg-pNA, Chromogenix).

(1-3) Factor Xa and Thrombin Enzyme Activity

Human Factor Xa (American Diagnostica Inc.) and human thrombin (Sigma) activities were measured at the enzyme concentrations of 0.18 U/mL and 0.12 U/mL, respectively in the same buffer containing 150 mM NaCl, 2 mg/mL PEG6000, 50 mM Tris-HCl (pH7.4), except that the reactions were started with 300 μM S-2222 (phenyl-Ile-Glu-Gly-Arg-pNA, Chromogenix) and 300 μM S-2366, respectively.

(1-4) Factor XIIa Enzyme Activity

Human Factor α-XIIa (Enzyme Research Laboratories Ltd) activity was measured at an enzyme concentration of 0.17 U/mL in 150 mM NaCl, 50 mM Tris-HCl (pH7.4) with 300 μM S-2302 (Pro-Phe-Arg-pNA, Chromogenix).

(1-5) Factor IXa Enzyme Activity

Human Factor IXa (American Diagnostica Inc.) activity was measured at an enzyme concentration of 13 U/mL in 100 mM NaCl, 5 mM $CaCl_2$, 30% ethylene glycol, 50 mM Tris-HCl (pH7.4) with 3 mM Pefachrome IXa 3960 (Leu-Ph'Gly-Arg-pNA, Pentapharm).

(1-6) Factor VIIa Enzyme Activity

Human Factor VIIa activity was measured using recombinant human factor VIIa (American Diagnostica Inc.) in the presence of recombinant human tissue factor which was produced according to the method described in the literature (Protein expression and purification, 3, 453-460 (1992) in a buffer containing 150 mM NaCl, 5 mM $CaCl_2$, 0.5 mg/mL PEG6000, 50 mM HEPES-NaCl (pH7.4) with 3 mM S-2288 (Ile-Pro-Arg-pNA, Chromogenix).

(1-7) APTT, PT Mesurement

Activated partial thromboplastin time (APTT) and prothrombin time (PT) were measured using automatic coagulation analyzer (CA-1500, Sysmex Corporation). For the APTT or PT measurement, standard human plasma (Siemens Healthcare Diagnostics GmbH) were mixed with each compound dilutions followed by the automatic addition of APTT reagent (Siemens Healthcare Diagnostics GmbH) and 0.02 M calcium chloride or PT reagent (Siemens Healthcare Diagnostics GmbH) to start clot formation. The anticoagulant activities (APTT2 or PT2) of the compounds of the invention were expressed as the concentrations necessary to double the clotting time in vehicle (1% DMSO) group.

APTT2 or PT2 was determined by plotting the concentration of compound of the invention against the fold increase of clotting time.

The compounds of the present invention were tested in the factor XIa assay described above, and found to have a good factor XIa inhibitory activity as well as good selectivity against other plasma serine proteases. Table 1 described below lists factor XIa, thrombin and FXa $IC_{50}$ values measured for the following examples.

TABLE 1

| Example No | In vitro FXIa inhibitory activity $IC_{50}$ (μM) | In vitro Thrombin inhibitory activity $IC_{50}$ (μM) | In vitro FXa inhibitory activity $IC_{50}$ (μM) |
|---|---|---|---|
| 9 | 0.017 | >100 | >100 |
| 20 | 0.0032 | >100 | >100 |
| 37 | 0.013 | >100 | >100 |
| 39 | 0.078 | >100 | >100 |
| 43 | 0.011 | >100 | >100 |
| 55 | 0.014 | >100 | >100 |
| 57 | 0.027 | >100 | >100 |
| 69 | 0.0074 | >100 | >100 |
| 73 | 0.0044 | 37 | >100 |
| 79 | 0.0065 | 40 | >100 |
| 86 | 0.0099 | >100 | >100 |
| 88 | 0.0054 | 57 | >100 |
| 93 | 0.018 | >100 | >100 |
| 94 | 0.0054 | >33 | >33 |
| 96 | 0.0042 | >100 | >100 |
| 98 | 0.0023 | >100 | >100 |
| 71 | 0.0022 | 94 | >100 |
| 99 | 0.0012 | 84 | >100 |
| 111 | 0.0085 | >100 | Not tested |

Therefore, the results indicated that the compounds of the present invention possess factor XIa inhibitory activity as well as high selectivity against other plasma serine proteases.

Additionally, the good oral bioavailability of compounds of the present invention can be determined using the following experimental methods.

(2-1) Pharmacokinetic (PK) Study in Rat

Each compound of the present invention in a solution of 20% well solve (celeste) was given to fasted male Crj:CD (SD) rats as a single 3 mg/kg, p.o. dose by gavage. Blood samples were drawn from jugular vein into syringes containing 3.2% sodium citrate (the volume ratio of blood to anticoagulant=9:1) or heparinized syringes at 0.5, 1, 3, 7 hours after oral administration. Plasma was obtained by centrifugation and stored at −20° C. until measurement of plasma concentration.

To measure plasma concentrations of the compounds of the present invention, plasma samples were deproteinized with acetonitrile, followed by evaporation of the acetonitrile to dryness. Then the sample was reconstituted in the mobile phase and analyzed by LC/MS/MS. An analytical column (Shim-pack XR-ODSII, 2.0 mm×75 mm, 2.2 μm) and mobile phase (0.1% formic acid in water and 0.1% formic acid in acetonitrile, flow rate of 0.5 mL/min) were used. The system was used in multiple reaction monitoring (MRM) mode with positive ion detection.

(2-2) Pharmacokinetic (PK) Study of the Compound which has a Functional Group (e.g. an Ester Group, a Substitued Amidine Group, a Substituted Guanidine Group, Etc.) in Rat Each compound of the present invention in a solution of 20% well solve (celeste) was given to fasted male Crj:CD (SD) rats as a single 3 mg/kg, p.o. dose by gavage. Blood samples were drawn from jugular vein into syringes treated with heparin-diisopropyl fluorophosphate mixture (500:1) at 0.5, 1, 3, 7 hours after oral administration. Plasma was obtained by centrifugation and stored at −20° C. until measurement of plasma concentration.

To measure plasma concentrations of the compounds of the present invention, plasma samples were deproteinized with acetonitrile, followed by evaporation of the acetonitrile to dryness. Then the sample was reconstituted in the mobile phase and analyzed by LC/MS/MS. An analytical column (Shim-pack XR-ODSII, 2.0 mm×75 mm, 2.2 μm) and mobile phase (0.1% formic acid in water and 0.1% formic acid in acetonitrile, flow rate of 0.5 mL/min) were used. The system was used in multiple reaction monitoring (MRM) mode with positive ion detection.

Additionally, enzymatic hydrolysis of a functional group (e.g. an ester group, a substituted amidine group, a substituted guanidine group, etc.) in the compound of the present invention can be determined using the following experimental methods.

(3-1) Analysis of Enzymatic Hydrolysis of a Functional Group (e.g. an Ester Group, a Substitued Amidine Group, a Substituted Guanidine Group, Etc.) in the Compounds of the Present Invention Using Hepatocytes Prepared from Various Species (Rat, Dog, Monkey, Human)

A typical assay procedure was conducted by using cryopreserved hepatocytes prepared from various species. A mixture of hepatocytes, buffer (pH 7.4), and each test compound were incubated. The final test compound concentration was typically 100 ng/mL, with a usual cell density of 1,000,000 cells/ml for all species. The incubation was at 37° C., with time-points taken over 120 minutes. Reaction termination was achieved by addition of an aliquot of the hepatocyte/test compound mixture to acetonitrile/ethanol (7/3) to effect protein precipitation, followed by centrifugation. Then the sample was diluted with distilled water and analyzed by LC/MS/MS. An analytical column (Shim-pack XR-ODSII, 2.0 mm×75 mm, 2.2 μm) and mobile phase (0.1% formic acid in water and 0.1% formic acid in acetonitrile, flow rate of 0.5 mL/min) were used. The system was used in multiple reactions monitoring (MRM) mode with positive ion detection.

(3-2) Analysis of Enzymatic Hydrolysis of a Functional Group (e.g. an Ester Group, a Substitued Amidine Group, a Substituted Guanidine Group, Etc.) in the Compounds of the Present Invention Using Blood from Various Species (Rat, Dog, Monkey, Human)

Each compound of the present invention in a solution of acetonitrile were incubated in blood from various species. The incubation was typically performed at a concentration of 100 ng/mL of test compound at 37° C., with time points taken over 60 minutes. The reaction was terminated by addition of an aliquot of blood/test compound mixture to acetonitrile/ethanol (7/3) to effect protein precipitation, followed by centrifugation. Then the sample was diluted with distilled water and analyzed by LC/MS/MS. An analytical column (Shim-pack XR-ODSII, 2.0 mm×75 mm, 2.2 μm) and mobile phase (0.1% formic acid in water and 0.1% formic acid in acetonitrile, flow rate of 0.5 mL/min) were used. The system was used in multiple reactions monitoring (MRM) mode with positive ion detection.

Formulation Example 1

The following components were admixed in conventional method and punched out to obtain 10,000 tablets each containing 10 mg of active ingredient.

| | |
|---|---|
| Methyl [4-(4-chloro-2-{(2S,4R)-1-{(2E)-3-[5-chloro-2-(1H-tetrazol-1-yl)phenyl]-2-propenoyl}-4-[1-(methylsulfonyl)-4-piperidinyl]-2-pyrrolidinyl}-1H-imidazol-5-yl)phenyl]carbamate | 100 g |
| Carboxymethylcellulose calcium (disintegrating agent) | 20 g |
| Magnesium stearate (lubricating agent) | 10 g |
| Microcrystalline cellulose | 870 g |

Formulation Example 2

The following components were admixed in conventional method. The solution was sterilized in conventional manner, filtered through dust removal equipment, placed 5 mL portions into ampoules and sterilized by autoclave to obtain 10,000 ampoules each containing 20 mg of the active ingredient.

| | |
|---|---|
| Methyl [4-(4-chloro-2-{(2S,4R)-1-{(2E)-3-[5-chloro-2-(1H-tetrazol-1-yl)phenyl]-2-propenoyl}-4-[1-(methylsulfonyl)-4-piperidinyl]-2-pyrrolidinyl}-1H-imidazol-5-yl)phenyl]carbamate | 200 g |
| mannitol | 20 g |
| distilled water | 50 L |

INDUSTRIAL APPLICABILITY

The compounds of the present invention represented by formula (I) act as potent and selective inhibitors of factor XIa without side effects such as bleeding. In particular, the compounds of the present invention act as Factor XIa inhibitors. Thus the compounds of the present invention are useful in preventing and/or treating thromboembolic diseases, for example arterial cardiovascular thromboembolic disorders, venous cardiovascular thromboembolic disorders, arterial cerebrovascular thromboembolic disorders, venous cerebrovascular thromboembolic disorders and thromboembolic disorders in the chambers of the heart or in the peripheral circulation. The compound of the present invention is therefore useful as a medicament.

The invention claimed is:

1. A method for inhibiting factor XIa, which method comprises contacting 4-[{(2S,4S)-1-(4-carbamimidoylbenzoyl)-4-[4-(methylsulfonyl)-1-piperazinyl]-2-pyrrolidinyl}carbonyl)amino]benzoic acid or a pharmaceutically acceptable salt thereof with factor XIa.

2. A method for treating a patient suffering from or susceptible to a thromboembolic disease, which method comprises administering to said patient a therapeutically effective amount of 4-[({(2S,4S)-1-(4-carbamimidoylbenzoyl)-4-[4-(methylsulfonyl)-1-piperazinyl]-2-pyrrolidinyl}carbonyl)amino]benzoic acid or a pharmaceutically acceptable salt thereof.

3. The method according to claim 2, wherein the thromboembolic disease is selected from the group consisting of arterial cardiovascular thromboembolic disorders, venous cardiovascular thromboembolic disorders, arterial cerebrovascular thromboembolic disorders, venous cerebrovascular thromboembolic disorders and thromboembolic disorders in the chambers of the heart or in the peripheral circulation.

4. The method according to claim 3, wherein the thromboembolic disease is selected from disseminated intravascular coagulopathy (DIC), acute respiratory distress syndrome, acute lung injury, sepsis, angina, unstable angina, an acute coronary syndrome, coronary artery disease, myocardial infarction, atrial fibrillation, ischemic sudden death, transient ischemic attack, stroke, acute stroke, lacuna infarction, atherosclerotic thrombotic cerebral infarction, atherothrombosis, atherosclerosis, peripheral occlusive arterial disease, venous thrombosis, deep vein thrombosis, thrombophlebitis, arterial embolism, coronary arterial thrombosis, cerebral thrombosis, cerebral arterial thrombosis, cerebral embolism, cardiogenic embolism, kidney embolism, portal vein thrombosis, pulmonary embolism, pulmonary infarction, liver embolism, mesenteric artery and/or vein embolism, occlusion of retinal vein and/or artery, systemic embolism, antiphospholipid antibody syndrome, thrombosis resulting from coronary artery bypass graft surgery and thrombosis resulting from medical implants, devices, or procedures in which blood is exposed to an artificial surface that promotes thrombosis.

* * * * *